(12) United States Patent
Zecri et al.

(10) Patent No.: US 9,982,017 B2
(45) Date of Patent: May 29, 2018

(54) SYNTHETIC APELIN MIMETICS FOR THE TREATMENT OF HEART FAILURE

(71) Applicant: Novartis AG, Basel (CH)

(72) Inventors: Frederic Zecri, Brookline, MA (US);
Andrei Golosov, Cambridge, MA (US);
Philipp Grosche, Inzlingen (DE);
Hongjuan Zhao, Lexington, MA (US);
Qi-Ying Hu, Needham, MA (US);
Hidetomo Imase, Somerville, MA (US)

(73) Assignee: NOVARTIS AG, Basel (CH)

( * ) Notice: Subject to any disclaimer, the term of this patent is extended or adjusted under 35 U.S.C. 154(b) by 215 days.

(21) Appl. No.: 14/714,914

(22) Filed: May 18, 2015

(65) Prior Publication Data

US 2015/0252076 A1   Sep. 10, 2015

Related U.S. Application Data

(63) Continuation of application No. 14/165,680, filed on Jan. 28, 2014, now Pat. No. 9,067,971, which is a continuation of application No. 13/747,621, filed on Jan. 23, 2013, now Pat. No. 8,673,848.

(60) Provisional application No. 61/591,557, filed on Jan. 27, 2012, provisional application No. 61/717,760, filed on Oct. 24, 2012, provisional application No. 61/731,697, filed on Nov. 30, 2012.

(51) Int. Cl.
| | | |
|---|---|---|
| A61K 38/10 | (2006.01) | |
| C07K 7/08 | (2006.01) | |
| C07K 7/56 | (2006.01) | |
| C07K 7/60 | (2006.01) | |
| A61K 38/00 | (2006.01) | |

(52) U.S. Cl.
CPC .............. C07K 7/08 (2013.01); A61K 38/10 (2013.01); C07K 7/56 (2013.01); C07K 7/60 (2013.01); A61K 38/00 (2013.01)

(58) Field of Classification Search
None
See application file for complete search history.

(56) References Cited

U.S. PATENT DOCUMENTS

| | | |
|---|---|---|
| 5,759,804 A | 6/1998 | Godiska et al. |
| 6,492,324 B1 | 12/2002 | Hinuma et al. |
| 6,555,339 B1 | 4/2003 | Liaw et al. |
| 6,774,221 B1 | 8/2004 | Nishimura et al. |
| 7,635,751 B2 | 12/2009 | Kitada et al. |
| 7,736,646 B2 | 6/2010 | Krieg |
| 7,947,280 B2 | 5/2011 | Ashley et al. |
| 8,673,848 B2 | 3/2014 | Zecri et al. |
| 2003/0092618 A1 | 5/2003 | Hinuma et al. |
| 2003/0119021 A1 | 6/2003 | Koster et al. |
| 2004/0082496 A1 | 4/2004 | Acton et al. |
| 2004/0116336 A1 | 6/2004 | Kitada et al. |
| 2005/0152836 A1 | 7/2005 | Ashley et al. |
| 2006/0045880 A1 | 3/2006 | Krieg |
| 2006/0159676 A1 | 7/2006 | Krieg |
| 2007/0088244 A1 | 4/2007 | Miller et al. |
| 2008/0031871 A1 | 2/2008 | Allen et al. |
| 2008/0182779 A1 | 7/2008 | Ashley et al. |
| 2011/0008346 A1 | 1/2011 | Duckers |
| 2011/0097710 A1 | 4/2011 | Macrae et al. |
| 2011/0123534 A1 | 5/2011 | Duckers |
| 2011/0305663 A1 | 12/2011 | Gosselin et al. |

(Continued)

FOREIGN PATENT DOCUMENTS

| | | |
|---|---|---|
| EP | 1116727 A1 | 7/2001 |
| EP | 2017355 A1 | 1/2009 |

(Continued)

OTHER PUBLICATIONS

Murza et al., "Elicidation of the Structure-Activity Relationships of Apelin: Influence of Unnatural Amino Acids on Binding, Signaling, and Plasma Stability," Chem Med Chem 7:318-325 (Feb. 2012).

(Continued)

*Primary Examiner* — Lianko G Garyu
*Assistant Examiner* — Khalid Kader
(74) *Attorney, Agent, or Firm* — Judith D. Kuntz

(57) ABSTRACT

The invention provides a synthetic polypeptide of Formula I':

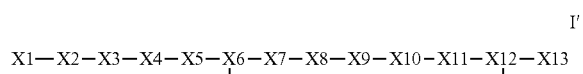

or an amide, an ester or a salt thereof, wherein X1, X2, X3, X4, X5, X6, X7, X8, X9, X10, X11, X12 and X13 are defined herein. The polypeptides are agonist of the APJ receptor. The invention also relates to a method for manufacturing the polypeptides of the invention, and its therapeutic uses such as treatment or prevention of acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia. The present invention further provides a combination of pharmacologically active agents and a pharmaceutical composition.

17 Claims, No Drawings

(56) References Cited

U.S. PATENT DOCUMENTS

2014/0142022 A1 5/2014 Zecri et al.
2015/0030594 A1 1/2015 Yuan et al.
2015/0031604 A1 1/2015 Zecri et al.

FOREIGN PATENT DOCUMENTS

| EP | 2330125 A2 | 6/2011 |
|---|---|---|
| RU | 2457216 A | 7/2012 |
| WO | 2001090123 A2 | 11/2001 |
| WO | 2003063892 A1 | 8/2003 |
| WO | 2005023863 A1 | 3/2005 |
| WO | 2005106493 A1 | 11/2005 |
| WO | 2006009902 A2 | 1/2006 |
| WO | 06041205 A1 | 4/2006 |
| WO | 2007039184 A2 | 4/2007 |
| WO | 09033669 A2 | 3/2009 |
| WO | 09033819 A2 | 3/2009 |
| WO | 2009033784 A2 | 3/2009 |
| WO | 2009075566 A1 | 6/2009 |
| WO | 10053545 A2 | 5/2010 |
| WO | 2010115874 A1 | 10/2010 |
| WO | 11056073 A2 | 5/2011 |
| WO | 11133948 A2 | 10/2011 |
| WO | 2013106437 A1 | 7/2013 |
| WO | 2015013165 A2 | 1/2015 |
| WO | 2015013167 A2 | 1/2015 |

OTHER PUBLICATIONS

Sidorova et al., "Synthesis and Cardioprotective properties of Apelin-12 and its Structural Analogs," Russian Journal of Bioorganic Chemistry 38(1):40-51 (Jan. 1, 2012).
Murza et al., "Elucidation of the Structure-Activity Relationships of Apelin: Influence of Unnatural Amino Acids on Binding, Signaling and Plasma Stability," Journal of Peptide Science 18(1):S104 (Sep. 2012).
Lee et al., "Modification of the Terminal Residue of Apelin-13 Antagonizes Its Hypotensive Action," Endocrinology 146 (1):231-236 (Oct. 14, 2004).
Francia et al., "The Apelin/APJ System From Vascular Biology to Heart Failure," High Blood Press Cardiovasc Prev 13 (4):159-162 (Oct. 22, 2006).
Zeng et al., "Effects and mechanisms of apelin-13 on ischemia/reperfusion injury in rat heart," Chinese Pharmacological Bulletin 23(1):82-85 (Jan. 2007).
Simpkin et al., "Apelin-13 and apelin-36 exhibit direct cardio protective activity against ischemia reperfusion injury," Basic Research in Cardiology 102(6):518-528 (Nov. 2007).
Zhang et al., "The Effect of Apelin-13 on Ischemia-Induced Cardiomyocyte Apoptosis in Acute Myocardial Ischemia Rats," Chinese Journal of Arteriosclerosis 2008-2009.
Fukase et al., "Synthetic Study on Peptide Antiobiotic Nisin. V. Total Synthesis of Nisin," Bull. Chem. Soc. Jpn. 65:2227-2240 (1992).
Rastaldo et al., "Apelin-13 limits infarct size and improves cardiac postischemic mechanical recovery only if given after ischemia" American Journal of Physiology—Heart and Circulatory Physiology 300(6):H2308-H2315 (Jun. 2011).
Charles, Christopher, "Update on apelin peptides as putative targets for cardiovascular drug discovery" Expert Opinion on Drug Discovery 6(6):633-644 , (Jun. 2011).
Tycinska et al., "Apelin in acute myocardial infarction and heart failure induced by ischemia," Clinica Chimica Acta 413: 406-410 (Nov. 25, 2011).
Dowd et al., "A human gene that shows identity with the gene encoding the angiotensin receptor is located on chromosome 11," Gene 136:355-360 (1993).
Habata et al. "Apelin, the natural ligand of the orphan receptor APJ, is abundantly secreted in the colostrum," Biochimica et Biophysica Acta 1452:25-35 (1999).
Hamada et al., "Evaluation of novel cyclic analogues of apelin," International Journal of molecular medicine 22:547-552 (2008).
Bernardes et al., "From Disulfide- to Thioether-Linked Glycoproteins," Angew. Chem. Int. Ed 47:2244-2247 (2008).
Ranganathan et al., "Triply bridged (1,3,5) cyclophanes from cystine and lanthionine linkers—a comparison," Tetrahedron 66:3923-3929 (2010).
Japp et al., "Vascular effects of apelin in vivo in man," Journal of the american college of cardiology 52:908-13 (2008).
Medhurst et al., "Pharmacological and immunohistochemical characterization of the APJ receptor and its endogenous ligand apelin," Journal of neurochemistry 84:1162-1172 (2003).
Macaluso and Glen, "Exploring the 'RPRL' Motif of apelin-13 through molecular simulation and biological evaluation of cyclic peptide analogues," ChemMedChem 5:1247-1253 (2010).
Macaluso et al., "Discovery of competitive apelin receptor (APJ) antagonist," ChemMedChem 6:1017-1023 (2011).
Pisarenko et al., Effects of structural analogues of apelin-12 in acute myocardial infarction in rats, Journal of Pharmacology and Pharmcotherapeutics, Jul.-Sep. 2013, vol. 4, Issue 3, pp. 198-203.
Pisarenko et. al, Apelin-12 and its structural analog enhance antioxidant defense in experimental myocardial ischemia and reperfusion, Mol. Cell Biochem (2014), 391:241-250.
Margathe et al., Structure-Activity Relationship Studies toward the Discovery of Selective Apelin Receptor Agonists, Journal of Medicinal Chemistry (2014), vol. 57, pp. 2908-2919.

SYNTHETIC APELIN MIMETICS FOR THE TREATMENT OF HEART FAILURE

This application is a continuation application of U.S. application Ser. No. 14/165,680 filed on Jan. 28, 2014, which is a continuation application of U.S. application Ser. No. 13/747,621 filed on Jan. 23, 2013, which claims benefit under 35 U.S.C. § 119(e) of U.S. Provisional Application No. 61/591,557, filed Jan. 27, 2012; U.S. Provisional Application No. 61/717,760, filed on Oct. 24, 2012 and U.S. Provisional Application No. 61/731,697 filed on Nov. 30, 2012; the contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Jun. 28, 2013, is named PAT054961-US-NP_SL.txt and is 67,220 bytes in size.

FIELD OF THE INVENTION

The invention relates to novel compositions comprising modified peptide and polypeptide sequences designed to treat cardiovascular disease in subjects to whom they are administered, and which exhibit greater resistance to degradation, and equivalent or greater bioactivity than their wild type counterparts. The invention also relates to methods of making said compositions and using said compositions as pharmaceutically active agents to treat cardiovascular disease.

BACKGROUND OF THE INVENTION

The incidence of heart failure in the Western world is approximately 1/100 adults after 65 yrs of age. The most common pathology is a chronic deficit in cardiac contractility and, thereby, cardiac output, i.e., the effective volume of blood expelled by either ventricle of the heart over time. Patients with chronic heart failure can have acute episodes of decompensation, i.e., failure of the heart to maintain adequate blood circulation, where cardiac contractility declines further. There are ~500K hospitalizations per year for "acute decompensated heart failure" (ADHF) in the USA alone.

Current therapies for ADHF include diuretics, vasodilators, and inotropes, which directly increase cardiac contractility. Current intravenous inotropes (dobutamine, dopamine, milrinone, levosimendan) are used in the acute setting, despite their association with adverse events such as arrhythmia and increased long-term mortality. These liabilities have prevented their application in chronic heart failure. Digoxin is an oral inotrope, but is limited by a narrow therapeutic index, increased arrhythmogenic potential and contraindication in renal insufficiency.

A therapy for heart failure that increases cardiac contractility without arrhythmogenic or mortality liabilities is urgently needed for ADHF, but could also address the enormous unmet medical need in chronic heart failure.

Apelin is the endogenous ligand for the previously orphan G-protein-coupled receptor (GPCR), APJ, also referred to as apelin receptor, angiotension-like-1 receptor, angiotension II-like-1 receptor, and the like. The apelin/APJ pathway is widely expressed in the cardiovascular system and apelin has shown major beneficial cardiovascular effects in preclinical models. Acute apelin administration in humans causes peripheral and coronary vasodilatation and increases cardiac output (Circulation. 2010; 121:1818-1827). As a result, APJ agonism is emerging as an important therapeutic target for patients with heart failure. Activation of the apelin receptor APJ is thought to increase cardiac contractility and provide cardioprotection, without the liabilities of current therapies. However, the native apelins exhibit a very short half life and duration of action in vivo.

It is therefore desirable to identify peptides and polypeptides that mimic the function of apelin, but have increased half-life and demonstrate equivalent or greater bioactivity than the naturally occuring apelin. Furthermore, it is desirable to identify apelin analog peptides and polypeptides which exhibit increased conformational constraints, i.e., the ability to achieve and maintain an active conformational state such that the peptides and polypeptides can interact with their receptors and/or other pathway targets without the need for additional folded or repositioning. There is a need for use of such peptide and polypeptide analogs, compositions comprising said analogs, and methods of making and using said compositions as pharmaceutically active agents to treat diseases, such as cardiovascular diseases.

SUMMARY OF THE INVENTION

The aim of the present invention is to provide novel peptides and polypeptides which are useful as APJ agonists, and which also possess at least one of the following improvements over wild type apelin and other known apelin analogs: increased half-life; greater immunity to degradation upon administration and/or upon solubilization; and increased conformational constraints, all while exhibiting the same or greater biological activity as wild type apelin. The peptides and polypeptides of this invention are thus particularly useful for the treatment or prevention of cardiovascular diseases such as heart failure, disorders and conditions associated with heart failure, and disorders and conditions responsive to the activation of APJ receptor activity.

In one embodiment, the peptides and polypeptides of the invention are particularly useful for the treatment or prevention of a disorder or condition associated with heart failure, or a disorder responsive to the activation (or agonism) of the APJ receptor activity. In another embodiment, the peptides and polypeptides of the invention are useful in the treatment of acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

The invention pertains to the peptides and polypeptides, pharmaceutical compositions, and methods of manufacture and use thereof, as described herein. Examples of peptides and polypeptides of the invention include the peptides and polypeptides according to any one of Formulae I to IX, or an amide, an ester or a salt thereof, as well as any peptides or polypeptides specifically listed herein, including but not limited to the experimental examples.

The invention therefore provides a peptide or a polypeptide formula (I'):

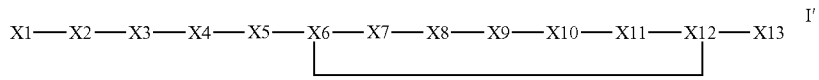

wherein:

X1 is the N-terminus of the polypeptide and is either absent or is selected from pE, R, Isn, Q, A, K, and 5-amino-valeric acid;

X2 is R, A, r, N-Me-R, K, H, hF, hK, F, E or Orn;

X3 is P, A, a, p, 4-PhP, K, D, pipecolic acid, or cysteine wherein the side chain of cysteine forms a disulfide bond with the side chain of the cysteine at the X7 position;

X4 is R, A, r, N-Me-R, F, E or cysteine wherein the side chain of cysteine forms a disulfide bond with the side chain of the cysteine at the X7 position;

X5 is L, Cha, A, D-L, N-Me-L, K, D, 4-PhF or F;

X6 and X12 are independently a natural or unnatural amino acid selected from C, c, hC, D-hC, K, D, Orn, Dab or E wherein the side chain of X6 and X12 are linked together via a covalent bond forming either a monosulfide (—S—), a disulfide (—S—S—) or an amide bond (—NHC(O)— or —C(O)—NH—) or a linkage of Formula —S—CH$_2$—C(=Z)—CH$_2$—S—; wherein Z is O, N—O—CH$_2$C(O)-L$^1$-R$^1$ or N—NH—CH$_2$C(O)-L$^1$-R$^1$ wherein R$^1$ is a fatty acid derivative and L$^1$ is a linker containing one or more amino acids and/or one or more —NH—C$_{2-6}$-alkylene-NH— units; or alternatively X6 is K, X13 is absent and X12 is F or f wherein the C-terminus of X12 form an amide bond with the amino side chain of X6;

X7 is H, h, A, N-Me-A, a, Aib, K, Nal, F, P, Dap, N, E or cysteine wherein the side chain of the cysteine forms a disulfide bond with the side chain of the cysteine at position X3 or with the side chain of the cysteine at position X4;

X8 is K, k, F, f, A, hF, N-Me-R, E or 4-amino-Isn;

X9 is G, N-Me-G, A, D, L, R or Aib;

X10 is P, A, p, 4-PhP or pipecolic acid,

X11 is M, D-Nle, Nle, N-Me-Nle, M(O), A, F, Y, L, K, 3-PyA or Cha; and

X13 is the C-terminus and is absent or is selected from F, f, N-Me-F, Nal, D-Nal, 3-Br—F, (S)-β-3-F, I, A, a, K, Dap, H and E;

wherein:

Nle is L-norleucine;

D-hC is D-homocysteine hC is L-homocysteine;

hF is L-homophenylalanine;

hK is L-lysine;

Nal is L-naphathaline;

Orn is ornithine;

Aib is α-aminoisobutyric acid;

Dab is (S)-diaminobutyric acid;

Dap is (S)-2,3-diaminopropionic acid;

M(O) is methionine sulfone;

Cha is (S)-β-cyclohexylalanine;

4-amino-Isn is 4-aminopiperidine-4-carboxylic acid;

Isn is isonipecotinoyl;

pE is L-pyroglutamic acid;

3-PyA is 3-(3-pyridyl)-L-alanine;

4-PhF is 4-Phenyl-L-phenylalanine;

wherein the N-terminus and the C-terminus optionally form a ring together with 1, 2, 3 or 4 glycine amino acids; and wherein the amino group in the side chain of K, Orn, Dab, Dap, hK or 4-amino-Isn is optionally linked to a lipophilic group via an amide bond;

or an amide, an ester or a salt of the polypeptide; or a polypeptide substantially equivalent thereto.

As further explained herein, the art-recognized three letter or one letter abbreviations are used to represent amino acid residues that constitute the peptides and polypeptides of the invention. Except when preceded with "D," the amino acid is an L-amino acid. When the one letter abbreviation is a capital letter, it refers to the L-amino acid. When the one letter abbreviation is a lower case letter, it refers to the D-amino acid.

Any of the above-listed amino acid residues of Formula I', or its related formulae described herein, e.g., Formulae I, II to IX, may be substituted in a conservative fashion, provided the peptide or polypeptide of the invention still retains functional activity and structural properties (e.g., half-life extension, protection from degradation, conformational constraint). Principle and examples of permissible conservative amino acid substitutions are further explained herein.

The polypeptides of the invention, by activating APJ receptor, have utility in the treatment of acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

In a preferred embodiment the polypeptides of the invention are useful in the treatment of acute decompensated heart failure (ADHF).

In another embodiment, the invention pertains to a method for treating disorder or disease responsive to the activation of the APJ receptor, in a subject in need of such treatment, comprising: administering to the subject an effective amount of a polypeptide according to anyone of Formulae I to IX, or an amide, an ester of a salt thereof, such that the disorder or disease responsive to the activation of the APJ receptor in the subject is treated.

In yet another embodiment, the invention pertains to pharmaceutical compositions, comprising a polypeptide according to anyone of Formulae I to IX, or an amide, an ester or salt thereof, and one or more pharmaceutically acceptable carriers.

In still another embodiment, the invention pertains to combinations including, a polypeptide according to anyone of Formulae I to IX, or an amide, an ester or a salt thereof, and pharmaceutical combinations of one or more therapeutically active agents.

In another embodiment, the invention pertains to a method for activation of the APJ receptor in a subject in need thereof, comprising: administering to the subject a therapeutically effective amount of a polypeptide according to anyone of Formulae I to IX, or an amide, an ester or a salt thereof.

DETAILED DESCRIPTION OF THE INVENTION

For purposes of interpreting this specification, the following definitions will apply unless specified otherwise and whenever appropriate, terms used in the singular will also include the plural and vice versa.

As used herein, "disorders or diseases responsive to the modulation of the APJ receptor," "disorders and conditions responsive to the modulation of the APJ," "disorders and conditions responsive to the modulation of APJ receptor activity," "disorders responsive to the activation (or agonism) of the APJ receptor activity," and like terms include acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

As used herein, "Activation of APJ receptor activity," or "Activation of the APJ receptor," refers to an increase in the APJ receptor activity. The activation of the APJ receptor activity is also refered to as "agonism" of the APJ receptor, e.g., by administration of the peptides and polypeptides of the invention.

As used herein, the terms "polypeptide" and "peptide" are used interchangeably to refer to two or more amino acids linked together. Except for the abbreviations for the uncommon or unatural amino acids set forth in Table 1 below, the art-recognized three letter or one letter abbreviations are used to represent amino acid residues that constitute the peptides and polypeptides of the invention. Except when preceded with "D", the amino acid is an L-amino acid. When the one letter abbreviation is a capital letter, it refers to the D-amino acid. When the one letter abbreviation is a lower case letter, it refers to the L-amino acid. Groups or strings or amino acid abbreviations are used to represent peptides. Peptides are indicated with the N-terminus on the left and the sequence is written from the N-terminus to the C-terminus.

Peptides of the invention contain non-natural amino acids (i.e., compounds that do not occur in nature) and other amino acid analogs as are known in the art may alternatively be employed.

Certain non-natural amino acids can be introduced by the technology described in Deiters et al., J Am Chem Soc 125:11782-11783, 2003; Wang and Schultz, Science 301: 964-967, 2003; Wang et al., Science 292:498-500, 2001; Zhang et al., Science 303:371-373, 2004 or in U.S. Pat. No. 7,083,970. Briefly, some of these expression systems involve site-directed mutagenesis to introduce a nonsense codon, such as an amber TAG, into the open reading frame encoding a polypeptide of the invention. Such expression vectors are then introduced into a host that can utilize a tRNA specific for the introduced nonsense codon and charged with the non-natural amino acid of choice. Particular non-natural amino acids that are beneficial for purpose of conjugating moieties to the polypeptides of the invention include those with acetylene and azido side chains.

One or more of the natural or un-natural amino acids in a peptide of the invention may be modified, for example, by the addition of a chemical entity such as a carbohydrate group, a phosphate group, a farnesyl group, an isofarnesyl group, a fatty acid group ($C_qH_{q+1}C(O)_2H$ wherein q is 3 to 20), a linker for conjugation, functionalization, or other modification, etc. Said modifications may be done in a site-specific or non-site-specific manner. In a preferred embodiment, the modifications of the peptide lead to a more stable peptide (e.g., one exhibiting greater half-life in vivo). These modifications may include the incorporation of additional D-amino acids, etc. None of the modifications should substantially interfere with the desired biological activity of the peptide, but such modifications may confer desirable properties, e.g., enhanced biological activity, on the peptide.

Said modifications enhance the biological properties of the proteins of the invention relative to the wild-type proteins, as well as, in some cases, serving as points of attachment for, e.g., labels and protein half-life extension agents, and for purposes of affixing said variants to the surface of a solid support.

In certain embodiments, such modifications, e.g., site-specific modifications, are used to attach conjugates, e.g., PEG groups to polypeptides, and/or peptides of the invention, for purposes of, e.g., extending half-life or otherwise improving the biological properties of said polypeptides, and/or peptides. Said techniques are described further herein.

In other embodiments, such modifications, e.g., site-specific modifications, are used to attach other polymers and small molecules and recombinant protein sequences that extend half-life of the polypeptide of the invention. One such embodiment includes the attachment of fatty acids or specific albumin binding compounds to polypeptides, and/or peptides. In other embodiments, the modifications are made at a particular amino acid type and may be attached at one or more sites on the polypeptides.

In other embodiments, such modifications, e.g., site-specific modifications, are used as means of attachment for the production of wild-type and/or variant multimers, e.g., dimers (homodimers or heterodimers) or trimers or tetramers. These multimeric protein molecules may additionally have groups such as PEG, sugars, and/or PEG-cholesterol conjugates attached or be fused either amino-terminally or carboxy-terminally to other proteins such as Fc, Human Serum Albumin (HSA), etc.

In other embodiments, such site-specific modifications are used to produce proteins, polypeptides and/or peptides wherein the position of the site-specifically incorporated pyrrolysine or pyrrolysine analogue or non-naturally occurring amino acids (para-acetyl-Phe, para-azido-Phe) allows for controlled orientation and attachment of such proteins, polypeptides and/or peptides onto a surface of a solid support or to have groups such as PEG, sugars and/or PEG-cholesterol conjugates attached.

In other embodiments, such site-specific modifications are used to site-specifically cross-link proteins, polypeptides and/or peptides thereby forming hetero-oligomers including, but not limited to, heterodimers and heterotrimers. In other embodiments, such site-specific modifications are used to site-specifically cross-link proteins, polypeptides and/or peptides thereby forming protein-protein conjugates, protein-polypeptide conjugates, protein-peptide conjugates, polypeptide-polypeptide conjugates, polypeptide-peptide conjugates or peptide-peptide conjugates. In other embodiments, a site specific modification may include a branching point to allow more than one type of molecule to be attached at a single site of a protein, polypeptide or peptide.

In other embodiments, the modifications listed herein can be done in a non-site-specific manner and result in protein-protein conjugates, protein-polypeptide conjugates, protein-peptide conjugates, polypeptide-polypeptide conjugates, polypeptide-peptide conjugates or peptide-peptide conjugates of the invention.

In some embodiments, the present invention provides complexes which comprise at least one peptide or polypeptide of anyone of Formulae I-IX bound to an antibody, such as an antibody why specifically binds a peptide or polypeptide as disclosed herein.

One of ordinary skill in the art will appreciate that various amino acid substitutions, e.g, conservative amino acid substitutions, may be made in the sequence of any of the polypeptides described herein, without necessarily decreasing its activity. As used herein, "amino acid commonly used as a substitute thereof" includes conservative substitutions (i.e., substitutions with amino acids of comparable chemical characteristics). For the purposes of conservative substitution, the non-polar (hydrophobic) amino acids include alanine, leucine, isoleucine, valine, glycine, proline, phenylalanine, tryptophan and methionine. The polar (hydrophilic), neutral amino acids include serine, threonine, cysteine, tyrosine, asparagine, and glutamine. The positively charged (basic) amino acids include arginine, lysine and histidine. The negatively charged (acidic) amino acids include aspartic acid and glutamic acid. Examples of amino acid substitutions include substituting an L-amino acid for its corresponding D-amino acid, substituting cysteine for homocysteine or other non natural amino acids having a thiol-containing side chain, substituting a lysine for homolysine, diaminobutyric acid, diaminopropionic acid, ornithine or other non natural amino acids having an amino containing side chain, or substituting an alanine for norvaline or the like.

The term "amino acid," as used herein, refers to naturally occurring amino acids, unnatural amino acids, amino acid analogues and amino acid mimetics that function in a manner similar to the naturally occurring amino acids, all in their D and L stereoisomers if their structure allows such stereoisomeric forms. Amino acids are referred to herein by either their name, their commonly known three letter symbols or by the one-letter symbols recommended by the IUPAC-IUB Biochemical Nomenclature Commission.

The term "naturally occurring" refers to materials which are found in nature and are not manipulated by man. Similarly, "non-naturally occurring," "un-natural," and the like, as used herein, refers to a material that is not found in nature or that has been structurally modified or synthesized by man. When used in connection with amino acids, the term "naturally occurring" refers to the 20 conventional amino acids (i.e., alanine (A or Ala), cysteine (C or Cys), aspartic acid (D or Asp), glutamic acid (E or Glu), phenylalanine (F or Phe), glycine (G or Gly), histidine (H or His), isoleucine (I or Ile), lysine (K or Lys), leucine (L or Leu), methionine (M or Met), asparagine (N or Asn), proline (P or Pro), glutamine (Q or Gln), arginine (R or Arg), serine (S or Ser), threonine (T or Thr), valine (V or Val), tryptophan (W or Trp), and tyrosine (Y or Tyr)).

The terms "non-natural amino acid" and "unnatural amino acid," as used herein, are interchangeably intended to represent amino acid structures that cannot be generated biosynthetically in any organism using unmodified or modified genes from any organism, whether the same or different. The terms refer to an amino acid residue that is not present in the naturally occurring (wild-type) apelin protein sequence or the sequences of the present invention. These include, but are not limited to, modified amino acids and/or amino acid analogues that are not one of the 20 naturally occurring amino acids, selenocysteine, pyrrolysine (Pyl), or pyrroline-carboxy-lysine (Pcl, e.g., as described in PCT patent publication WO2010/48582). Such non-natural amino acid residues can be introduced by substitution of naturally occurring amino acids, and/or by insertion of non-natural amino acids into the naturally occurring (wild-type) Apelin protein sequence or the sequences of the invention. The non-natural amino acid residue also can be incorporated such that a desired functionality is imparted to the apelin molecule, for example, the ability to link a functional moiety (e.g., PEG). When used in connection with amino acids, the symbol "U" shall mean "non-natural amino acid" and "unnatural amino acid," as used herein.

In addition, it is understood that such "unnatural amino acids" require a modified tRNA and a modified tRNA synthetase (RS) for incorporation into a protein. These "selected" orthogonal tRNA/RS pairs are generated by a selection process as developed by Schultz et al. or by random or targeted mutation. As way of example, pyrroline-carboxy-lysine is a "natural amino acid" as it is generated biosynthetically by genes transferred from one organism into the host cells and as it is incorporated into proteins by using natural tRNA and tRNA synthetase genes, while p-aminophenylalanine (See, Generation of a bacterium with a 21 amino acid genetic code, Mehl R A, Anderson J C, Santoro S W, Wang L, Martin A B, King D S, Horn D M, Schultz P G. J Am Chem Soc. 2003 Jan. 29; 125(4):935-9) is an "unnatural amino acid" because, although generated biosynthetically, it is incorporated into proteins by a "selected" orthogonal tRNA/tRNA synthetase pair.

Modified encoded amino acids include, but are not limited to, hydroxyproline, γ-carboxyglutamate, O-phosphoserine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminoproprionic acid, N-ethylglycine, N-methylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucin, N-methylpentylglycine, N-methylvaline, naphthalanine, norvaline, norleucine, ornithine, pentylglycine, pipecolic acid and thioproline. The term "amino acid" also includes naturally occurring amino acids that are metabolites in certain organisms but are not encoded by the genetic code for incorporation into proteins. Such amino acids include, but are not limited to, ornithine, D-ornithine, and D-arginine.

The term "amino acid analogue," as used herein, refers to compounds that have the same basic chemical structure as a naturally occurring amino acid, by way of example only, an α-carbon that is bound to a hydrogen, a carboxyl group, an amino group, and an R group. Amino acid analogues include the natural and unnatural amino acids which are chemically blocked, reversibly or irreversibly, or their C-terminal carboxy group, their N-terminal amino group and/or their side-chain functional groups are chemically modified. Such analogues include, but are not limited to, methionine sulfoxide, methionine sulfone, S-(carboxymethyl)-cysteine, S-(carboxymethyl)-cysteine sulfoxide, S-(carboxymethyl)-cysteine sulfone, aspartic acid-(beta-methyl ester), N-ethylglycine, alanine carboxamide, homoserine, norleucine, and methionine methyl sulfonium.

TABLE 1

Un-natural or Non-natural Amino Acids as described in the invention:

| Symbol | Name | Structure |
|---|---|---|
| Aib | α-Aminoisobutyric acid | |
| M(O) | Methionine sulfone | |
| 1-Nal | 1-Naphthalanine | |
| 2-Nal | 2-Naphthalanine | |
| Cha | β-Cyclohexylalanine | |
| Dab | Diamino-butyric acid | |
| Dap | 2,3-Diamino propionic acid | |
| hC | Homocysteine | |
| hF | Homo-phenylalanine | 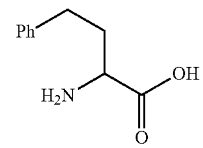 |
| hK | Homolysine | 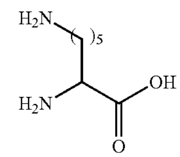 |
| Nle | Norleucine | 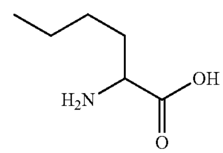 |
| Orn | Ornithine | 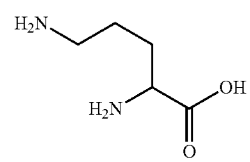 |
| β-3-F | β-3-phenylalanine | 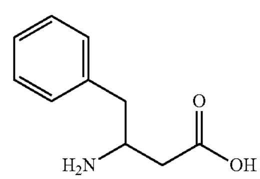 [SMILES: NC(CC(=O)O)Cc1ccccc1] |
| 4-amino-Isn | 4-Amino-piperidine-4-carboxylic acid (4 amino group form the peptidic bond) | 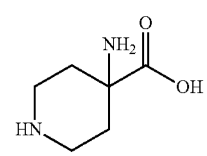 |
| Isn | Isonipecotinoic acid | 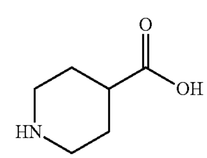 |
| pE | Pyroglutamic acid | 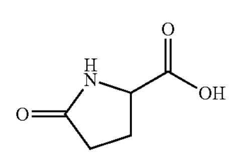 |
| 4-PhP | 4-Phenylproline | 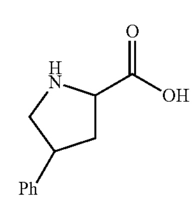 [SMILES: O=C(O)C1CC(c2ccccc2)CN1] |

TABLE 1-continued

Un-natural or Non-natural Amino Acids as described in the invention:

| Symbol | Name | Structure |
|---|---|---|
|  | Pipecolinic acid |  |
|  | 5-Aminovaleric acid |  |
| O2Oc | 8-Amino-3,6-dioxaoctanoic acid | 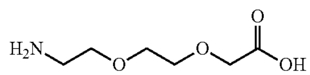 |
| 3-PyA | 3-(3-pyridyl)-alanine | 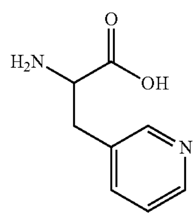 [SMILES: NC(Cc1cccnc1)C(=O)O] |
| 4-PhF | 4-phenyl-phenylalanine | 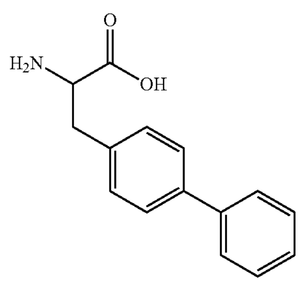 [SMILES: NC(Cc1ccc(-c2ccccc2)cc1)C(=O)O] |

Nal refers both to 1-Naphthalanine and 2-Naphthalanine, preferably 2-naphthalanine. 4-Phenylproline refers to both cis and trans 4-Phenylproline, preferably trans-4-phenylproline As used herein the term "amide" refers to an amide derivative of the carboxylic acid group at the C-terminus (e.g. —C(O)NH$_2$, —C(O)NH—C$_{1-6}$ alkyl, —C(O)NH—C1-2alkylphenyl, —C(O)NH—NHBn or —C(O)N(C$_{1-6}$ alkyl)$_2$).

The term "amide" also refer to derivative of the amino group at the N-terminus (e.g. —NHC(O)C$_{1-16}$alkyl, —NHC(O)(CH$_2$)$_n$Ph (n is an integer of 1 to 6), —NHC(O)(CH$_2$)$_2$CO$_2$H, 4-Cl-Ph-(CH$_2$)$_3$C(O)NH—, C$_{11}$H$_{23}$C(O)NH—(CH$_2$)$_2$—O—(CH$_2$)$_2$—O—CH$_2$—C(O)—NH—, C$_{13}$H$_{27}$C(O)NH—(CH$_2$)$_2$—O—(CH$_2$)$_2$—O—CH$_2$—C(O)—NH—; C$_{15}$H$_{27}$C(O)NH—(CH$_2$)$_2$—O—(CH$_2$)$_2$—O—CH$_2$—C(O)NH—, Ph-CH$_2$CH$_2$NHC(O)—NH— or CH$_3$(OCH$_2$CH$_2$)$_m$C(O)NH— (m is an integer of 1 to 12).

As used herein, the term "ester" refers to an ester derivative of the carboxylic acid group at the C-terminus (e.g —COOR) form wherein R of the ester refers to C$_{1-6}$ alkyl groups such as methyl, ethyl, n-propyl, isopropyl, n-butyl, etc., C$_{3-8}$ cycloalkyl groups such as cyclopentyl, cyclohexyl, etc., C$_{6-10}$ aryl groups such as phenyl, α-naphthyl, etc., C$_{6-10}$ aryl-C$_{1-6}$ alkyl groups, for example phenyl-C$_{1-2}$ alkyl groups such as benzyl, phenethyl, benzhydryl, etc., and α-naphthyl-C$_{1-2}$ alkyl groups such as α-naphthylmethyl and the like. Mention may also be made of pivaloyloxymethyl ester and the like, which are commonly used as esters for oral administration. When the polypeptides of the invention possess additional carboxyl or carboxylate groups in positions other than the C terminus, those polypeptides in which such groups are amidated or esterified also fall under the category of the polypeptide of the invention. In such cases, the esters may for example be the same kinds of esters as the C-terminal esters mentioned above.

The term "APJ" (also referred to as "apelin receptor," "angiotension-like-1 receptor," "angiotension II-like-1 receptor," and the like) indicates a 380 residue, 7 transmembrane domain, Gi coupled receptor whose gene is localized on the long arm of chromosome 11 in humans (NCBI Reference Sequence: NP_005152.1, and encoded by NCBI Reference Sequence: NM_005161). APJ was first cloned in 1993 from genomic human DNA using degenerate oligonucleotide primers (O'Dowd et al. Gene, 136:355-60, 1993) and shares significant homology with angiotensin II receptor type 1. Despite this homology however, angiotensin II does not bind APJ. Although orphan for many years, the endogenous ligand has been isolated and named apelin (Tatemoto et al., Biochem Biophys Res Commun 251, 471-6 (1998)).

The term "apelin," indicates a 77 residue preprotein (NCBI Reference Sequence: NP_0059109.3, and encoded by NCBI Reference Sequence: NM_017413.3), which gets processed into biologically active forms of apelin peptides, such as apelin-36, apelin-17, apelin-16, apelin-13, apelin-12. The full length mature peptide, referred to as "apelin-36," comprises 36 amino acids, but the most potent isoform is the pyroglutamated form of a 13 mer of apelin (apelin-13), referred to as "Pyr-1-apelin-13 or Pyr$^1$-apelin-13" Different apelin forms are described, for instance, in U.S. Pat. No. 6,492,324B1.

Polypeptides of the Invention:

Various embodiments of the invention are described herein. It will be recognized that features specified in each embodiment may be combined with other specified features to provide further embodiments.

In embodiment 1, the invention therefore provides a peptide or a polypeptide formula (I'):

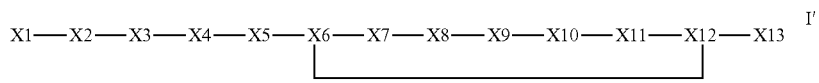

wherein:
X1 is the N-terminus of the polypeptide and is either absent or is selected from pE, R, Isn, Q, A, K, and 5-aminovaleric acid;
X2 is R, A, r, N-Me-R, K, H, hF, hK, F, E or Orn;
X3 is P, A, a, p, 4-PhP, K, D, pipecolic acid, or cysteine wherein the side chain of cysteine forms a disulfide bond with the side chain of the cysteine at the X7 position;
X4 is R, A, r, N-Me-R, F, E or cysteine wherein the side chain of cysteine forms a disulfide bond with the side chain of the cysteine at the X7 position;

X5 is L, Cha, A, D-L, N-Me-L, K, D, 4-PhF or F;
X6 and X12 are independently a natural or unnatural amino acid selected from C, c, hC, D-hC, K, D, Orn, Dab or E wherein the side chain of X6 and X12 are linked together via a covalent bond forming either a disulfide or an amide bond;
or alternatively X6 is K, X13 is absent and X12 is F or f wherein the C-terminus of X12 form an amide bond with the amino side chain of X6;
X7 is H, h, A, N-Me-A, a, Aib, K, Nal, F, P, Dap, N, E or cysteine wherein the side chain of the cysteine forms a disulfide bond with the side chain of the cysteine at position X3 or with the side chain of the cysteine at position X4;
X8 is K, k, F, f, A, hF, N-Me-R, E or 4-amino-Isn;
X9 is G, N-Me-G, A, D, L, R or Aib;
X10 is P, A, p, 4-PhP or pipecolic acid,
X11 is M, D-Nle, Nle, N-Me-Nle, M(O), A, F, Y, L, K, 3-PyA or Cha; and
X13 is the C-terminus and is absent or is selected from F, f, N-Me-F, Nal, D-Nal, 3-Br—F, (S)-β3-F, I, A, a, K, Dap, H and E; wherein:
Nle is L-norleucine;
D-hC is D-homocysteine
hC is L-homocysteine;
hF is L-homophenylalanine;
hK is L-lysine;
Nal is L-naphathaline;
Orn is ornithine;
Aib is α-aminoisobutyric acid;
Dab is (S)-diaminobutyric acid;
Dap is (S)-2,3-diaminopropionic acid;
M(O) is methionine sulfone;
Cha is (S)-β-cyclohexylalanine;
4-amino-Isn is 4-aminopiperidine-4-carboxylic acid;
Isn is isonipecotinoyl;
pE is L-pyroglutamic acid;
3-PyA is 3-(3-pyridyl)-L-alanine;
4-PhF is 4-Phenyl-L-phenylalanine;
wherein the N-terminus and the C-terminus optionally form a ring together with 1, 2, 3 or 4 glycine amino acids; and
wherein the amino group in the side chain of K, Orn, Dab, Dap, hK or 4-amino-Isn is optionally linked to a lipophilic group via an amide bond;
or an amide, an ester or a salt of the polypeptide; or a polypeptide substantially equivalent thereto.

In embodiment 2, the invention therefore provides a peptide or a polypeptide formula (I):

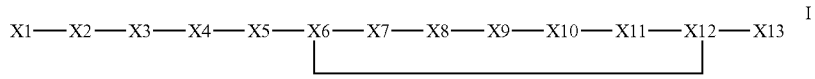

wherein:
X1 is the N-terminus of the polypeptide and is either absent or is selected from pE, R, Q, A, K, 5-amino-valeric acid and Isn;
X2 is R, A, r, N-Me-R, K, H, hF, hK or Orn;
X3 is P, A, a, p, 4-PhP, pipecolic acid, or cysteine wherein the side chain of cysteine forms a disulfide bond with the side chain of the cysteine at the X7 position;
X4 is R, A, r, N-Me-R or cysteine wherein the side chain of cysteine form a disulfide bond with the side chain of the cysteine at the X7 position;
X5 is L, Cha, A, D-L, N-Me-L or F;

X6 and X12 are independently a natural or unnatural amino acid selected from C, c, hC, D-hC, K, D, Orn, Dab or E wherein the side chain of X6 and X12 are linked together via a covalent bond;
or alternatively X6 is K, X13 is absent and X12 is F or f wherein the C-terminus of X12 form an amide bond with the amino side chain of X6;
X7 is H, h, A, N-Me-A, a, Aib, K, Nal, F, P, Dap, N or cysteine wherein the side chain of the cysteine form a disulfide bond with the side chain of the cysteine at position X3 or with the side chain of the cysteine at position X4;
X8 is K, k, F, f, A, hF, N-Me-R or 4-amino-Isn;
X9 is G, N-Me-G, A or Aib;
X10 is P, A, p, 4-PhP or pipecolic acid,
X11 is M, D-Nle, Nle, N-Me-Nle, M(O), A, F, Y, L, K or Cha; and
X13 is the C-terminus and is absent or is selected from F, f, N-Me-F, Nal, D-Nal, 3-Br—F, (S)-β-3-F, I, A, a, K, Dap
wherein:
Nle is L-norleucine;
D-hC is D-homocysteine
hC is L-homocysteine;
hF is L-homophenylalanine;
hK is L-lysine;
Nal is L-naphathaline;
Orn is ornithine;
Aib is α-aminoisobutyric acid;
Dab is (S)-diaminobutyric acid;
Dap is (S)-2,3-diaminopropionic acid;
M(O) is methionine sulfone;
Cha is (S)-β-cyclohexylalanine;
4-amino-Isn is 4-Aminopiperidine-4-carboxylic acid;
Isn is isonipecotinoyl;
pE is L-pyroglutamic acid;
wherein the N-terminus and the C-terminus optionally form a ring together with 1, 2, 3 or 4 glycine amino acids; and
wherein the amino group in the side chain of K, Orn, Dab, Dap, hK or 4-amino-Isn is optionally linked to a lipophilic group via an amide bond;
or an amide, an ester or a salt of the polypeptide; or a polypeptide substantially equivalent thereto.

In one aspect of embodiment 1 or 2, the invention pertains to peptide or polypeptide of Formula I or I' wherein the amino group in the side chain of K, Orn, Dab, Dap, hK or 4-amino-Isn is optionally linked to a fatty acid via an amide bond. In a further aspect of this embodiment, the fatty acid is selected from Lauroyl, Myristoyl or Palmitoyl, wherein Lauroyl is $C_{11}H_{23}C(O)-$, Myristoyl is $C_{13}H_{27}C(O)-$ and Palmitoyl is $C_{15}H_{31}C(O)-$. Alternatively the terminal $CH_3$ moiety of the fatty acid (such as Lauroyl, Myristoyl or Palmitoyl) may be oxidized to its corresponding carboxylic acid.

In one aspect of embodiment 1 or 2, the invention pertains to peptide or polypeptide of Formula I or I' wherein the amino group in the side chain of K, Orn, Dab, Dap, hK or 4-amino-Isn is optionally linked to a lipophilic group via an amide bond, wherein the lipophilic group is selected from a fatty acid as decribed supra and Lauroyl(O2Oc), Myristoyl (O2Oc) and palmitoyl(O2Oc) and wherein Lauroyl(O2Oc)

is C₁₁H₂₃C(O)NH—(CH₂)₂—O—(CH₂)₂—O—CH₂C(O)—; Myristoyl(O2Oc) is C₁₃H₂₇C(O)NH—(CH₂)₂—O—(CH₂)₂—O—CH₂C(O)—; palmitoyl(O2Oc) is C₁₅H₃₁C(O)NH—(CH₂)₂—O—(CH₂)₂—O—CH₂C(O)—.

Alternatively the terminal CH₃ moiety of the fatty acid (such as Lauroyl, Myristoyl or Palmitoyl) may be oxidized to its corresponding carboxylic acid.

In embodiment 3, the invention pertains to a peptide or polypeptide of Formula I or I':

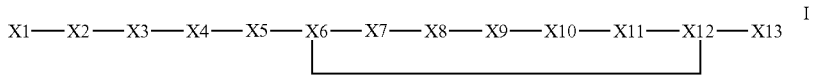

wherein:
X1 is the N-terminus of the polypeptide and is either absent or is selected from pE, R, Q, A, K(palmitoyl), K(Myristoyl), K(Lauroyl), 5-amino-valeric acid and Isn;
X2 is R, A, r, N-Me-R, K, H, hF, hK or Orn;
X3 is P, A, a, p, 4-PhP, pipecolic acid, or cysteine wherein the side chain of cysteine forms a disulfide bond with the side chain of the cysteine at the X7 position;
X4 is R, A, r, N-Me-R or cysteine wherein the side chain of cysteine form a disulfide bond with the side chain of the cysteine at the X7 position;
X5 is L, Cha, A, D-L, N-Me-L or F;
X6 and X12 are independently a natural or unnatural amino acid selected from C, c, hC, D-hC, K, D, Orn, Dab or E wherein the side chain of X6 and X12 are linked together via a covalent bond;
or alternatively X6 is K, X13 is absent and X12 is F or f wherein the C-terminus of X12 form an amide bond with the amino side chain of X6;
X7 is H, h, A, N-Me-A, a, Aib, K(Lauroyl), K(Palmitoyl), Nal, F, P, Dap, N or cysteine wherein the side chain of the cysteine form a disulfide bond with the side chain of the cysteine at position X3 or with the side chain of the cysteine at position X4;
X8 is K, k, F, f, A, hF, N-Me-R or 4-amino-Isn;
X9 is G, N-Me-G, A or Aib;
X10 is P, A, p, 4-PhP or pipecolic acid,
X11 is M, D-Nle, Nle, N-Me-Nle, M(O), A, F, Y, L, K(Palmitoyl) or Cha; and
X13 is the C-terminus and is absent or is selected from F, f, N-Me-F, Nal, D-Nal, 3-Br—F, (S)-β-3-F, I, A, a, K(Lauroyl), K(Myristoyl), K(palmitoyl), K(O2Oc-Palmitoyl), Dap(Palmitoyl);
wherein:
K(Lauroyl) is N-ε-lauroyl-L-lysine;
K(palmitoyl) is N-ε-palmitoyl-L-lysine;
K(Myristoyl) is N-ε-myristoyl-L-lysine;
K(O2Oc-Palmitoyl) is N-ε-(O2Oc-Palmitoyl)-L-lysine; and
Palmitoyl(O2Oc) is C₁₅H₃₁C(O)NH—(CH₂)₂—O—(CH₂)₂—O—CH₂—O—C(O)—;
Nle is L-norleucine;
D-hC is D-homocysteine
hC is L-homocysteine;
hF is L-homophenylalanine;
hK is L-lysine;
Nal is L-naphathaline;
Orn is ornithine;
Aib is α-aminoisobutyric acid;
Dab is (S)-diaminobutyric acid;
Dap is (S)-2,3-diaminopropionic acid;
M(O) is methionine sulfone;
Cha is (S)-β-cyclohexylalanine;
4-amino-Isn is 4-Aminopiperidine-4-carboxylic acid;
Isn is isonipecotinoyl;
pE is L-pyroglutamic acid;
and wherein the N-terminus and the C-terminus optionally form a ring together with 1, 2, 3 or 4 glycine amino acids;
or an amide, an ester or a salt of the polypeptide.

In embodiment 4, the invention pertains to a peptide or a polypeptide according to embodiment 1, 2 or 3, having Formula II (SEQ ID NO: 1):

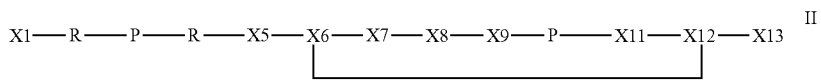

X1 is absent, pE, R, Q or Isn;
X5 is L or Cha;
X7 is H, Aib, F, K(Lauroyl) or K(palmitoyl);
X8 is K, F or 4-amino-Isn;
X9 is G or Aib;
X11 is Nle or Cha;
X13 is absent or is F, f, K(Lauroyl), K(palmitoyl);
X6 and X12 are independently a natural or unnatural amino acid selected from C, c, hC, D-hC, K, D, Orn, Dab or E wherein the side chain of X6 and X12 are linked together via a covalent bond; or alternatively X6 is K, X13 is absent and X12 is F or f wherein the C-terminus of X12 form an amide bond with the amino side chain of X6; and wherein the N-terminus and the C-terminus optionally form a ring together with 1, 2, 3 or 4 glycine amino acids; or an amide, an ester or a salt of the polypeptide; or a polypeptide substantially equivalent thereto.

In embodiment 5, the invention pertains to a peptide or a polypeptide according to embodiment 4 wherein:

X1 is absent, pE, R, Q or Isn;
X5 is L or Cha;
X7 is H, Aib, F, K(Lauroyl) or K(palmitoyl);
X8 is K, F or 4-amino-Isn;
X9 is G or Aib;
X11 is Nle or Cha;
X13 is absent or is F, f, K(Lauroyl), K(palmitoyl);
X6 and X12 are independently a natural or unnatural amino acid selected from C, K, D, Orn, Dab or E wherein the side chain of X6 and X12 are linked together via a covalent bond; or
alternatively X6 is K, X13 is absent and X12 is F or f wherein the C-terminus of X12 form an amide bond with the amino side chain of X6; and
wherein the N-terminus and the C-terminus optionally form a ring together with 1, 2, 3 or 4 glycine amino acids; or an amide, an ester or a salt of the polypeptide; or a polypeptide substantially equivalent thereto.

In embodiment 6, a further aspect of embodiment 4, the invention pertains to a peptide or polypetide of Formula II wherein:
X1 is absent, pE, R, Q or Isn;
X5 is L or Cha;
X7 is H, Aib, F, K(Lauroyl) or K(palmitoyl);
X8 is K, F or 4-amino-Isn;
X9 is G or Aib;
X11 is Nle or Cha;
X13 is absent or is F, f, K(Lauroyl), K(palmitoyl);
X6 and X12 are independently a natural or unnatural amino acid selected from C, c, hC, D-hC, K, D, Orn, Dab or E wherein the side chain of X6 and X12 are linked together via a covalent bond; and wherein the N-terminus and the C-terminus optionally form a ring together with 1, 2, 3 or 4 glycine amino acids; or an amide, an ester or a salt of the polypeptide; or a polypeptide substantially equivalent thereto.

In yet a further aspect of anyone of the previous embodiments, more specifically of anyone of embodiments 1 to 6, the invention pertains to peptide and polypeptide of Formula I, I' or II wherein X6 and X12 are independently a natural or unnatural amino acid selected from C, K, D, Orn, Dab or E wherein the side chain of X6 and X12 are linked together via a covalent bond; or an amide, an ester or a salt of the polypeptide; or a polypeptide substantially equivalent thereto.

In embodiment 7, the invention pertains to a peptide or polypeptide of Formula I, I' or II, according to anyone of the previous embodiments, more specifically of anyone of embodiments 1 to 6, wherein X6 and X12 are independently selected from K, Orn, Dab, E and D and wherein the side chain of X6 and X12 form together an amide bond; or an amide, an ester or a salt of the peptide or polypeptide. In a further aspect of this embodiment, X6 is K, Orn or Dab and X12 is E or D and the side chain of X6 and X12 form an amide bond. In yet another aspect of this embodiment, X6 is K and X12 is E or D.

In embodiment 8, the invention pertains to a peptide or polypeptide of Formula I, I' or II, according to anyone of the previous embodiments, more specifically of anyone of embodiments 1 to 6, wherein X6 and X12 are independently C, c, D-hC or hC wherein the side chain of X6 and X12 form together a disulfide bond; or an amide, an ester or a salt of the peptide or polypeptide. In a further aspect of this embodiment, X6 and X12 are C.

In embodiment 8A, the invention pertains to a peptide or polypeptide of Formula I, I' or II, according to anyone of the previous embodiments, more specifically of anyone of embodiments 1 to 6, wherein X6 and X12 are independently C, c, D-hC or hC wherein the side chain of X6 and X12 form together a monosulfide (—S—) bond; or an amide, an ester or a salt of the peptide or polypeptide. In a further aspect of this embodiment, X6 and X12 are C.

In embodiment 8B, the invention pertains to a peptide or polypeptide of Formula I, I' or II, according to anyone of the previous embodiments, more specifically of anyone of embodiments 1 to 6, wherein X6 and X12 are independently C, c, D-hC or hC wherein the side chain of X6 and X12 form together a linkage moiety of Formula —S—CH$_2$—C(=Z)—CH$_2$—S—; wherein =Z is =O, =N—O—CH$_2$C(O)-L$^1$-R$^1$ or =N—NH—CH$_2$C(O)-L$^1$-R$^1$ wherein R$^1$ is a fatty acid derivative and L$^1$ is a linker containing one or more amino acids and/or one or more —NH—C$_{2-6}$-alkylene-NH— units; or an amide, an ester or a salt of the peptide or polypeptide. In a further aspect of this embodiment, X6 and X12 are C.

L1 is a suitable organic linker that connects a fatty acid derivative to the polypeptide via an ester or an amide bond. Typically the linker contains one or more amino acid moieties such as for example (O2Oc) unit or Glutamic acid, or contains —NH—C$_{2-6}$alkylene-NH— diamino units or combination thereof. R$^1$ is a property-modifying group such as fatty acid derivative which can be added to increase the half-life of the polypeptide. In one aspect of this embodiment, R1 is a fatty acid of Formula C$_q$H$_{q+1}$C(O)$_2$H wherein q is 3 to 20. Optionally the terminal CH$_3$ unit may be oxidized to its corresponding carboxylic acid.

In one particular embodiment, -L$^1$-R$^1$ is of Formula:

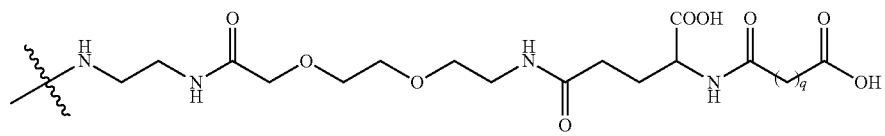

q is an integer of 3 to 20. Preferably, q is an integer of 12 to 18.

A peptide or polypeptide of Formula I, I' or II wherein X6 and X12 are independently C, c, D-hC or hC wherein the side chain of X6 and X12 form together a linkage moiety of Formula —S—$CH_2$—C(=Z)—$CH_2$—S—; wherein =Z is =O, =N—O—$CH_2$C(O)-$L^1$-$R^1$ or =N—NH—$CH_2$C(O)-$L^1$-$R^1$ can be synthesized according to Scheme 1:

Scheme 1

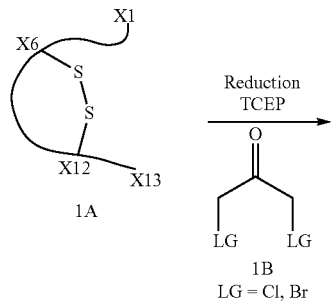

1A

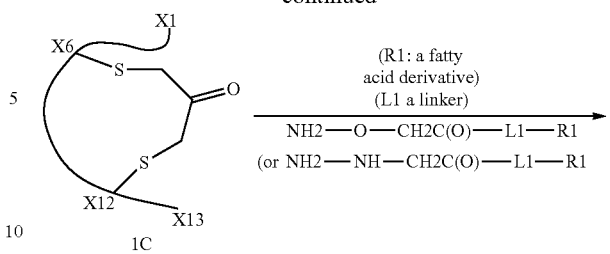

1C

Reduction of the polypeptide disulfide bond in (1A) is followed by a nucleophilic reaction di-electrophilic compound (1B) forming polypeptide (1C). The ketone functionality of the polypeptide (1C) condensed readily with an oxiamine or hydrazine to generate polypeptide 1D.

In embodiment 9, certain polypeptides of the invention include peptides or polypeptides according to anyone of embodiment 1 to 6 and 8, having Formula III (SEQ ID NO: 2):

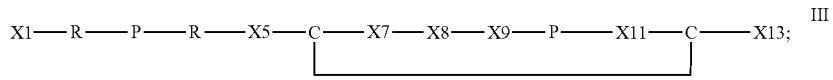

or an amide, an ester or a salt of the polypeptide. In embodiment 9A, the invention pertains to peptides and polypeptides of Formula III wherein the 2 cysteine at position 6 and 12 form a disulfide bond (—S—S—), a monosulfide bond (—S—) or a linkage of Formula —S—$CH_2$—C(=Z)—$CH_2$—S— wherein Z is as defined supra. In a further aspect of embodiment 9 or 9A, the invention includes peptides or polypeptides of Formula III wherein the 2 cysteines in position 6 and 12 form a disulfide bond (—S—S—).

In embodiment 10, certain peptides and polypeptides of the invention include peptides and polypeptides according to anyone of embodiment 1-9 having Formula IV (SEQ ID NO: 3):

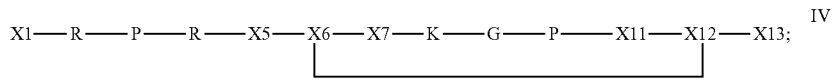

or an amide, an ester or a salt of the polypeptide.

In embodiment 11, certain polypeptides of the invention include polypeptides according to anyone of embodiment 1-6, and 8-10, having Formula V (SEQ ID NO: 4):

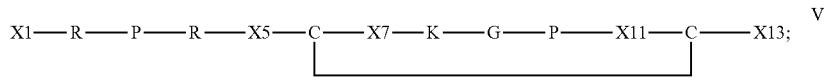

or an amide, an ester or a salt of the polypeptide. In embodiment 11A, the invention pertains to peptides and polypeptides of Formula V wherein the 2 cysteine at position 6 and 12 form a disulfide bond (—S—S—), a monosulfide bond (—S—) or a linkage of Formula —S—CH$_2$—C(=Z)—CH$_2$—S— wherein Z is as defined supra. In a further aspect of embodiment 11 or 11A, the invention includes peptides or polypeptides of Formula V wherein the 2 cysteines in position 6 and 12 form a disulfide bond (—S—S—).

In embodiment 12, the invention pertains to bicyclic peptides or polypeptides of Formula I or I' (according to embodiment 1, 2 or 3) wherein X3 is cysteine and wherein the side chain of cysteine forms a disulfide bond with the side chain of the cysteine at the X7 position. This embodiment is represented by peptides and polypeptides of Formula VI (SEQ ID NO: 5):

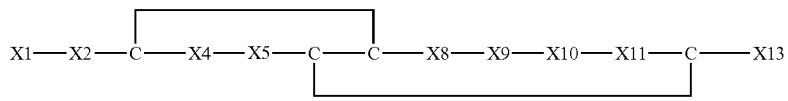

or an amide, an ester or a salt of the polypeptide.

In embodiment 13, the invention pertains to bicyclic peptides or polypeptides of Formula I or I' (according to embodiment 1, 2 or 3) wherein X4 is cysteine and wherein the side chain of cysteine forms a disulfide bond with the side chain of the cysteine at the X7 position. This embodiment is represented by peptides and polypeptides of Formula VII (SEQ ID NO: 6):

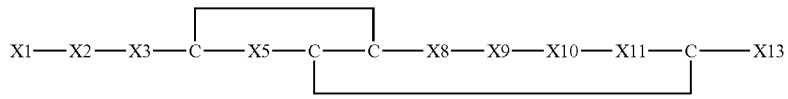

or an amide, an ester or a salt of the polypeptide.

In embodiment 14, the invention pertains to a peptide or polypeptide of anyone of Formulae I to V, according to anyone of embodiment 1 to 11; wherein the N-terminus and the C-terminus optionally form a ring together with 1, 2, 3 or 4 glycine amino acids; or an amide, an ester or a salt of the polypeptide; or a polypeptide substantially equivalent thereto. This embodiment is represented by peptide or polypeptide having Formula VIII:

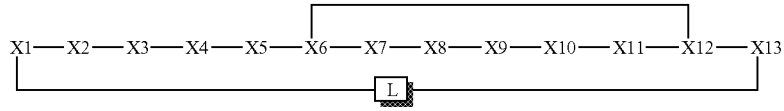

wherein L is (G)r, G is glycine and r is 1, 2, 3 or 4; or a salt of the polypeptide.

In embodiment 15, a further aspect of embodiment 14, the invention pertains to peptide or polypeptide of Formula VIII wherein X1 is Q, X13 is F and r is 2 or an ester, an amide or a salt thereof.

In embodiment 16, the invention pertains to a peptide or polypeptide according to Formula I or I', according to embodiment 1, 2 or 3, wherein X6 is K, X13 is absent and X12 is F or f wherein the C-terminus of X12 forms an amide bond with the amino side chain of X6. This embodiment is represented by a peptide or polypeptide of Formula IX:

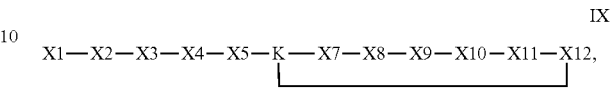

or an ester, an amide or a salt of the polypeptide.

Any of the or below above-listed amino acid residues of Formula I', or its related formulae and all embodiments described herein, e.g., Formulae I, II to IX, may be substituted in a conservative fashion, provided the peptide or polypeptide of the invention still retains functional activity and structural properties (e.g., half-life extension, protection from degradation, conformational constraint). Principle and examples of permissible conservative amino acid substitutions are further explained herein.

The following embodiments can be used independently, collectively or in any combination or sub-combination:

In embodiment 17, the invention pertains to peptides and polypeptides according to any one of Formulae I', I to VII and IX, or any of any other classes and subclasses described supra, (i.e. according to anyone of the embodiments 1 to 13 and 16) or an amide, an ester or a salt thereof, wherein X1 is pE.

In embodiment 18, the invention pertains to peptides and polypeptides according to any one of Formulae I to VII and IX, or any of any other classes and subclasses described supra, (i.e. according to anyone of the embodiments 1 to 13 and 16) or an amide, an ester or a salt thereof, wherein X1 is absent; or an amide, an ester or a salt of the polypeptide. In one aspect of this embodiment, the N-terminus of the peptide is an amide. In embodiment 19, a further aspect of embodiment 18, the invention pertains to peptides and polypeptide according to any one of Formulae I to VII and IX, or any of any other classes and subclasses described supra, or an amide, an ester or a salt thereof, wherein the X1 is absent and the N-terminus is an amide of Formula —NHR and R is CH₃C(O)—, CH₃—(O—CH₂CH₂)ₘ—C(O)—, Palmitoyl(O2Oc)ₚ, Myristoyl(O2Oc)ₚ, Lauroyl(O2Oc)ₚ or Ph-CH₂CH₂NHC(O)—, Acetyl, benzoyl, phenacyl, succinyl, octanoyl, 4-phenylbutanoyl, 4-Cl-Ph-(CH2)₃C(O)—, or Ph-CH₂CH₂NHC(O)—; and wherein p is an integer 1 to 4;
m is an integer 1 to 12;
Lauroyl(O2Oc)ₚ is C₁₁H₂₃C(O)[NH—(CH₂)₂—O—(CH₂)₂—O—CH₂—C(O)]ₚ—;
Myristoyl(O2Oc)ₚ is C₁₃H₂₇C(O)[NH—(CH₂)₂—O—(CH₂)₂—O—CH₂—C(O)]ₚ—;
Palmitoyl(O2Oc)ₚ is C₁₅H₃₁C(O)[NH—(CH₂)₂—O—(CH₂)₂—O—CH₂—C(O)]ₚ—. In one particular aspect of this embodiment R is Acetyl, benzoyl, phenacyl, succinyl, octanoyl, 4-phenylbutanoyl, 4-Cl-Ph-(CH2)3C(O)—, or Ph-CH₂CH₂NHC(O)—.

In embodiment 20, the invention pertains to peptide or polypeptide according to anyone of Formulae I to VII and IX, or any other classes and subclasses described supra, (i.e. according to anyone of embodiments 1-13 and 16), or an amide, an ester or a salt thereof, wherein N-terminus is an amide of Formula NHR1 wherein R1 is CH₃C(O)—, CH₃—(O—CH₂CH₂)ₘ—C(O)—, Palmitoyl(O2Oc), Myristoyl (O2Oc), Lauroyl(020c) or Ph-CH₂CH₂NHC(O)—; and wherein m, Lauroyl(020c), Myristoyl(020c) and Palmitoyl (O2Oc) are defined supra.

In embodiment 21, the invention pertains to peptides and polypeptides according to any one of Formulae I to VII, or any of any other classes and subclasses described supra, (i.e. according to anyone of embodiments 1 to 13), or an amide, an ester or a salt thereof, wherein X13 is F; or an amide, an ester or a salt of the polypeptide.

In embodiment 22, the invention pertains to peptides and polypeptides according to any one of Formulae I to VII, or any of any other classes and subclasses described supra, (i.e. according to anyone of embodiments 1 to 13), or an amide, an ester or a salt thereof, wherein X13 is absent; or an amide, an ester or a salt of the polypeptide. In embodiment 23, one aspect of embodiment 22, The C-terminus is an amide. In embodiment 24, a further aspect of embodiment 23, the invention pertains to peptides and polypeptide according to any one of Formulae I to VII, or any of any other classes and subclasses described supra, or an amide, an ester or a salt thereof, wherein the C-terminus is an amide of Formula —C(O)R2 and R2 is —NH₂, —NH-Me, —NH—NHBn, or —NH—(CH₂)₂-Ph. In a prefered aspect of embodiment 23, the invention pertains to peptides and polypeptide according to any one of Formulae I to VII, or any of any other classes and subclasses described supra, or an amide, an ester or a salt thereof, wherein the C-terminus is an amide of Formula —C(O)R2 and R2 is —NH—(CH₂)₂-Ph.

In embodiment 25, the invention pertains to peptides and polypeptides according to anyone of Formulae I to IX, or any of any other classes and subclasses described supra, (i.e. according to anyone of embodiments 1 to 25), or an amide, an ester or a salt thereof, wherein X5 is L.

In embodiment 26, the invention pertains to peptides and polypeptides according to anyone of Formulae I to V, VIII and IX, or any of any other classes and subclasses described supra (i.e. according to anyone of embodiments 1 to 11 and 14-25), or an amide, an ester or a salt thereof, wherein X7 is H.

In embodiment 27, the invention pertains to peptides and polypeptides according to anyone of Formulae I to III and VI to IX, or any of any other classes and subclasses described supra, (i.e. according to anyone of embodiments 1 to 9 and 12 to 26), or an amide, an ester or a salt thereof, wherein X8 is K or F. In a further aspect of this embodiment, X8 is K.

In embodiment 28, the invention pertains to peptides and polypeptides according to any one of Formulae I to III and VI to IX, or any of any other classes and subclasses described supra, (i.e. according to anyone of embodiments 1 to 9 and 12 to 27) or an amide, an ester or a salt thereof, wherein X9 is G.

In embodiment 29, the invention pertains to peptides and polypeptides according to any one of Formulae I to IX, or any of any other classes and subclasses described supra, (i.e. according to anyone of embodiments 1 to 28), or an amide, an ester or a salt thereof, wherein X11 is Nle.

In embodiment 30, the invention therefore provides a peptide or a polypeptide formula (I'):

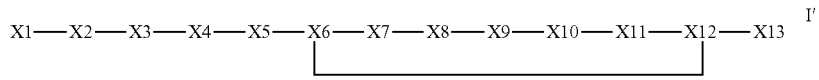

wherein:
X1 is the N-terminus of the polypeptide and is either absent or is selected from pE, R, Isn and Q;
X2 is R, r, F or E;
X3 is P, p, K, D or 4-Ph F; or cysteine wherein the side chain of cysteine forms a disulfide bond with the side chain of the cysteine at the X7 position;
X4 is R, F, E or cysteine wherein the side chain of cysteine forms a disulfide bond with the side chain of the cysteine at the X7 position;
X5 is L, K, D or 4-PhF;
X6 and X12 are independently a natural or unnatural amino acid selected from C, c, hC, D-hC, K, D, Orn, Dab or E wherein the side chain of X6 and X12 are linked together via a covalent bond forming either a disulfide or an amide bond;
or alternatively X6 is K, X13 is absent and X12 is F or f wherein the C-terminus of X12 form an amide bond with the amino side chain of X6;
X7 is H, Aib, K, E, F or cysteine wherein the side chain of the cysteine forms a disulfide bond with the side chain of the cysteine at position X3 or with the side chain of the cysteine at position X4;
X8 is K, E, F or 4-amino-Isn;
X9 is G, D, L, R or Aib;
X10 is P or pipecolic acid,
X11 is Nle or 3-PyA; and
X13 is the C-terminus and is absent or is selected from F, f, K, H and E;
wherein the N-terminus and the C-terminus optionally form a ring together with 1, 2, 3 or 4 glycine amino acids; and
wherein the amino group in the side chain of K, Orn, Dab, Dap, hK or 4-amino-Isn is optionally linked to a lipophilic group via an amide bond;

or an amide, an ester or a salt of the polypeptide; or a polypeptide substantially equivalent thereto.

In embodiment 31, the invention pertains to a peptide or polypeptide of embodiment 1, 2 or 3, wherein three of the amino acids X1 to X13 are different from the corresponding amino acids present in Pyr-1-apelin-13. In embodiment 32, the invention pertains to a peptide or polypeptide of embodiment 1, 2 or 3 wherein four of the amino acids X1 to X13 are different from the corresponding amino acids present in Pyr-1-apelin-13.

In another embodiment, X1, X2, X3, X4, X5, X6, X7, X8. X9, X10, X11, X12 and X13 amino acids are those defined by X1, X2, X3, X4, X5, X6, X7, X8. X9, X10, X11, X12 and X13 amino acids in the Examples section below.

In another embodiment, individual polypeptides according to the invention are those listed in the Examples section below or a pharmaceutically acceptable salt thereof.

Unless specified otherwise, the term "polypeptide of the present invention" refers to a polypeptide of Formula (I') and subformulae thereof (Formulae I, II to IX); or an amide, an ester or a salt thereof.

Unless specified otherwise, the terms "polypeptides of the present invention," "peptides of the present invention," "apelin peptide agonists," and the like refer to peptides and polypeptides of Formula I' and subformulae thereof (Formulae I, II, III, IV, V, VI, VII, VIII or IX); or an amide, an ester or a salt thereof. The peptides and polypeptides of the invention demonstrate substantially equivalent or improved activity and/or plasma stability over known apelin peptides and polypeptides described herein, including but not limited to wild type apelin, apelin-13 and pyr-1-apelin-13.

The peptides and polypeptides of the invention also encompass peptides and polypeptides that are at least about 95% identical to the peptides and polypeptides according to any one of Formulae I', I to IX, or an amide, an ester or a salt thereof, as well as to any peptides or polypeptides specifically listed herein, including but not limited to the experimental examples.

As used herein, the phrase "homologous amino acid sequence," or variations thereof, refers to sequences characterized by a homology, at the amino acid level, of at least a specified percentage and is used interchangeably with "sequence identity." Homologous amino acid sequences include those amino acid sequences which contain conservative amino acid substitutions and which polypeptides have the same binding and/or activity. In some embodiments, an amino acid sequence is homologous if it has at least 60% or greater, up to 99%, identity with a comparator sequence. In some embodiments, an amino acid sequence is homologous if it shares one or more, up to 60, amino acid substitutions, additions, or deletions with a comparator sequence. In some embodiments, the homologous amino acid sequences have no more than 5 or no more than 3 conservative amino acid substitutions.

Homology may also be at the polypeptide level. The degree or percentage identity of peptides or polypeptides of the invention, or portions thereof, and different amino acid sequences is calculated as the number of exact matches in an alignment of the two sequences divided by the length of the "invention sequence" or the "foreign sequence", whichever is shortest. The result is expressed as percent identity.

A polypeptide comprising an amino acid sequence having a homology of about 80-99.9%, preferably 90-99.9% to the amino acid sequence described in the specific examples, and possessing a plasma stability superior to apelin-13 or pyr-1-apelin-13, fall under the category of the polypeptide of the invention. In one embodiment, the plasma stability improvement is at least 2 fold. In one embodiment, the polypeptide of the invention has a plasma stability of at least 30 minutes. In another embodiment, the polypeptide of the invention has a plasma stability of at least 60 minutes, preferably at least 100 min and more preferably at least 150 minutes.

The term "substantially equivalent" means the nature of the receptor-binding activity, signal transduction activity and the like is equivalent. Thus, it is allowable that even differences among grades such as the strength of receptor binding activity and the molecular weight of the polypeptide are present.

A polypeptide as described herein, or a substantial equivalent thereto, by substitution, deletion, addition or insertion of one or more of amino acids may be mentioned as polypeptides containing an amino acid sequence substantial equivalent(s) in the above sense. A polypeptide as described herein, or a substantial equivalent thereto, by substitution of 1 to 5, preferably 1 to 3 and more preferably 1 or 2 amino acids with natural or un-natural amino acids may be mentioned as polypeptides containing an amino acid sequence substantial equivalent(s) in the above sense. Further modifications and alterations may include the replacement of an L-amino-acid with a D-amino acid, or other variation including, but not limited to, phosphorylation, carboxylation, alkylation and the like as long as the apelin agonistic activity of the peptide of polypeptide of Formulae I, II, III, IV, V, VI, VII, VIII or IX is maintained and the plasma stability is improved over the pyroglutamated form of apelin-13. For example, D-amino acid are well tolerated with respect to activity and stability of the polypeptide at position 2 (X2), position 3 (X3), positions 5, 6, 7 and 8 (X5, X6, X7 and X8), position 10 (X10) and position 13 (X13) of the cyclic peptides and polypeptides of Formulae I, II, III, IV, V, VI, VII, VIII or IX.

As used herein, the term "pharmaceutically acceptable salts" refers to salts that retain the biological effectiveness and properties of the polypeptides of this invention and, which typically are not biologically or otherwise undesirable. In many cases, the polypeptides of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfornate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a polypeptide of the present invention refers to an amount of the polypeptide of the present invention that will elicit the biological or medical response of a subject, for example, amelioration of a symptom, alleviation of a condition, slow or delay disease progression, or prevention of a disease, etc. In one non-limiting embodiment, the term "a therapeutically effective amount" refers to the amount of the polypeptide of the present invention that, when administered to a subject, is effective to (1) at least partially alleviate, inhibit, prevent and/or ameliorate a condition, a disorder or a disease or a symptom thereof (i) ameliorated by the activation of the APJ receptor or (ii) associated with the activity of the APJ receptor, or (iii) characterized by abnormal activity of the APJ receptor; or (2) activate the APJ receptor.

In another non-limiting embodiment, the term "a therapeutically effective amount" refers to the amount of the polypeptide of the present invention that, when administered to a cell, or a tissue, or a non-cellular biological material, or a medium, is effective to at least partially activate the APJ receptor. As will be appreciated by those of ordinary skill in the art, the absolute amount of a particular agent that is effective may vary depending on such factors as the desired biological endpoint, the agent to be delivered, the target tissue, etc. Those of ordinary skill in the art understand that "a therapeutically effective amount" may be administered in a single dose or may be achieved by administration of multiple doses. For example, in the case of an agent to treat heartfailure, an effective amount may be an amount sufficient to result in clinical improvement of the patient, e.g., increased exercise tolerance/capacity, increased blood pressure, decrease fliud retention, and/or improved results on a quantitative test of cardiac functioning, e.g., ejection fraction, exercise capacity (time to exhaustion), etc.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, the terms "prevent", "preventing" and "prevention" refer to the prevention of the recurrence, onset, or development of one or more symptoms of a disorder in a subject resulting from the administration of a therapy (e.g., a therapeutic agent), or the administration ofa combination of therapies (e.g., a combination of therapeutic agents).

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The peptides and polypeptides of the present invention can be produced by the per se known procedures for peptide synthesis. The methods for peptide synthesis may be any of a solid-phase synthesis and a liquid-phase synthesis. Thus, the peptide and polypeptide of interest can be produced by condensing a partial peptide or amino acid capable of constituting the protein with the residual part thereof and, when the product has a protective group, the protective group is detached whereupon a desired peptide can be manufactured. The known methods for condensation and deprotection include the procedures described in the following literature (1)-(5).

(1) M. Bodanszky and M. A. Ondetti, Peptide Synthesis, Interscience Publishers, New York, 1966,
(2) Schroeder and Luebke, The Peptide, Academic Press, New York, 1965,
(3) Nobuo Izumiya et al. Fundamentals and Experiments in Peptide Synthesis, Maruzen, 1975,
(4) Haruaki Yajima and Shumpei Sakakibara, Biochemical Experiment Series 1, Protein Chemistry IV, 205, 1977, and
(5) Haruaki Yajima (ed.), Development of Drugs-Continued, 14, Peptide Synthesis, Hirokawa Shoten.

After the reaction, the peptide can be purified and isolated by a combination of conventional purification techniques such as solvent extraction, column chromatography, liquid chromatography, and recrystallization. Where the peptide isolated as above is a free compound, it can be converted to a suitable salt by the known method. Conversely where the isolated product is a salt, it can be converted to the free peptide by the known method.

The amide of polypeptide can be obtained by using a resin for peptide synthesis which is suited for amidation. The resin includes chloromethyl resin, hydroxymethyl resin, benzhydrylamine resin, aminomethyl resin, 4-benzyloxybenzyl alcohol resin, 4-methylbenz-hydrylamine resin, PAM resin, 4-hydroxymethylmethylphenylacetamidomethyl resin, polyacrylamide resin, 4-(2',4'-dimethoxyphenyl-hydroxymethyl)phenoxy resin, 4-(2',4'-dimethoxyphenyl-Fmoc-aminomethyl)phenoxy resin, 2-chlorotrityl chloride resin, and so on. Using such a resin, amino acids whose α-amino groups and functional groups of side-chain have been suitably protected are condensed on the resin according to the sequence of the objective peptide by various condensation techniques which are known per se. At the end of the series of reactions, the peptide or the protected peptide is removed from the resin and the protective groups are removed and if necessary, disulfide bonds are formed to obtain the objective polypeptide.

For the condensation of the above-mentioned protected amino acids, a variety of activating reagents for peptide synthesis can be used such as HATU, HCTU or e.g. a carbodiimide. The carbodiimide includes DCC, N,N'-diisopropylcarbodiimide, and N-ethyl-N'-(3-dimethylaminopropyl)carbodiimide. For activation with such a reagent, a racemization inhibitor additive, e.g. HOBt or Oxyma Pure can be used. The protected amino acid can be directly added to the resin along with the activation reagents and racemization inhibitor or be pre-activated as symmetric acid anhydride, HOBt ester, or HOOBt ester then added to the resin. The solvent for the activation of protected amino acids or condensation with the resin can be properly selected from among those solvents which are known to be useful for peptide condensation reactions. For example, N,N-dimethylformamide, N-methylpyrrolidone, chloroform, trifluoroethanol, dimethyl sulfoxide, DMF, pyridine, dioxane, methylene chloride, tetrahydrofuran, acetonitrile, ethyl acetate, or suitable mixtures of them can be mentioned.

The reaction temperature can be selected from the range hitherto-known to be useful for peptide bond formation and is usually selected from the range of about −20° C.-50° C. The activated amino acid derivative is generally used in a proportion of 1.5-4 fold excess. If the condensation is found to be insufficient by a test utilizing the ninhydrin reaction, the condensation reaction can be repeated to achieve a sufficient condensation without removing the protective group. If repeated condensation still fails to provide a sufficient degree of condensation, the unreacted amino group can be acetylated with acetic anhydride or acetylimidazole.

The protecting group of amino group for the starting material amino acid includes Z, Boc, tertiary-amyloxycarbonyl, isobornyloxycarbonyl, 4-methoxybenzyloxycarbonyl, Cl—Z, Br—Z, adamantyloxycarbonyl, trifluoroacetyl, phthalyl, formyl, 2-nitrophenylsulfenyl, diphenylphosphinothioyl, or Fmoc. The carboxy-protecting group that can be used includes but is not limited to the above-mentioned $C_{1-6}$ alkyl, $C_{3-8}$ cycloalkyl and $C_{6-10}$aryl-$C_{1-2}$alkyl as well as 2-adamantyl, 4-nitrobenzyl, 4-methoxybenzyl, 4-chlorobenzyl, phenacyl, benzyloxycarbonylhydrazido, tertiary-butoxycarbonylhydrazido, and tritylhydrazido.

The hydroxy group of serine and threonine can be protected by esterification or etherification. The group suited for said esterification includes carbon-derived groups such as lower alkanoyl groups, e.g. acetyl etc., aroyl groups, e.g. benzoyl etc., benzyloxycarbonyl, and ethoxycarbonyl. The group suited for said etherification includes benzyl, tetrahydropyranyl, and tertiary-butyl. The protective group for the phenolic hydroxyl group of tyrosine includes Bzl, $Cl_2$-Bzl, 2-nitrobenzyl, Br—Z, and tertiary-butyl.

The protecting group of imidazole for histidine includes Tos, 4-methoxy-2,3,6-tri ethylbenzenesulfonyl, DNP, benzyloxymethyl, Bum, Boc, Trt, and Fmoc.

The activated carboxyl group of the starting amino acid includes the corresponding acid anhydride, azide and active esters, e.g. esters with alcohols such as pentachlorophenol, 2,4,5-trichlorophenol, 2,4-dinitrophenol, cyanomethyl alcohol, p-nitrophenol, HONB, N-hydroxysuccinimide, N-hydroxyphthalimide, HOBt, etc. The activated amino group of the starting amino acid includes the corresponding phosphoramide.

The method for elimination of protective groups includes catalytic reduction using hydrogen gas in the presence of a catalyst such as palladium black or palladium-on-carbon, acid treatment with anhydrous hydrogen fluoride, methanesulfonic acid, trifluoromethanesulfonic acid, trifluoroacetic acid, or a mixture of such acids, base treatment with diisopropylethylamine, triethylamine, piperidine, piperazine, reduction with sodium metal in liquid ammonia. The elimination reaction by the above-mentioned acid treatment is generally carried out at a temperature of −20° C.-40° C. and can be conducted advantageously with addition of a cation acceptor such as anisole, phenol, thioanisole, m-cresol, p-cresol, dimethyl sulfide, 1,4-butanedithiol, 1,2-ethanedithiol. The 2,4-dinitrophenyl group used for protecting the imidazole group of histidine can be eliminated by treatment with thiophenol, while the formyl group used for protecting the indole group of tryptophan can be eliminated by alkali treatment with dilute sodium hydroxide solution or dilute aqueous ammonia as well as the above-mentioned acid treatment in the presence of 1,2-ethanedithiol, 1,4-butanedithiol.

The method for protecting functional groups which should not take part in the reaction of the starting material, the protective groups that can be used, the method of removing the protective groups, and the method of activating the functional groups that are to take part in the reaction can all be selected judicially from among the known groups and methods.

An another method for obtaining the amide form of the polypeptide comprises amidating the -carboxyl group of the C-terminal amino acid at first, then extending the peptide chain to the N-side until the desired chain length, and then selectively deprotecting the α-amino group of the C-terminal peptide and the α-carboxy group of the amino acid or peptide that is to form the remainder of the objective polypeptide and condensing the two fragments whose α-amino group and side-chain functional groups have been protected with suitable protective groups mentioned above in a mixed solvent such as that mentioned hereinbefore. The parameters of this condensation reaction can be the same as described hereinbefore. From the protected peptide obtained by condensation, all the protective groups are removed by the above-described method to thereby provide the desired crude peptide. This crude peptide can be purified by known purification procedures and the main fraction be lyophilized to provide the objective amidated polypeptide. To obtain an ester of the polypeptide, the α-carboxyl group of the C-terminal amino acid is condensed with a desired alcohol to give an amino acid ester and then, the procedure described above for production of the amide is followed.

The polypeptides of the instant invention, or an amide, an ester of a salt thereof, may be administered in any of a variety of ways, including subcutaneously, intramuscularly, intravenously, intraperitoneally, inhalationally, etc. Particularly preferred embodiments of the invention employ continuous intravenous administration of the polypeptides of the instant invention, or an amide, ester, or salt thereof. The polypeptides on the instant invention may be administered as a bolus or as a continuous infusion over a period of time. An implantable pump may be used. In certain embodiments of the invention, intermittent or continuous polypeptides administration is continued for one to several days (e.g., 2-3 or more days), or for longer periods of time, e.g., weeks, months, or years. In some embodiments, intermittent or continuous polypeptide administration is provided for at least about 3 days. In other embodiments, intermittent or continuous polypeptide administration is provided for at least about one week. In other embodiments, intermittent or continuous polypeptide administration is provided for at least about two weeks. It may be desirable to maintain an average plasma polypeptide concentration above a particular threshold value either during administration or between administration of multiple doses. A desirable concentration may be determined, for example, based on the subject's physiological condition, disease severity, etc. Such desirable value(s) can be identified by performing standard clinical trials.

In another aspect, the present invention provides a pharmaceutical composition comprising a polypeptide of the present invention or and amide, an ester or a salt thereof and one or more pharmaceutically acceptable carriers. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, lyophilizates, powders or suppositories), or in a liquid form (including without limitation solutions, suspensions or emulsions). The pharmaceutical compositions can be subjected to conventional pharmaceutical operations such as aseptic manufacturing, sterilization and/or can contain conventional inert diluents, cake forming agents, tonicity agents, lubricating agents, or buffering agents, as well as adjuvants, such as preservatives, stabilizers, wetting agents, emulsifers and buffers, etc.

Pharmaceutical compositions suitable for injectable use typically include sterile aqueous solutions (where water soluble) or dispersions and sterile powders for the extemporaneous preparation of sterile injectable solutions or dispersion.

For intravenous administration, suitable carriers include physiological saline, bacteriostatic water, Cremophor ELTM (BASF, Parsippany, N.J.) or phosphate buffered saline (PBS). In all cases, the composition should be sterile and should be fluid to the extent that easy syringability exists. Preferred pharmaceutical formulations are stable under the conditions of manufacture and storage and must be preserved against the contaminating action of microorganisms such as bacteria and fungi. In general, the relevant carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, amino acids, sorbitol, sodium chloride in the composition. Prolonged absorption of the injectable compositions can be brought about by including in the composition an agent which delays absorption, for example, aluminum monostearate and gelatin.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Sterile injectable solutions can be prepared by incorporating the active compound in the required amount in an appropriate solvent with one or a combination of ingredients enumerated above, as required, followed by filration sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Formulations for oral delivery may advantageously incorporate agents to improve stability within the gastrointestinal tract and/or to enhance absorption.

For administration by inhalation, the inventive therapeutic agents are preferably delivered in the form of an aerosol spray from pressured container or dispenser which contains a suitable propellant, e.g., a gas such as carbon dioxide, or a nebulizer. It is noted that the lungs provide a large surface area for systemic delivery of therapeutic agents.

The agents may be encapsulated, e.g., in polymeric microparticles such as those described in U.S. publication 20040096403, or in association with any of a wide variety of other drug delivery vehicles that are known in the art. In other embodiments of the invention the agents are delivered in association with a charged lipid as described, for example, in U.S. publication 20040062718. It is noted that the latter system has been used for administration of a therapeutic polypeptide, insulin, demonstrating the utility of this system for administration of peptide agents.

Systemic administration can also be by transmucosal or transdermal means.

Suitable compositions for transdermal application include an effective amount of a polypeptide of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

Method of the Invention:

Apelin family of peptides is the only known natural family of ligands for the G protein coupled APJ receptor. Apelin gene encodes a 77 aminoacid polypeptide, which gets processed into biologically active forms of apelin peptides, such as apelin-36, apelin-17, apelin-16, apelin-13, apelin-12 and pyroglutamate modified form of apelin-13 (Pyr$^1$-apelin-13). Any one of these apelin peptides, upon binding to APJ receptor, transduces the signal via Gi and Gq proteins. In cardiomyocytes, Gi or Gq coupling leads to changes in intracellular pH, PLC activation, and IP3 production that enhance myofilament calcium sensitivity and ultimately result in increased cardiac contractility. Gi coupling inhibits activated Gs, adenylyl cyclase and cAMP production and increases pAkt levels leading to cardioprotection. In vascular endothelial cells, APJ activation via Gi, pAKT leads to increased nitric oxide (NO) production, which increases smooth muscle relaxation resulting in overall vasodilation.

Patients with chronic stable heart failure have occasional acute episodes of decompensation, where cardiac contractility declines further and symptoms worsen. These exacerbations are referred to as acute decompensated heart failure (ADHF). Current therapies for ADHF include diuretics, vasodilators, and inotropes, which directly increase cardiac contractility. Current intravenous inotropes (dobutamine, dopamine, milrinone, levosimendan) are well known for their adverse events such as arrhythmia and increased long-term mortality. The synthetic apelin polypeptide analogs of the instant invention provide a therapy for ADHF that increases cardiac contractility without arrhythmogenic or mortality liabilities and address the enormous unmet medical need in chronic heart failure.

Indeed, acute apelin treatment (5 min) in humans results in coronary vasodilatation and improved cardiac output. However, native apelins exhibit a very short $t_{1/2}$ (seconds) and duration of action (few minutes) in vivo. The potent synthetic apelin peptide agonists of the instant invention have longer half lives compared to the native apelin.

Activation of APJ receptor in cardiomyocytes a) improve cardiac contractility via Gi/Gq, PLC and Ca2+, and b) provide cardioprotection via Gi, pAkt activation, but without increasing cAMP (as seen with other inotropes). In addition, APJ agonism in endothelial cells leads to arterial vasodilation, which further benefits heart failure by unloading the work of left ventricle. Taken together the synthetic apelin polypeptide analogs can improve overall cardiac function, reduce arrhythmogenesis and provide survival benefit.

More recently, there have been a number of preclinical research publications focusing on the potential involvement of Apelin in diabetes and insulin resistance. Apelin has been shown to 1) lower blood glucose levels by improving glucose uptake in muscle, adipose and heart, 2) protect pancreatic beta cells from ER stress and subsequent apoptosis, 3) lower the insulin secretion in beta cells, and 4) regulate catecholamine induced lypolysis in adipose tissue. Activation of pAKT pathway has been implicated in these processes.

The polypeptides according to anyone of formulae I to IX, or a pharmaceutically acceptable salt thereof, in free form or in pharmaceutically acceptable salt form, exhibit valuable pharmacological properties, e.g. APJ receptor agonsim properties, e.g. as indicated in in vitro and in vivo tests as provided in the next sections and are therefore indicated for therapy.

Polypeptides of the invention or a pharmaceutically acceptable salt thereof, may be useful in the treatment of an indication selected from acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

Thus, as a further embodiment, the present invention provides the use of a polypeptide of anyone of formulae I to IX, or an amide, an ester or a salt thereof for the treatment of a disease which is associated with the APJ receptor activity. In a further embodiment, the therapy is selected from a disease which is responsive to the agonism of the APJ receptor. In another embodiment, the disease is selected from the afore-mentioned list, suitably acute decompensated heart failure. In yet another subset of this embodiment, the present invention provides the use of a polypeptide of anyone of formulae I to IX, or an amide, ester or a salt thereof, in the manufacture of a medicament, for the treatment of a disease which is associated with the APJ receptor activity.

Thus, as a further embodiment, the present invention provides the use of a polypeptide of anyone of formulae I to IX, or an amide, an ester or a salt thereof, in therapy. In a further embodiment, the therapy is selected from a disease which may be treated by activation (agonism) of the APJ receptor.

In another embodiment, the invention provides a method of treating a disease which is responsive to the agonism of the APJ receptor, comprising administration of a therapeutically acceptable amount of a polypeptide of anyone of formulae I to IX, or an amide, an ester of a salt thereof. In a further embodiment, the disease is selected from the afore-mentioned list, suitably acute decompensated heart failure.

In yet another subset of this embodiment, the invention provides a method of treating a disease which is associated with the activity of the APJ receptor comprising administration of a therapeutically acceptable amount of a polypeptide of anyone of formulae I to IX, or an amide, an ester or a salt thereof.

The effective amount of a pharmaceutical composition or combination of the invention to be employed therapeutically will depend, for example, upon the therapeutic context and objectives. One skilled in the art will appreciate that the appropriate dosage levels for treatment will thus vary depending, in part, upon the molecule delivered, the indication for which the fusion protein variant is being used, the route of administration, and the size (body weight, body surface, or organ size) and condition (the age and general health) of the patient. Accordingly, the clinician can titer the dosage and modify the route of administration to obtain the optimal therapeutic effect. A typical dosage can range from about 0.1 µg/kg to up to about 100 mg/kg or more, depending on the factors mentioned above. In other embodiments, the dosage can range from 0.1 µg/kg up to about 100 mg/kg; or 1 µg/kg up to about 100 mg/kg.

The frequency of dosing will depend upon the pharmacokinetic parameters of the dual function protein in the formulation being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The activity of a polypeptide according to the present invention can be assessed by the following in vitro methods described below.

hAPJ Calcium Flux Assay:

Chem-5 APJ stable cells (Millipore # HTS068C) were plated in 384-well format with 10,000 cells/well in 25 ul growth media, then grown 24 hours in a 37° C. tissue culture incubator. One hour before the assay, 25 ul/well FLIPR Calcium 4 dye (Molecular Devices R8142) with 2.5 mM probenecid was added, and cells were incubated one hour in a 37° C. tissue culture incubator. Peptides were solubilized in HBSS, HEPES & 0.1% BSA buffer, and serially-diluted 10-fold, from 50 uM to 5 pM, in triplicate. FLIPR Tetra was used to add peptide to the cells with dye (1:5, for final peptide concentrations ranging from 10 uM to 1 pM). FLIPR dye inside the cells emitted fluorescence after binding to calcium, while fluorescence from outside the cells was masked. Fluorescence was measured using 470-495 excitation and 515-575 emission wavelengths on the FLIPR Tetra. Readings were done for 3 minutes total, beginning 10 seconds before the peptide addition. Maximum-minimum values were calculated and plotted for each peptide concentration, and Graph Pad prism software was used to calculate $EC_{50}$ values at the curve inflection points, for calcium flux stimulation by peptides.

Plasma Stability Assay:

Materials:

Working solution: 1 mg/mL test article is prepared in Milli-Q water

Extraction solution: Methanol:Acetonitrile:Water (1:1:1) with 0.1% Formic Acid and 400 ng/mL Glyburide.

Plasma: Male Sprague-Dawley rat plasma (with sodium heparin), purchased from Bioreclamation LLC (Liverpool, N.Y.).

Whole blood: Male Sprague Dawley whole blood (with sodium heparin), purchased from Bioreclamation LLC (Liverpool, N.Y.)

Lung homogenate: Male rat Sprague Dawley lung was purchased from Bioreclamation LLC (Liverpool, N.Y.). The lung was homogenized using polytron homogenizer after addition of 5× volume of 1×PBS. The homogenate was centrifuged at 9000 rpm for 10 min at 4° C. The supernatant was centrifuged again at 3000 rpm for 30 min to make a clear supernatant. Protein concentration was determined using a commercial kit (Pierce, Thermo Scientific).

Sample Preparation Procedure:

Test article was prepared in one of the following biological matrices: heparinized rat plasma, heparinized rat whole blood or lung homogenate. The plasma and whole blood sample was prepared at 5000 ng/mL by adding 5 uL of 1 mg/mL Working solution to 995 uL of rat plasma or whole blood. Lung homogenate samples were prepared by diluting lung homogenate to 1 mg/ml protein concentration with phosphate buffered saline (PBS), followed by addition of 5 uL Working solution to 995 uL diluted lung homogenate. The samples were incubated at 37° C. with gentle shaking (65~75 rpm) in a water bath incubator. At times 0 min, 5 min, 15 min, 30 min, 60 min, 120 and 240 min, 25 uL aliquots of incubation samples were transferred to 96-well plate and immediately protein precipitated using 150 uL of Extraction solution. After completion of incubation experiment, the sample plate was centrifuged at 4000 rpm at 4° C. for 10 minutes. Afterwards, a pipetting device (Tecan Temo) was used to tranfer the supernatants to another plate and add 50 uL of water to all samples. The plate was vortexed prior to LC-MS analysis.

LC-MS Analysis of Stability Samples
HPLC: Agilent 1290 HPLC with autosampler
Column: MAC-MOD ACE C18, 3 μm, 30 mm×2.1 mm i.d.
Mobile phase A: 0.1% Formic acid in acetonitrile
Mobile phase B: 0.1% Formic acid in water
Gradient Program:

| Time (min) | Flow (mL) | Mobile Phase A (%) | Mobile Phase B (%) |
|---|---|---|---|
| 0 | 0.4 | 95 | 5 |
| 0.5 | 0.4 | 95 | 5 |
| 1.5 | 0.4 | 5 | 95 |
| 4.1 | 0.4 | 5 | 95 |
| 4.2 | 0.4 | 95 | 5 |
| 5 | 0.4 | 95 | 5 |

Mass spectrometer: Agilent Q-TOF 6530
Data acquisition mode: Full scan with mass range of 100-1000 m/z
Data acquisition and analysis software: MassHunter
Data Analysis:
Stability assay: stability half-life, (t ½), values were determined by converting peak areas at each time point to percent remaining relative to initial (t=0) peak area.
Percent remaining=100×(sample peak area)÷(t=0 peak area)
The natural log of percent remaining values were calculated and plotted against sample time (Microsoft Excel). The slope of this line, k, was determined by linear regression (Microsoft Excel).
Stability half-life was then calculated by the formula, t ½=0.693÷k
Surrogate Activity-Based Plasma Stability Assay:
The calcium flux protocol described above was followed, with the following changes. The peptides were also incubated with 5% rat plasma (Bioreclamation # RATPLNAHP-M, Na Heparin-treated). Readings were taken at time points $t_0$ and $t_{24}$ hrs, after incubation in a 37° C. tissue culture incubator. Peptide plasma half-life in minutes was estimated by calculating the following:
1) LN(($EC_{50}$ at $t_0$)/($EC_{50}$ at $t_{24\ hrs}$)),
2) Calculate slope of value above and
3) $t_{1/2}$=0.693/(slope^2).

Using the test assay (as described above) polypeptides of the invention exhibited efficacy and stability in accordance to Tables 2 and 3, provided infra.

TABLE 2

Activity and Stability of Polypeptides

| Peptide | hAPJ $Ca^{2+}$ Flux $EC_{50}$ [nM] | Surrogate activity-based Plasma stability t½ [min] |
|---|---|---|
| Example 1 | 90.13 | 30.7 |
| Example 2 | 132.58 | 27.1 |
| Example 3 | 1008.19 | 98.0 |
| Example 4 | 746.74 | 50.0 |
| Example 5 | 21.25 | 126.2 |
| Example 6 | 21.98 | 117.2 |
| Example 7 | 90.85 | >1000 |
| Example 8 | 1.04 | 407 |
| Example 9 | 2.16 | >1000 |
| Example 10 | 2.54 | >1000 |
| Example 11 | 3.52 | >1000 |
| Example 12 | 2.07 | 93.6 |
| Example 13 | 2.26 | 283.6 |
| Example 14 | 8.83 | 85.2 |
| Example 15 | 3.53 | 180.3 |
| Example 16 | 1.43 | 13.4 |

TABLE 2-continued

Activity and Stability of Polypeptides

| Peptide | hAPJ $Ca^{2+}$ Flux $EC_{50}$ [nM] | Surrogate activity-based Plasma stability t½ [min] |
|---|---|---|
| Example 17 | 3.29 | 14.1 |
| Example 18 | 1.62 | 248.1 |
| Example 19 | 8.46 | 28.4 |
| Example 20 | 173.24 | 490.4 |
| Example 21 | 75.81 | 639.7 |
| Example 22 | 42.03 | 799.9 |
| Example 23 | 52.42 | >1000 |
| Example 24 | 32.65 | 303.5 |
| Example 25 | 24.50 | >1000 |
| Example 26 | 29.84 | >1000 |
| Example 27 | 65.55 | >1000 |
| Example 28 | 5.68 | 440.3 |
| Example 29 | 4.33 | 216.6 |
| Example 30 | 6.05 | >1000 |
| Example 31 | 84.11 | >1000 |
| Example 32 | 518.08 | >1000 |
| Example 33 | 8.10 | >1000 |
| Example 34 | 3.21 | 505.2 |
| Example 35 | 11.12 | >1000 |
| Example 36 | 7.36 | >1000 |
| Example 37 | 1.40 | 164.3 |
| Example 38 | 181.77 | >1000 |
| Example 39 | 8.20 | 654.9 |
| Example 40 | 7.99 | >1000 |
| Example 41 | 6.91 | 627.1 |
| Example 42 | 92.77 | >1000 |
| Example 43 | 4.14 | >1000 |
| Example 44 | 5.94 | 855.8 |
| Example 45 | 6.55 | 167.3 |
| Example 46 | 3.87 | 502.1 |
| Example 47 | 2.41 | 418.9 |
| Example 48 | 4.10 | 546.4 |
| Example 49 | 34.19 | >1000 |
| Example 50 | 1.92 | >1000 |
| Example 51 | 1.09 | 655.9 |
| Example 52 | 53.88 | 777.8 |
| Example 53 | 1.07 | >1000 |
| Example 54 | 6.70 | >1000 |
| Example 55 | 8.16 | >1000 |
| Example 56 | 1.12 | >1000 |
| Example 57 | 2.01 | >1000 |
| Example 58 | 13.09 | >1000 |
| Example 59 | 10.00 | >1000 |
| Example 60 | 8.15 | >1000 |
| Example 61 | 89.15 | 259.9 |
| Example 62 | 3.32 | >1000 |
| Example 63 | 3.18 | 703.9 |
| Example 64 | 6.3 | 455 |
| Example 65 | 1.1 | 596 |
| Example 66 | 589 | 596 |
| Comparative Example: Pyr1-apelin-13 | 1.79 | 5.0 |

TABLE 3

Correlation between plasma stabililty Assay and Surrogate Activity based Plasma Stability assay:

| Peptide | Plasma stability t½ [min] | Surrogate Activity based Plasma stability t½ [min] |
|---|---|---|
| Example 8 | 163 | 407 |
| Example 12 | 53.9 | 96.16 |
| Example 13 | 183 | 283.6 |
| Example 14 | 63 | 85.2 |
| Example 16 | 10.2 | 13.4 |
| Example 17 | 2.3 | 14.1 |

TABLE 3-continued

Correlation between plasma stabililty Assay and Surrogate Activity based Plasma Stability assay:

| Peptide | Plasma stability t½ [min] | Surrogate Activity based Plasma stability t½ [min] |
|---|---|---|
| Example 18 | 220 | 248.1 |
| Pyr-1-Apelin 13 | 6.6 | 5.0 |

The polypeptide of the present invention may have an APJ receptor potency similar to apelin-13 or pyr-1-apelin-13. In one embodiment the polypeptide of the present invention has an $EC_{50}$ of less than 100 nM. In another embodiment the polypeptide of the invention has an $EC_{50}$ of less than 50 nM, preferably less than 25 nM and more preferably less than 15 nM. In yet another embodiment, the polypeptide of the present invention has an $EC_{50}$ of less than 10 nM.

The polypeptide of the present invention may have plasma stability superior to apelin-13 or pyr-1-apelin-13. In one embodiment, the plasma stability improvement is at least 2 fold. In one embodiment, the polypeptide of the invention has a plasma stability of at least 30 minutes. In another embodiment, the polypeptide of the invention has a plasma stability of at least 10 minutes, at least 40 min and more preferably at least 60 minutes.

The polypeptide of the present invention may be administered either simultaneously with, or before or after, one or more other therapeutic agent. The polypeptide of the present invention may be administered separately, by the same or different route of administration, or together in the same pharmaceutical composition as the other agents.

In one embodiment, the invention provides a product comprising a polypeptide of anyone of formulae I to IX, or an amide, an ester of a salt thereof, and at least one other therapeutic agent as a combined preparation for simultaneous, separate or sequential use in therapy. In one embodiment, the therapy is the treatment of a disease or condition responsive to the activation of the APJ receptor.

Products provided as a combined preparation include a composition comprising a polypeptide of anyone of formulae I to IX, or an amide, an ester of a salt thereof, and the other therapeutic agent(s) together in the same pharmaceutical composition, or a polypeptide of anyone of formulae I to IX, or an amide, an ester or a salt thereof, and the other therapeutic agent(s) in separate form, e.g. in the form of a kit.

In one embodiment, the invention provides a pharmaceutical composition comprising a polypeptide of anyone of formulae I to IX, or an amide, an ester or a salt thereof, and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a polypeptide of anyone of formula I' and I to IX, or an amide, an ester or a salt thereof. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of a polypeptide of the invention and the other therapeutic agent.

Accordingly, the invention provides the use of a polypeptide of anyone of formulae I to IX, or an amide, an ester or a salt thereof, for treating a disease or condition responsive to the agonism of the APJ receptor, wherein the medicament is prepared for administration with another therapeutic agent. The invention also provides the use of another therapeutic agent for treating a disease or condition responsive to the agonism of the apelin receptor, wherein the medicament is administered with a polypeptide of anyone of formulae I to IX, or an amide, an ester or a salt thereof.

The invention also provides a polypeptide of anyone of formulae I to IX, or a pharmaceutically acceptable salt thereof, for use in a method of treating a disease or condition responsive to the agonism of the APJ receptor, wherein the polypeptide of anyone of formulae I to IX, or an amide, an ester or a salt thereof, is prepared for administration with another therapeutic agent. The invention also provides another therapeutic agent for use in a method of treating a disease or condition responsive to the agonism of the APJ receptor, wherein the other therapeutic agent is prepared for administration with a polypeptide of anyone of formulae I to IX, or an amide, an ester or a salt thereof. The invention also provides a polypeptide of anyone of formulae I to IX, or an amide, an ester or a salt thereof, for use in a method of treating a disease or condition responsive to the agonism of the APJ receptor, wherein the polypeptide of anyone of formulae I to IX, or an amide, an ester or a salt thereof, is administered with another therapeutic agent. The invention also provides another therapeutic agent for use in a method of treating a disease or condition responsive to the agonism of the APJ receptor, wherein the other therapeutic agent is administered with a polypeptide of anyone of formulae I to IX or an amide, an ester or a salt thereof.

The invention also provides the use of a polypeptide of anyone of formulae I to IX, or an amide, an ester or a salt thereof, for treating a disease or condition responsive to the agonism of the APJ receptor, wherein the patient has previously (e.g. within 24 hours) been treated with another therapeutic agent. The invention also provides the use of another therapeutic agent for treating a disease or condition responsive to the agonism of the APJ receptor, wherein the patient has previously (e.g. within 24 hours) been treated with a polypeptide of anyone of formulae I to IX, or an amide, an ester or a salt thereof.

In one embodiment, the other therapeutic agent is selected from inotropes, beta adrenergic receptor blockers, HMG-Co-A reductase inhibitors, angiotensin II receptor antagonists, angiotensin converting enzyme (ACE) Inhibitors, calcium channel blockers (CCB), endothelin antagonists, renin inhibitors, diuretics, ApoA-I mimics, anti-diabetic agents, obesity-reducing agents, aldosterone receptor blockers, endothelin receptor blockers, aldosterone synthase inhibitors (ASI), a CETP inhibitor, anti-coagulants, relaxin, BNP (nesiritide) and a NEP inhibitor.

The term "in combination with" a second agent or treatment includes co-administration of the polypeptide of the invention (e.g., a polypeptide according to anyone of Formulae I-IX or a polypeptide otherwise described herein) with the second agent or treatment, administration of the compound of the invention first, followed by the second agent or treatment and administration of the second agent or treatment first, followed by the compound of the invention.

The term "second agent" includes any agent which is known in the art to treat, prevent, or reduce the symptoms of a disease or disorder described herein, e.g. a disorder or disease responsive to the actvation of the APJ receptor, such as for example, acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

Examples of second agents include inotropes, beta adrenergic receptor blockers, HMG-Co-A reductase inhibitors, angiotensin II receptor antagonists, angiotensin converting enzyme (ACE) Inhibitors, calcium channel blockers (CCB), endothelin antagonists, renin inhibitors, diuretics, ApoA-I mimics, anti-diabetic agents, obesity-reducing agents, aldosterone receptor blockers, endothelin receptor blockers, aldosterone synthase inhibitors (ASI), a CETP inhibitor, anti-coagulants, relaxin, BNP (nesiritide) and/or a NEP inhibitor.

Inotropes as used herein include for example dobutamine, isoproterenol, milrinone, amirinone, levosimendan, epinephrine, norepinephrine, isoproterenol and digoxin.

Beta adrenergic receptor blockers as used herein include for example acebutolol, atenolol, betaxolol, bisoprolol, carteolol, metoprolol, nadolol, propranolol, sotalol and timolol.

Anti-coagulants as used herein include Dalteparin, Danaparoid, Enoxaparin, Heparin, Tinzaparin, Warfarin.

The term "HMG-Co-A reductase inhibitor" (also called beta-hydroxy-beta-methylglutaryl-co-enzyme-A reductase inhibitors) includes active agents that may be used to lower the lipid levels including cholesterol in blood. Examples include atorvastatin, cerivastatin, compactin, dalvastatin, dihydrocompactin, fluindostatin, fluvastatin, lovastatin, pitavastatin, mevastatin, pravastatin, rosuvastatin, rivastatin, simvastatin, and velostatin, or, pharmaceutically acceptable salts thereof.

The term "ACE-inhibitor" (also called angiotensin converting enzyme inhibitors) includes molecules that interrupt the enzymatic degradation of angiotensin I to angiotensin II. Such compounds may be used for the regulation of blood pressure and for the treatment of congestive heart failure. Examples include alacepril, benazepril, benazeprilat, captopril, ceronapril, cilazapril, delapril, enalapril, enaprilat, fosinopril, imidapril, lisinopril, moexipril, moveltopril, perindopril, quinapril, ramipril, spirapril, temocapril, and trandolapril, or, pharmaceuticals salt thereof.

The term "endothelin antagonist" includes bosentan (cf. EP 526708 A), tezosentan (cf. WO 96/19459), or, pharmaceutically acceptable salts thereof.

The term "renin inhibitor" includes ditekiren (chemical name: [1S-[1R*,2R*,4R*(1R*,2R*)]]-1-[(1,1-dimethylethoxy)carbonyl]-L-prolyl-L-phenylalanyl-N-[2-hydroxy-5-methyl-1-(2-methylpropyl)-4-[[[2-methyl-1-[[(2-pyridinylmrthyl)amino]carbonyl]butyl]amino]carbonyl]hexyl]-N-alfa-methyl-L-histidinamide); terlakiren (chemical name: [R—(R*,S*)]—N-(4-morpholinylcarbonyl)-L-phenylalanyl-N-[1-(cyclohexylmethyl)-2-hydroxy-3-(1-methylethoxy)-3-oxopropyl]-S-methyl-L-cysteineamide); Aliskiren (chemical name: (2S,4S,5S,7S)-5-amino-N-(2-carbamoyl-2,2-dimethylethyl)-4-hydroxy-7-{[4-methoxy-3-(3-methoxypropoxy)phenyl]methyl}-8-methyl-2-(propan-2-yl)nonanamide) and zankiren (chemical name: [1S-[1R*[R*(R*)],2S*,3R*]]—N-[1-(cyclohexylmethyl)-2,3-dihydroxy-5-methylhexyl]-alfa-[[2-[[(4-methyl-1-piperazinyl)sulfonyl]methyl]-1-oxo-3-phenylpropyl]-amino]-4-thiazolepropanamide), or, hydrochloride salts thereof, or, SPP630, SPP635 and SPP800 as developed by Speedel, or RO 66-1132 and RO 66-1168 of Formula (A) and (B):

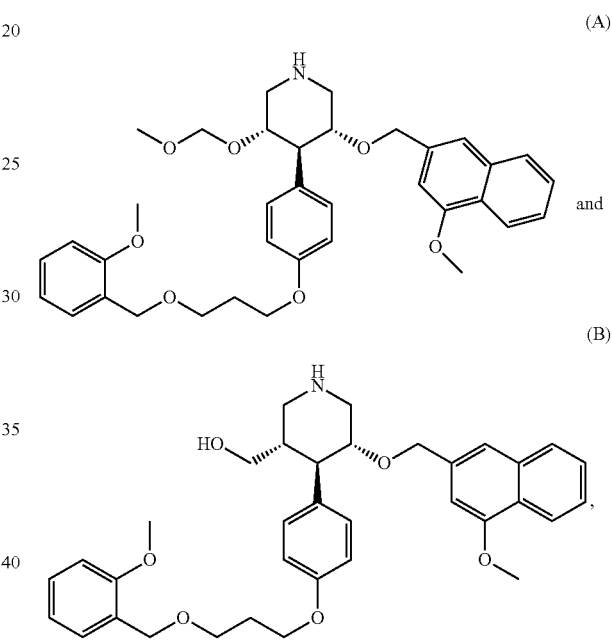

or, pharmaceutically acceptable salts thereof.

The term "aliskiren", if not defined specifically, is to be understood both as the free base and as a salt thereof, especially a pharmaceutically acceptable salt thereof, most preferably a hemi-fumarate salt thereof.

The term "calcium channel blocker (CCB)" includes dihydropyridines (DHPs) and non-DHPs (e.g., diltiazem-type and verapamil-type CCBs). Examples include amlodipine, Bepridil, Diltiazem, felodipine, ryosidine, isradipine, lacidipine, nicardipine, nifedipine, niguldipine, niludipine, nimodipine, nisoldipine, nitrendipine, Verapamil and nivaldipine, and is preferably a non-DHP representative selected from the group consisting of flunarizine, prenylamine, diltiazem, fendiline, gallopamil, mibefradil, anipamil, tiapamil and verapamil, or, pharmaceutically acceptable salts thereof. CCBs may be used as anti-hypertensive, anti-angina pectoris, or anti-arrhythmic drugs.

The term "diuretic" includes thiazide derivatives (e.g., chlorothiazide, hydrochlorothiazide, methylclothiazide, and chlorothalidon).

The term "ApoA-I mimic" includes D4F peptides (e.g., formula D-W-F-K-A-F-Y-D-K-V-A-E-K-F-K-E-A-F) (SEQ ID NO: 7)

An angiotensin II receptor antagonist or a pharmaceutically acceptable salt thereof is understood to be an active ingredient which bind to the $AT_1$-receptor subtype of angiotensin II receptor but do not result in activation of the receptor. As a consequence of the inhibition of the $AT_1$ receptor, these antagonists can, for example, be employed as antihypertensives or for treating congestive heart failure.

The class of $AT_1$ receptor antagonists comprises compounds having differing structural features, essentially preferred are the non-peptidic ones. For example, mention may be made of the compounds which are selected from the group consisting of valsartan, losartan, candesartan, eprosartan, irbesartan, saprisartan, tasosartan, telmisartan, the compound with the designation E-1477 of the following formula

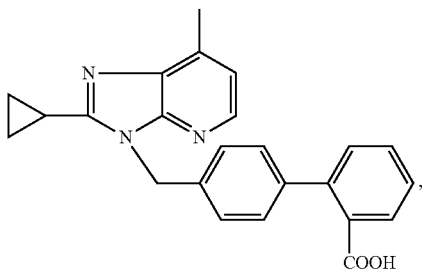 [SMILES: Cc1ccnc2c1nc(C1CC1)n2Cc1ccc(-c2ccccc2C(=O)O)cc1]

the compound with the designation SC-52458 of the following formula

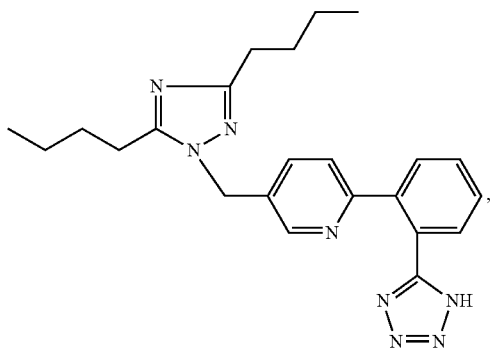 [SMILES: CCCCc1nc(CCCC)n(Cc2ccc(-c3ccccc3-c3nnn[nH]3)nc2)n1]

and the compound with the designation ZD-8731 of the following formula

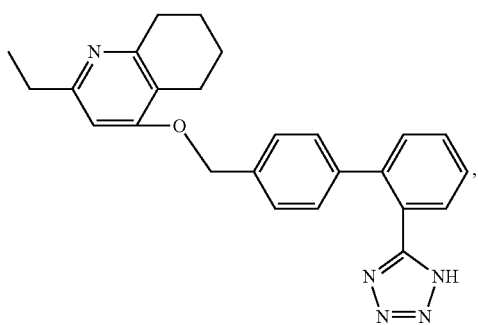 [SMILES: CCc1cc(OCc2ccc(-c3ccccc3-c3nnn[nH]3)cc2)c2c(n1)CCCC2]

or, in each case, a pharmaceutically acceptable salt thereof.

Preferred $AT_1$-receptor antagonist are candesartan, eprosartan, irbesartan, losartan, telmisartan, valsartan. Also preferred are those agents which have been marketed, most preferred is valsartan or a pharmaceutically acceptable salt thereof.

The term "anti-diabetic agent" includes insulin secretion enhancers that promote the secretion of insulin from pancreatic β-cells. Examples include biguanide derivatives (e.g., metformin), sulfonylureas (SU) (e.g., tolbutamide, chlorpropamide, tolazamide, acetohexamide, 4-chloro-N-[(1-pyrolidinylamino)carbonyl]-benzensulfonamide (glycopyramide), glibenclamide (glyburide), gliclazide, 1-butyl-3-metanilylurea, carbutamide, glibonuride, glipizide, gliquidone, glisoxepid, glybuthiazole, glibuzole, glyhexamide, glymidine, glypinamide, phenbutamide, and tolylcyclamide), or pharmaceutically acceptable salts thereof. Further examples include phenylalanine derivatives (e.g., nateglinide [N-(trans-4-isopropylcyclohexylcarbonyl)-D-phenylalanine] (cf. EP 196222 and EP 526171) of the formula

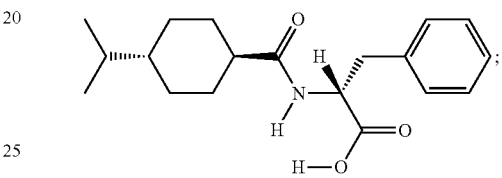

repaglinide [(S)-2-ethoxy-4-{2-[[3-methyl-1-[2-(1-piperidinyl)phenyl]butyl]amino]-2-oxoethyl}benzoic acid] (cf. EP 589874, EP 147850 A2, in particular Example 11 on page 61, and EP 207331 A1); calcium (2S)-2-benzyl-3-(cis-hexahydro-2-isoindolinlycarbonyl)-propionate dihydrate (e.g., mitiglinide (cf. EP 507534)); and glimepiride (cf. EP 31058).

Further examples of second agents with which the peptide and polypeptide of the invention can be used in combination include DPP-IV inhibitors, GLP-1 and GLP-1 agonists.

DPP-IV is responsible for inactivating GLP-1. More particularly, DPP-IV generates a GLP-1 receptor antagonist and thereby shortens the physiological response to GLP-1. GLP-1 is a major stimulator of pancreatic insulin secretion and has direct beneficial effects on glucose disposal.

The DPP-IV (dipeptidyl peptidase IV) inhibitor can be peptidic or, preferably, non-peptidic. DPP-IV inhibitors are in each case generically and specifically disclosed e.g. in WO 98/19998, DE 196 16 486 A1, WO 00/34241 and WO 95/15309, in each case in particular in the compound claims and the final products of the working examples, the subject-matter of the final products, the pharmaceutical preparations and the claims are hereby incorporated into the present application by reference to these publications. Preferred are those compounds that are specifically disclosed in Example 3 of WO 98/19998 and Example 1 of WO 00/34241, respectively.

GLP-1 (glucagon like peptide-1) is an insulinotropic protein which is described, e.g., by W. E. Schmidt et al. in *Diabetologia*, 28, 1985, 704-707 and in U.S. Pat. No. 5,705,483.

The term "GLP-1 agonists" includes variants and analogs of GLP-1(7-36)$NH_2$ which are disclosed in particular in U.S. Pat. No. 5,120,712, U.S. Pat. No. 5,118,666, U.S. Pat. No. 5,512,549, WO 91/11457 and by C. Orskov et al in J. Biol. Chem. 264 (1989) 12826. Further examples include GLP-1(7-37), in which compound the carboxy-terminal amide functionality of $Arg^{36}$ is displaced with Gly at the $37^{th}$ position of the GLP-1(7-36)$NH_2$ molecule and variants and analogs thereof including $GLN^9$-GLP-1(7-37), D-$GLN^9$-

GLP-1(7-37), acetyl LYS⁹-GLP-1(7-37), LYS¹⁸-GLP-1(7-37) and, in particular, GLP-1(7-37)OH, VAL⁸-GLP-1(7-37), GLY⁸-GLP-1(7-37), THR⁸-GLP-1(7-37), MET⁸-GLP-1(7-37) and 4-imidazopropionyl-GLP-1. Special preference is also given to the GLP agonist analog exendin-4, described by Greig et al. in Diabetologia 1999, 42, 45-50.

Also included in the definition "anti-diabetic agent" are insulin sensitivity enhancers which restore impaired insulin receptor function to reduce insulin resistance and consequently enhance the insulin sensitivity. Examples include hypoglycemic thiazolidinedione derivatives (e.g., glitazone, (S)-((3,4-dihydro-2-(phenyl-methyl)-2H-1-benzopyran-6-yl)methyl-thiazolidine-2,4-dione (englitazone), 5-{[4-(3-(5-methyl-2-phenyl-4-oxazolyl)-1-oxopropyl)-phenyl]-methyl}-thiazolidine-2,4-dione (darglitazone), 5-{[4-(1-methyl-cyclohexyl)methoxy)-phenyl]methyl}-thiazolidine-2,4-dione (ciglitazone), 5-{[4-(2-(1-indolyl)ethoxy)phenyl]methyl}-thiazolidine-2,4-dione (DRF2189), 5-{4-[2-(5-methyl-2-phenyl-4-oxazolyl)-ethoxy)]benzyl}-thiazolidine-2,4-dione (BM-13.1246), 5-(2-naphthylsulfonyl)-thiazolidine-2,4-dione (AY-31637), bis{4-[(2,4-dioxo-5-thiazolidinyl)methyl]phenyl}methane (YM268), 5-{4-[2-(5-methyl-2-phenyl-4-oxazolyl)-2-hydroxyethoxy]benzyl}-thiazolidine-2,4-dione (AD-5075), 5-[4-(1-phenyl-1-cyclopropanecarbonylamino)-benzyl]-thiazolidine-2,4-dione (DN-108) 5-{[4-(2-(2,3-dihydroindol-1-yl)ethoxy)phenyl]methyl}-thiazolidine-2,4-dione, 5-[3-(4-chlorophenyl])-2-propynyl]-5-phenylsulfonyl)thiazolidine-2,4-dione, 5-[3-(4-chlorophenyl)-2-propynyl]-5-(4-fluorophenyl-sulfonyl)thiazolidine-2,4-dione, 5-{[4-(2-(methyl-2-pyridinyl-amino)-ethoxy)phenyl]methyl}-thiazolidine-2,4-dione (rosiglitazone), 5-{[4-(2-(5-ethyl-2-pyridyl)ethoxy)phenyl]-methyl}thiazolidine-2,4-dione (pioglitazone), 5-{[4-((3,4-dihydro-6-hydroxy-2,5,7,8-tetramethyl-2H-1-benzopyran-2-yl)methoxy)-phenyl]-methyl}-thiazolidine-2,4-dione (troglitazone), 5-[6-(2-fluoro-benzyloxy)naphthalen-2-ylmethyl]-thiazolidine-2,4-dione (MCC555), 5-{[2-(2-naphthyl)-benzoxazol-5-yl]-methyl}thiazolidine-2,4-dione (T-174) and 5-(2,4-dioxothiazolidin-5-ylmethyl)-2-methoxy-N-(4-trifluoromethyl-benzyl)benzamide (KRP297)).

Further anti-diabetic agents include, insulin signalling pathway modulators, like inhibitors of protein tyrosine phosphatases (PTPases), antidiabetic non-small molecule mimetic compounds and inhibitors of glutamine-fructose-6-phosphate amidotransferase (GFAT); compounds influencing a dysregulated hepatic glucose production, like inhibitors of glucose-6-phosphatase (G6Pase), inhibitors of fructose-1,6-bisphosphatase (F-1,6-Bpase), inhibitors of glycogen phosphorylase (GP), glucagon receptor antagonists and inhibitors of phosphoenolpyruvate carboxykinase (PEPCK); pyruvate dehydrogenase kinase (PDHK) inhibitors; inhibitors of gastric emptying; insulin; inhibitors of GSK-3; retinoid X receptor (RXR) agonists; agonists of Beta-3 AR; agonists of uncoupling proteins (UCPs); non-glitazone type PPARγ agonists; dual PPARα/PPARγ agonists; antidiabetic vanadium containing compounds; incretin hormones, like glucagon-like peptide-1 (GLP-1) and GLP-1 agonists; beta-cell imidazoline receptor antagonists; miglitol; α₂-adrenergic antagonists; and pharmaceutically acceptable salts thereof.

In one embodiment, the invention provides a combination, in particular a pharmaceutical combination, comprising a therapeutically effective amount of the polypeptide according to the definition of anyone of formulae I to IX, or an amide, an ester or a salt thereof, and one or more therapeutically active agents selected from β-adrenergic receptor blockers such as acebutolol, atenolol, betaxolol, bisoprolol, metoprolol, nadolol, propranolol, sotalol and timolol; angiotensin II receptor antagonists such as AT1 blockers; antidiabetic agents such as DPPIV inhibitors (e.g. vildagliptin) and GLP1 peptide agonist.

The term "obesity-reducing agent" includes lipase inhibitors (e.g., orlistat) and appetite suppressants (e.g., sibutramine and phentermine).

An aldosterone synthase inhibitor or a pharmaceutically acceptable salt thereof is understood to be an active ingredient that has the property to inhibit the production of aldosterone. Aldosterone synthase (CYP11B2) is a mitochondrial cytochrome P450 enzyme catalyzing the last step of aldosterone production in the adrenal cortex, i.e., the conversion of 11-deoxycorticosterone to aldosterone. The inhibition of the aldosterone production with so-called aldosterone synthase inhibitors is known to be a successful variant to treatment of hypokalemia, hypertension, congestive heart failure, atrial fibrillation or renal failure. Such aldosterone synthase inhibition activity is readily determined by those skilled in the art according to standard assays (e.g., US 2007/0049616).

The class of aldosterone synthase inhibitors comprises both steroidal and non-steroidal aldosterone synthase inhibitors, the later being most preferred.

Preference is given to commercially available aldosterone synthase inhibitors or those aldosterone synthase inhibitors that have been approved by the health authorities.

The class of aldosterone synthase inhibitors comprises compounds having differing structural features. An example of non-steroidal aldosterone synthase inhibitor is the (+)-enantiomer of the hydrochloride of fadrozole (U.S. Pat. Nos. 4,617,307 and 4,889,861) of formula

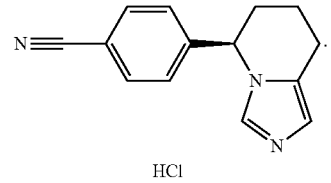 [SMILES: N#Cc1ccc([C@H]2CCCc3cncn32)cc1 ; Cl]

or, if appropriable, a pharmaceutically acceptable salt thereof.

Aldosterone synthase inhibitors useful in said combination are compounds and analogs generically and specifically disclosed e.g. in US2007/0049616, in particular in the compound claims and the final products of the working examples, the subject-matter of the final products, the pharmaceutical preparations and the claims are hereby incorporated into the present application by reference to this publication. Preferred aldosterone synthase inhibitors suitable for use in the present invention include, without limitation 4-(6,7-dihydro-5H-pyrrolo[1,2-c]imidazol-5-yl)-3-methyl-benzonitrile; 5-(2-chloro-4-cyanophenyl)-6,7-dihydro-5H-pyrrolo[1,2-c]imidazole-5-carboxylic acid (4-methoxybenzyl)methylamide; 4'-fluoro-6-(6,7,8,9-tetrahydro-5H-imidazo[1,5-a]azepin-5-yl)biphenyl-3-carbonitrile; 5-(4-Cyano-2-methoxyphenyl)-6,7-dihydro-5H-pyrrolo[1,2-c]imidazole-5-carboxylic acid butyl ester; 4-(6,7-Dihydro-5H-pyrrolo[1,2-c]imidazol-5-yl)-2-methoxybenzonitrile; 5-(2-Chloro-4-cyanophenyl)-6,7-dihydro-5H-pyrrolo[1,2-c] imidazole-5-carboxylic acid 4-fluorobenzyl ester; 5-(4-Cyano-2-trifluoromethoxyphenyl)-6,7-dihydro-5H-pyrrolo[1,2-c]imidazole-5-carboxylic acid methyl ester; 5-(4-

Cyano-2-methoxyphenyl)-6,7-dihydro-5H-pyrrolo[1,2-c]imidazole-5-carboxylic acid 2-isopropoxyethyl ester; 4-(6,7-Dihydro-5H-pyrrolo[1,2-c]imidazol-5-yl)-2-methylbenzonitrile; 4-(6,7-dihydro-5H-pyrrolo[1,2-c]imidazol-5-yl)-3-fluorobenzonitrile; 4-(6,7-Dihydro-5H-pyrrolo[1,2-c]imidazol-5-yl)-2-methoxybenzonitrile; 3-Fluoro-4-(7-methylene-6,7-dihydro-5H-pyrrolo[1,2-c]imidazol-5-yl)benzonitrile; cis-3-Fluoro-4-[7-(4-fluoro-benzyl)-5,6,7,8-tetrahydro-imidazo[1,5-a]pyridin-5-yl]benzonitrile; 4'-Fluoro-6-(9-methyl-6,7,8,9-tetrahydro-5H-imidazo[1,5-a]azepin-5-yl)biphenyl-3-carbonitrile; 4'-Fluoro-6-(9-methyl-6,7,8,9-tetrahydro-5H-imidazo[1,5-a]azepin-5-yl)biphenyl-3-carbonitrile or in each case, the (R) or (S) enantiomer thereof; or if appropriable, a pharmaceutically acceptable salt thereof.

The term aldosterone synthase inhibitors also include compounds and analogs disclosed in WO2008/076860, WO2008/076336, WO2008/076862, WO2008/027284, WO2004/046145, WO2004/014914, WO2001/076574.

Furthermore Aldosterone synthase inhibitors also include compounds and analogs disclosed in U.S. patent applications US2007/0225232, US2007/0208035, US2008/0318978, US2008/0076794, US2009/0012068, US20090048241 and in PCT applications WO2006/005726, WO2006/128853, WO2006128851, WO2006/128852, WO2007065942, WO2007/116099, WO2007/116908, WO2008/119744 and in European patent application EP 1886695. Preferred aldosterone synthase inhibitors suitable for use in the present invention include, without limitation 8-(4-Fluorophenyl)-5,6-dihydro-8H-imidazo[5,1-c][1,4]oxazine; 4-(5,6-Dihydro-8H-imidazo[5,1-c][1,4]oxazin-8-yl)-2-fluorobenzonitrile; 4-(5,6-Dihydro-8H-imidazo[5,1-c][1,4]oxazin-8-yl)-2,6-difluorobenzonitrile; 4-(5,6-Dihydro-8H-imidazo[5,1-c][1,4]oxazin-8-yl)-2-methoxybenzonitrile; 3-(5,6-Dihydro-8H-imidazo[5,1-c][1,4]oxazin-8-yl)benzonitrile; 4-(5,6-Dihydro-8H-imidazo[5,1-c][1,4]oxazin-8-yl)phthalonitrile; 4-(8-(4-Cyanophenyl)-5,6-dihydro-8H-imidazo[5,1-c][1,4]oxazin-8-yl)benzonitrile; 4-(5,6-Dihydro-8H-imidazo[5,1-c][1,4]oxazin-8-yl)benzonitrile; 4-(5,6-Dihydro-8H-imidazo[5,1-c][1,4]oxazin-8-yl)naphthalene-1-carbonitrile; 8-[4-(1H-Tetrazol-5-yl)phenyl]-5,6-dihydro-8H-imidazo[5,1-c][1,4]oxazine as developed by Speedel or in each case, the (R) or (S) enantiomer thereof; or if appropriable, a pharmaceutically acceptable salt thereof.

Aldosterone synthase inhibitors useful in said combination are compounds and analogs generically and specifically disclosed e.g. in WO 2009/156462 and WO 2010/130796, in particular in the compound claims and the final products of the working examples, the subject-matter of the final products, the pharmaceutical preparations and the claims. Preferred Aldosterone Synthase inhibitors suitable for combination in the present invention include, 3-(6-Fluoro-3-methyl-2-pyridin-3-yl-1H-indol-1-ylmethyl)-benzonitrile hydrochloride, 1-(4-Methanesulfonyl-benzyl)-3-methyl-2-pyridin-3-yl-1H-indole, 2-(5-Benzyloxy-pyridin-3-yl)-6-chloro-1-methyl-1H-indole, 5-(3-Cyano-1-methyl-1H-indol-2-yl)-nicotinic acid ethyl ester, N[5-(6-chloro-3-cyano-1-methyl-1H-indol-2-yl)-pyridin-3-ylmethyl]-ethanesulfonamide, Pyrrolidine-1-sulfonic acid 5-(6-chloro-3-cyano-1-methyl-1H-indol-2-yl)-pyridin-3-yl ester, N-Methyl-N-[5-(1-methyl-1H-indol-2-yl)-pyridin-3-ylmethyl]-methanesulfonamide, 6-Chloro-1-methyl-2-{5-[(2-pyrrolidin-1-yl-ethylamino)-methyl]-pyridin-3-yl}-1H-indole-3-carbonitrile, 6-Chloro-2-[5-(4-methanesulfonyl-piperazin-1-ylmethyl)-pyridin-3-yl]-1-methyl-1H-indole-3-carbonitrile, 6-Chloro-1-methyl-2-{5-[(1-methyl-piperidin-4-ylamino)-methyl]-pyridin-3-yl}-1H-indole-3-carbonitrile, Morpholine-4-carboxylic acid [5-(6-chloro-3-cyano-1-methyl-1H-indol-2-yl)-pyridin-3-ylmethyl]-amide, N-[5-(6-Chloro-1-methyl-1H-indol-2-yl)-pyridin-3-ylmethyl]-ethanesulfonamide, C,C,C-Trifluoro-N-[5-(1-methyl-1H-indol-2-yl)-pyridin-3-ylmethyl]-methanesulfonamide, N-[5-(3-Chloro-4-cyano-phenyl)-pyridin-3-yl]-4-trifluoromethyl-benzenesulfonamide, N-[5-(3-Chloro-4-cyano-phenyl)-pyridin-3-yl]-1-phenyl-methanesulfonamide, N-(5-(3-chloro-4-cyanophenyl)pyridin-3-yl)butane-1-sulfonamide, N-(1-(5-(4-cyano-3-methoxyphenyl)pyridin-3-yl)ethyl)ethanesulfonamide, N-((5-(3-chloro-4-cyanophenyl)pyridin-3-yl)(cyclopropyl)methyl)ethanesulfonamide, N-(cyclopropyl (5-(1H-indol-5-yl)pyridin-3-yl)methyl)ethanesulfonamide, N-(cyclopropyl(5-naphtalen-1-yl-pyridin-3-yl)methyl)ethanesulfonamide, Ethanesulfonic acid [5-(6-chloro-1-methyl-1H-pyrrolo[2,3-b]pyridin-2-yl)-pyridin-3-ylmethyl]-amide and Ethanesulfonic acid {[5-(3-chloro-4-cyano-phenyl)-pyridin-3-yl]-cyclopropyl-methyl}-ethyl-amide.

The term "endothelin receptor blocker" includes bosentan and ambrisentan.

The term "CETP inhibitor" refers to a compound that inhibits the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). Examples include compounds disclosed in U.S. Pat. No. 6,140,343 and U.S. Pat. No. 6,197,786 (e.g., [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester (torcetrapib); compounds disclosed in U.S. Pat. No. 6,723,752 (e.g., (2R)-3-{[3-(4-Chloro-3-ethyl-phenoxy)-phenyl]-[[3-(1,1,2,2-tetrafluoro-ethoxy)-phenyl]-methyl]- amino}-1,1,1-trifluoro-2-propanol); compounds disclosed in U.S. patent application Ser. No. 10/807,838; polypeptide derivatives disclosed in U.S. Pat. No. 5,512,548; rosenonolactone derivatives and phosphate-containing analogs of cholesteryl ester disclosed in J. Antibiot., 49(8): 815-816 (1996), and Bioorg. Med. Chem. Lett.; 6:1951-1954 (1996), respectively. Furthermore, the CETP inhibitors also include those disclosed in WO2000/017165, WO2005/095409, WO2005/097806, WO 2007/128568, WO2008/009435, WO 2009/059943 and WO2009/071509.

The term "NEP inhibitor" refers to a compound that inhibits neutral endopeptidase (NEP) EC 3.4.24.11. Examples include Candoxatril, Candoxatrilat, Dexecadotril, Ecadotril, Racecadotril, Sampatrilat, Fasidotril, Omapatrilat, Gemopatrilat, Daglutril, SCH-42495, SCH-32615, UK-447841, AVE-0848, PL-37 and and (2R,4S)-5-Biphenyl-4-yl-4-(3-carboxy-propionylamino)-2-methyl-pentanoic acid ethyl ester or a pharmaceutically acceptable salt thereof. NEP inhibitors also include Phosphono/biaryl substituted dipeptide derivatives, as disclosed in U.S. Pat. No. 5,155,100. NEP inhibitors also include N-mercaptoacyl phenylalanine derivative as disclosed in PCT application Number WO 2003/104200. NEP inhibitors also include dual-acting antihypertensive agents as disclosed in PCT application Numbers WO 2008/133896, WO 2009/035543 or WO 2009/134741. Other examples include compounds disclosed in U.S. application Ser. Nos. 12/788,794; 12/788,766 and 12/947,029. NEP inhibitors also include compounds disclosed in WO 2010/136474, WO 2010/136493, WO 2011/061271 and US provisional applications Nos. 61/414,171 and 61/414,163.

In one embodiment, the invention provides a method of activating the APJ receptor in a subject, wherein the method comprises administering to the subject a therapeutically effective amount of the polypeptide according to the definition of anyone of formulae I to IX, or an amide, an ester or a salt thereof.

In one embodiment, the invention provides a method of treating a disorder or a disease responsive to the activation of the APJ receptor, in a subject, wherein the method comprises administering to the subject a therapeutically effective amount of the polypeptide according to the definition of anyone of formulae I to IX, or an amide, an ester or a salt thereof.

In one embodiment, the invention provides a method of treating a disorder or a disease responsive to the activation (agonism) of the APJ receptor, in a subject, wherein the disorder or the disease is selected from acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

In one embodiment, the invention provides a polypeptide according to the definition of anyone of formulae I to IX, for use as a medicament.

In one embodiment, the invention provides the use of a polypeptide according to the definition of anyone of formulae I to IX, or an amide, an ester or a salt thereof, in the manufacture of a medicament, for the treatment of a disorder or disease responsive to the activation of the APJ receptor. In another embodiment, the invention provides the use of a polypeptide according to the definition of anyone of formulae I to IX, or an amide, an ester or a salt thereof, in the manufacture of a medicament, for the treatment of a disorder or disease responsive to the activation of the APJ receptor, wherein said disorder or disease is in particular selected from acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

Exemplification of the Invention: Peptide and Polypeptide Synthesis

| Abbreviation | Definition |
|---|---|
| AA | Amino acid |
| Ac | Acetyl |
| Acm | Acetamidomethyl |
| ACN | Acetonitrile |
| AcOH | Acetic acid |
| $Ac_2O$ | Acetic anhydride |
| AM | Aminomethyl |
| BAL | Backbone amide linker |
| BSA | Bovine Serum Albumin |
| Boc | tert-Butyloxycarbonyl |
| DCM | Dichlormethane |
| DIC | N,N'-Diisopropylcarbodiimide |
| DIPEA | N,N'-Diisopropylethylamine |
| DMA | N,N'-Dimethylacetamide |
| DMF | N,N'-Dimethylformamide |
| DMSO | Dimethylsulfoxide |
| DVB | Divinylbenzene |
| EDT | Ethanedithiol |
| FA | Formic acid |
| Fmoc | 9-Fluorenylmethyloxycarbonyl |
| HATU | 2-(1H-9-Azabenzotriazole-1-yl)-1,1,3,3-tetramethyluronium hexafluorophosphate |
| HBSS | Hank's buffered salt solution |
| HCTU | 2-(6-Chloro-1H-Benzotriazole-yl)-1,1,3,3-tetramethyluronium hexafluorophosphate |
| HEPES | 4-(2-hydroxyethyl)-1-piperazineethanesulfonic acid |
| HFIP | Hexafluoroisopropanol |
| HOAt | 1-Hydroxy-7-azabenzotriazole |
| HPLC | High performance liquid chromatography |
| ivDde | (4,4-Dimethyl-2,6-dioxocyclohex-1-ylidene)-3-methylbutyl |
| LN | Logarithmus naturali (natural logarithm) |
| MeOH | Methanol |
| MS | Mass spectrometry |
| Nal | 2-Naphthylalanine |
| Nle | Norleucine |
| NMP | N-Methylpyrrolidine |
| Oxyma Pure | Ethyl 2-cyano-2-(hydroxyimino)acetate |
| Pbf | 2,2,4,6,7-Pentamethyldihydrobenzofuran-5-sulfonyl |
| pE | Pyroglutamate |
| PG | Protecting group |
| Ph | Phenyl |
| PS | Polystyrene |
| POL | Polymer support |
| rt | Room temperature |
| SPPS | Solid phase peptide synthesis |
| tBuOH | tert-Butanol |
| TFA | Trifluoroacetic acid |
| THF | Tetrahydrofuran |
| TIS | Triisopropylsilane |
| $t_R$ | Retention time |
| Trt | Trityl |
| UPLC | Ultra performance liquid chromatography |
| UV | Ultraviolet |

The peptides were synthesized by standard solid phase Fmoc chemistry. The peptides were assembled on the Prelude™ peptide synthesizer (Protein Technologies, Inc., Tucson, USA). Peptides with a free carboxylic acid on the C-terminus were synthesized from 2-chlorotrityl chloride-PS-resin (ABCR, Karlsruhe, Germany). Peptides with an unsubstituted carboxamide on the C-terminus were synthesized from Fmoc protected Rink-Amide-AM-PS-resin (Merck, Darmstadt, Germany). Peptides with an N-monosubstituted carboxamide on the C-terminus were synthesized from BAL-AM-PS-resin loaded with amines (EMC Microcollections, Tübingen, Germany).

The peptides were purified by preparative reversed-phase HPLC. The following columns were used:
- Waters SunFire Prep C18 OBD Column, 5 µm, 30×100 mm, Part No. 186002572 (one column or two columns in series)
- Waters SunFire Prep C18 OBD Column, 5 µm, 30×150 mm, Part No. 186002797
- Waters Atlantis Prep OBD T3 Column, 5 µm, 30×150 mm, Part No. 186003703
- Waters XBridge Prep C8 OBD Column, 5 µm, 30×150 mm, Part No. 186003083
- Machery-Nagel Nucleosil® 100-5 C18, 5 µm, 250×40 mm, Part No. 715340.400

Mobile phases consisted of eluent A (0.1% TFA in $H_2O$) and eluent B (ACN). Gradients were designed based on the specific requirements of the separation problem. Pure products were lyophilized from ACN/$H_2O$.

The products were analyzed by analytical HPLC using UV detection at λ=214 nm (Column: Bischoff UHC-640, 53×4.0 mm, ProntoSil 120-3-C18-H, 3 μm, Part No. 0604F185PS030) Mobile phases consisted of eluent A (0.07% TFA in $H_2O$) and eluent B (0.1% TFA in ACN). Additional characterization of the products was done by UPLC-MS (Column: Waters Acquity UPLC® BEH C18, 1.7 μm, 2.1×50 mm, Part No. 186002350) using electrospray ionization.

The peptides that are exemplified in Table 4 were synthesized using the general procedures described below. Unsubstituted N- or C-termini are indicated by small italic *H*— or —*OH*, respectively.

TABLE 4

| Example | Sequence | SEQ ID NO: | Type of Ring |
|---|---|---|---|
| Example 1 | *pE*-R-P-R-L-K-H-F-G-P-Nle-D-Phenethylamine | 8 | Lactam $K^6$-$D^{12}$ |
| Example 2 | *pE*-R-P-R-L-K-H-F-G-P-Nle-E-Phenethylamine | 9 | Lactam $K^6$-$E^{12}$ |
| Example 3 | *pE*-R-P-R-L-Orn-H-F-G-P-Nle-D-Phenethylamine | 10 | Lactam $O^6$-$D^{12}$ |
| Example 4 | *pE*-R-P-R-L-Dab-H-F-G-P-Nle-D-Phenethylamine | 11 | Lactam $Dab^6$-$D^{12}$ |
| Example 5 | *pE*-R-P-R-L-K-F-K-G-P-Nle-F | 12 | Lactam $K^6$-C-terminus |
| Example 6 | *pE*-R-P-R-L-K-F-K-G-P-Nle-f | 13 | Lactam $K^6$-C-terminus |
| Example 7 | Q-R-P-R-L-C-F-K-G-P-Nle-C-F-G-G | 14 | Lactam N-terminus-C-terminus, Disulfide $C^6$-$C^{12}$ |
| Example 8 | *pE*-R-P-R-L-C-H-K-G-P-Nle-C-F-*OH* | 15 | Disulfide $C^6$-$C^{12}$ |
| Example 9 | *pE*-R-P-R-L-C-Aib-K-G-P-Nle-C-F-*OH* | 16 | Disulfide $C^6$-$C^{12}$ |
| Example 10 | *pE*-R-P-R-L-C-Aib-K-G-P-Nle-C-f-*OH* | 17 | Disulfide $C^6$-$C^{12}$ |
| Example 11 | *H*-Isn-R-P-R-L-C-Aib-K-G-P-Nle-C-f-*OH* | 18 | Disulfide $C^6$-$C^{12}$ |
| Example 12 | *pE*-R-P-R-L-C-H-K-G-P-Nle-C-Phenethylamine | 19 | Disulfide $C^6$-$C^{12}$ |
| Example 13 | *pE*-R-P-R-L-C-H-K-G-P-Nle-C-f-*OH* | 20 | Disulfide $C^6$-$C^{12}$ |
| Example 14 | *pE*-R-P-R-Cha-C-H-K-G-P-Cha-C-F-*OH* | 21 | Disulfide $C^6$-$C^{12}$ |
| Example 15 | *pE*-R-P-R-L-C-F-K-G-P-Nle-C-F-*OH* | 22 | Disulfide $C^6$-$C^{12}$ |
| Example 16 | *H*-R-P-R-L-C-H-K-G-P-Nle-C-F-*OH* | 23 | Disulfide $C^6$-$C^{12}$ |
| Example 17 | *H*-R-R-P-R-L-C-H-K-G-P-Nle-C-F-*OH* | 24 | Disulfide $C^6$-$C^{12}$ |
| Example 18 | *H*-Isn-R-P-R-L-C-H-K-G-P-Nle-C-F-*OH* | 25 | Disulfide $C^6$-$C^{12}$ |
| Example 19 | *pE*-R-P-R-L-C-H-F-G-P-Nle-C-Phenethylamine | 26 | Disulfide $C^6$-$C^{12}$ |
| Example 20 | *pE*-R-P-R-L-C-H-K-Aib-P-Nle-C-F-*OH* | 27 | Disulfide $C^6$-$C^{12}$ |
| Example 21 | *pE*-R-P-R-L-C-H-(4-$NH_2$-Isn)-G-P-Nle-C-F-*OH* | 28 | Disulfide $C^6$-$C^{12}$ |
| Example 22 | *pE*-R-P-R-L-C-H-K-G-P-Nle-C-K(Palmitoyl)-*OH* | 29 | Disulfide $C^6$-$C^{12}$ |
| Example 23 | *pE*-R-P-R-L-C-K(Palmitoyl)-K-G-P-Nle-C-F-*OH* | 30 | Disulfide $C^6$-$C^{12}$ |
| Example 24 | Palmitoyl-O2Oc-Q-R-P-R-L-C-H-K-G-P-Nle-C-F-*OH* | 31 | Disulfide $C^6$-$C^{12}$ |
| Example 25 | Lauroyl-O2Oc-Q-R-P-R-L-C-H-K-G-P-Nle-C-F-*OH* | 32 | Disulfide $C^6$-$C^{12}$ |
| Example 26 | *pE*-R-P-R-L-C-H-K-G-P-Nle-C-K(Lauroyl)-*OH* | 33 | Disulfide $C^6$-$C^{12}$ |
| Example 27 | *pE*-R-P-R-L-C-K(Lauroyl)-K-G-P-Nle-C-F-*OH* | 34 | Disulfide $C^6$-$C^{12}$ |
| Example 28 | *pE*-R-P-C-L-C-C-K-G-P-Nle-C-F-*OH* | 35 | Disulfides $C^6$-$C^{12}$, $C^4$-$C^7$ |
| Example 29 | *pE*-R-C-R-L-C-C-K-G-P-Nle-C-F-*OH* | 36 | Disulfides $C^6$-$C^{12}$, $C^3$-$C^7$ |
| Example 30 | *pE*-r-P-R-L-C-H-K-G-P-Nle-C-F-*OH* | 37 | Disulfide $C^6$-$C^{12}$ |

TABLE 4-continued

| Example | Sequence | SEQ ID NO: | Type of Ring |
|---|---|---|---|
| Example 31 | pE-F-P-R-L-C-H-K-G-P-Nle-C-F-OH | 38 | Disulfide $C^6$-$C^{12}$ |
| Example 32 | pE-E-P-R-L-C-H-K-G-P-Nle-C-F-OH | 39 | Disulfide $C^6$-$C^{12}$ |
| Example 33 | pE-R-p-R-L-C-H-K-G-P-Nle-C-F-OH | 40 | Disulfide $C^6$-$C^{12}$ |
| Example 34 | pE-R-K-R-L-C-H-K-G-P-Nle-C-F-OH | 41 | Disulfide $C^6$-$C^{12}$ |
| Example 35 | pE-R-D-R-L-C-H-K-G-P-Nle-C-F-OH | 42 | Disulfide $C^6$-$C^{12}$ |
| Example 36 | pE-R-P-F-L-C-H-K-G-P-Nle-C-F-OH | 43 | Disulfide $C^6$-$C^{12}$ |
| Example 37 | pE-R-P-R-K-C-H-K-G-P-Nle-C-F-OH | 44 | Disulfide $C^6$-$C^{12}$ |
| Example 38 | pE-R-P-R-L-C-H-E-G-P-Nle-C-F-OH | 45 | Disulfide $C^6$-$C^{12}$ |
| Example 39 | pE-R-P-R-L-C-H-K-D-P-Nle-C-F-OH | 46 | Disulfide $C^6$-$C^{12}$ |
| Example 40 | pE-R-P-E-L-C-H-K-G-P-Nle-C-F-OH | 47 | Disulfide $C^6$-$C^{12}$ |
| Example 41 | pE-R-P-R-(4-PhF)-C-H-K-G-P-Nle-C-F-OH | 48 | Disulfide $C^6$-$C^{12}$ |
| Example 42 | pE-R-P-R-D-C-H-K-G-P-Nle-C-F-OH | 49 | Disulfide $C^6$-$C^{12}$ |
| Example 43 | pE-R-P-R-L-C-E-K-G-P-Nle-C-F-OH | 50 | Disulfide $C^6$-$C^{12}$ |
| Example 44 | pE-R-P-R-L-C-H-K-L-P-Nle-C-F-OH | 51 | Disulfide $C^6$-$C^{12}$ |
| Example 45 | pE-R-P-R-L-C-H-K-R-P-Nle-C-F-OH | 52 | Disulfide $C^6$-$C^{12}$ |
| Example 46 | pE-R-P-R-L-C-H-K-G-(Pipecolic acid)-Nle-C-F-OH | 53 | Disulfide $C^6$-$C^{12}$ |
| Example 47 | pE-R-P-R-L-C-H-K-G-P-(3-PyA)-C-F-OH | 54 | Disulfide $C^6$-$C^{12}$ |
| Example 48 | pE-R-P-R-L-C-H-K-G-P-Nle-C-H-OH | 55 | Disulfide $C^6$-$C^{12}$ |
| Example 49 | pE-R-P-R-L-C-H-K-G-P-Nle-C-E-OH | 56 | Disulfide $C^6$-$C^{12}$ |
| Example 50 | pE-R-P-R-L-C-H-K-G-P-Nle-C-OH | 57 | Disulfide $C^6$-$C^{12}$ |
| Example 51 | pE-R-P-R-L-C-H-K-G-P-Nle-hC-F-OH | 58 | Disulfide $C^6$-$C^{12}$ |
| Example 52 | pE-R-P-R-L-hC-H-K-G-P-Nle-hC-F-OH | 59 | Disulfide $C^6$-$C^{12}$ |
| Example 53 | pE-R-P-R-L-c-H-K-G-P-Nle-C-F-OH | 60 | Disulfide $C^6$-$C^{12}$ |
| Example 54 | pE-R-P-R-L-C-H-K-G-P-Nle-(D-hC)-F-OH | 61 | Disulfide $C^6$-$C^{12}$ |
| Example 55 | pE-R-P-R-L-(D-hC)-H-K-G-P-Nle-(D-hC)-F-OH | 62 | Disulfide $C^6$-$C^{12}$ |
| Example 56 | pE-R-P-R-L-C-H-K-G-P-Nle-c-F-OH | 63 | Disulfide $C^6$-$C^{12}$ |
| Example 57 | pE-R-P-R-L-c-H-K-G-P-Nle-c-F-OH | 64 | Disulfide $C^6$-$C^{12}$ |
| Example 58 | Myristoyl-O2Oc-O2Oc-Q-R-P-R-L-C-H-K-G-P-Nle-C-f-OH | 65 | Disulfide $C^6$-$C^{12}$ |
| Example 59 | Myristoyl-O2Oc-O2Oc-O2Oc-Q-R-P-R-L-C-H-K-G-P-Nle-C-f-OH | 66 | Disulfide $C^6$-$C^{12}$ |
| Example 60 | Myristoyl-O2Oc-O2Oc-O2Oc-O2Oc-Q-R-P-R-L-C-H-K-G-P-Nle-C-f-OH | 67 | Disulfide $C^6$-$C^{12}$ |
| Example 61 | pE-R-P-R-L-C-H-K(Myristoyl)-G-P-Nle-C-F-OH | 68 | Disulfide $C^6$-$C^{12}$ |
| Example 62 | pE-R-P-R-L-C-H-K-G-P-Nle-C-F-$NH_2$ | 69 | Disulfide $C^6$-$C^{12}$ |
| Example 63 | pE-R-P-R-L-C-H-K-G-P-Nle-C-$NH_2$ | 70 | Disulfide $C^6$-$C^{12}$ |
| Example 64 | pE-R-P-R-L-C-H-K-G-P-Nle-C-F-OH | 71 | —S—$CH_2$—C(=O)$CH_2$—S— [$C^6$-$C^{12}$] |

TABLE 4-continued

| Example | Sequence | SEQ ID NO: | Type of Ring |
|---|---|---|---|
| Example 65 | pE-R-P-R-L-C-H-K-G-P-Nle-C-F-OH | 72 | Monosulfide $C^6$-$C^{12}$ |
| Example 66 | pE-R-P-R-L-C-H-K-G-P-Nle-C-F-OH | 73 | —S—$CH_2$—C(=Z)—$CH_2$—S— [$C^6$-$C^{12}$] |

Analytical Methods
1) HPLC—Analytical Method A
   Column: Bischoff UHC-640 (53×4.0 mm) with ProntoSil 120-3-C18-H, 3 μm; Part n°: 0604F185PS030
   Eluent A: 0.07% TFA in water/Eluent B: 0.1% TFA in ACN
   Flow: 1.5 ml/min
   Temperature: 40° C.
   Gradient:

| Time [min] | A [%] | B [%] |
|---|---|---|
| 0.0 | 90 | 10 |
| 9.5 | 0 | 100 |
| 12.0 | 0 | 100 |
| 12.2 | 90 | 10 |

2a) UPLC-MS—Analytic Method B
   Waters Acquity UPLC® BEH C18, 1.7 μm, 2.1×50 mm; Part n°: 186002350
   Eluent A: 0.1% FA in water; Eluent B: 0.1% FA in ACN
   Flow: 0.7 ml/min
   Temperature: 40° C.
   Gradient:

| Time [min] | A [%] | B [%] |
|---|---|---|
| 0.0 | 80 | 20 |
| 1.0 | 75 | 25 |
| 4.2 | 10 | 90 |
| 4.3 | 0 | 100 |
| 4.6 | 80 | 20 |

2b) UPLC-MS—Analytic Method C
   Waters Acquity UPLC® BEH C18, 1.7 μm, 2.1×50 mm; Part n°: 186002350
   Eluent A: 0.1% FA in water; Eluent B: 0.1% FA in ACN
   Flow: 0.7 ml/min
   Temperature: 40° C.
   Gradient:

| Time [min] | A [%] | B [%] |
|---|---|---|
| 0.0 | 99 | 1 |
| 1.0 | 97 | 3 |
| 3.5 | 50 | 50 |
| 4.0 | 10 | 90 |
| 4.3 | 0 | 100 |
| 4.6 | 80 | 20 |

The analytical data for peptides of Examples 1 to 63 are summarized in Table 5 and was generated using the analytical methods described supra.

TABLE 5

| | HPLC | | Mass spectrometry | | | | |
|---|---|---|---|---|---|---|---|
| Peptide | $t_R$ [min] | Meth. | $[M+2H]^{2+}$ (measured) | $[M+3H]^{3+}$ (measured) | Meth. | $[M+2H]^{2+}$ (calc.) | $[M+3H]^{3+}$ (calc.) |
| Example 1 | 4.16 | A | 766.3 | 511.2 | C | 766.4 | 511.3 |
| Example 2 | 4.18 | A | 773.5 | 515.8 | C | 773.4 | 516.0 |
| Example 3 | 4.14 | A | | 506.6 | C | 759.4 | 506.6 |
| Example 4 | 4.15 | A | 752.4 | 501.9 | C | 752.4 | 501.9 |
| Example 5 | 3.70 | A | | 484.5 | C | 726.4 | 484.6 |
| Example 6 | 3.84 | A | | 484.5 | C | 726.4 | 484.6 |
| Example 7 | 3.85 | A | | 553.6 | C | 829.9 | 553.6 |
| Example 8 | 3.43 | A | 768.1 | 512.4 | C | 768.4 | 512.6 |
| Example 9 | 3.77 | A | | 495.2 | C | 742.4 | 495.3 |
| Example 10 | 3.74 | A | 742.5 | 495.1 | C | 742.4 | 495.3 |
| Example 11 | 3.61 | A | 742.9 | 495.2 | C | 742.4 | 495.3 |
| Example 12 | 3.62 | A | | 497.8 | C | 746.4 | 497.9 |
| Example 13 | 3.49 | A | 768.3 | 512.5 | C | 768.4 | 512.6 |
| Example 14 | 4.14 | A | 808.5 | 539.2 | C | 808.4 | 539.3 |
| Example 15 | 3.99 | A | 773.4 | 515.8 | C | 773.4 | 515.9 |
| Example 16 | 3.36 | A | | 475.5 | C | 712.9 | 475.6 |
| Example 17 | 3.28 | A | | 527.5 | C | 790.9 | 527.6 |
| Example 18 | 3.36 | A | | 512.5 | C | 768.4 | 512.6 |
| Example 19 | 4.38 | A | 756.0 | 504.2 | C | 755.9 | 504.3 |
| Example 20 | 3.17 | A | 782.6 | 522.0 | C | 782.4 | 521.9 |
| Example 21 | 3.45 | A | | 512.0 | C | 767.4 | 511.9 |
| Example 22 | 6.12 | A | | 585.6 | B | 878.0 | 585.7 |
| Example 23 | 6.46 | A | 883.2 | 588.9 | B | 883.0 | 589.0 |
| Example 24 | 5.20 | A | | 646.0 | B | 968.6 | 646.0 |
| Example 25 | 5.18 | A | | 627.3 | B | 940.5 | 627.3 |
| Example 26 | 5.11 | A | | 567.0 | B | 850.0 | 567.0 |
| Example 27 | 5.44 | A | | 570.0 | B | 855.0 | 570.3 |
| Example 28 | 4.16 | A | 723.7 | | C | 723.8 | 482.9 |

TABLE 5-continued

|  | HPLC | | Mass spectrometry | | | | |
|---|---|---|---|---|---|---|---|
|  |  |  | [M + 2H]$^{2+}$ | [M + 3H]$^{3+}$ |  | [M + 2H]$^{2+}$ | [M + 3H]$^{3+}$ |
| Peptide | $t_R$ [min] | Meth. | (measured) | (measured) | Meth. | (calc.) | (calc.) |
| Example 29 | 3.85 | A | 753.0 | 502.5 | C | 753.3 | 502.6 |
| Example 30 | 3.39 | A |  | 512.5 | C | 768.4 | 512.6 |
| Example 31 | 4.08 | A | 763.8 | 509.4 | C | 763.9 | 509.6 |
| Example 32 | 3.59 | A | 754.8 | 503.6 | C | 754.9 | 503.6 |
| Example 33 | 3.36 | A |  | 512.5 | C | 768.4 | 512.6 |
| Example 34 | 3.14 | A |  | 522.8 | C | 783.9 | 522.9 |
| Example 35 | 3.36 | A |  | 518.5 | C | 777.4 | 518.6 |
| Example 36 | 3.91 | A | 763.8 | 509.4 | C | 763.9 | 509.6 |
| Example 37 | 3.05 | A |  | 517.5 | C | 775.9 | 517.6 |
| Example 38 | 3.67 | A | 768.7 | 512.8 | C | 768.9 | 512.9 |
| Example 39 | 3.47 | A |  | 531.7 | C | 797.4 | 531.9 |
| Example 40 | 3.60 | A | 754.9 | 503.6 | C | 754.9 | 503.6 |
| Example 41 | 3.91 | A |  | 549.1 | C | 823.4 | 549.3 |
| Example 42 | 3.10 | A | 769.2 | 513.1 | C | 769.4 | 513.2 |
| Example 43 | 3.58 | A | 764.2 | 509.7 | C | 764.4 | 509.9 |
| Example 44 | 3.82 | A |  | 531.1 | C | 796.4 | 531.3 |
| Example 45 | 3.16 | A |  | 545.5 | C | 817.9 | 545.6 |
| Example 46 | 3.54 | A |  | 517.1 | C | 775.4 | 517.3 |
| Example 47 | 2.53 | A |  | 524.1 | C | 785.9 | 524.3 |
| Example 48 | 2.49 | A |  | 509.2 | C | 763.4 | 509.3 |
| Example 49 | 2.73 | A | 759.3 | 506.5 | C | 759.4 | 506.6 |
| Example 50 | 2.72 | A | 694.5 |  | C | 694.8 | 463.6 |
| Example 51 | 3.38 | A |  | 517.1 | C | 775.4 | 517.3 |
| Example 52 | 3.45 | A |  | 521.9 | C | 782.4 | 521.9 |
| Example 53 | 3.52 | A | 768.4 | 512.5 | C | 768.4 | 512.6 |
| Example 54 | 3.43 | A | 775.3 | 517.1 | C | 775.4 | 517.3 |
| Example 55 | 3.83 | A | 782.3 | 521.8 | C | 782.4 | 521.9 |
| Example 56 | 3.42 | A | 768.1 | 512.4 | C | 768.4 | 512.6 |
| Example 57 | 3.66 | A | 768.3 | 512.4 | C | 768.4 | 512.6 |
| Example 58 | 5.68 | A |  | 685.0 | B | 1027.1 | 685.0 |
| Example 59 | 5.58 | A |  | 733.4 | B | 1099.6 | 733.4 |
| Example 60 | 5.55 | A |  | 781.8 | B | 1172.1 | 781.8 |
| Example 61 | 3.18 | D | 874.5 | 582.9 | D | 873.5 | 585.7 |
| Example 62 | 3.22 | A |  | 512.3 | C | 767.9 | 512.3 |
| Example 63 | 2.71 | A | 694.3 | 463.1 | C | 694.4 | 463.2 |

General Synthesis Procedures

1) Loading of First Amino Acid onto 2-chlorotrityl chloride Resin and Fmoc-Removal 2-Chlorotrityl chloride resin (1 eq., 1.0-1.6 mmol/g) was washed thoroughly with DCM. The desired amino acid (typically 0.5-2 eq. relative to the resin, considering 1.6 mmol/g loading) was dissolved in DCM (approx. 10 mL per gram of resin) and DIPEA (4 eq. relative to the resin, considering 1.6 mmol/g loading). The solution was added to the resin and the suspension was shaken at rt for 19 h. The resin was drained and then thoroughly washed sequentially with DCM/MeOH/DIPEA (17:2:1), DCM, DMA, DCM.

For Fmoc removal and determination of the loading the resin was shaken repeatedly with piperidine/DMA (1:4) or 4-methylpiperidine/DMA (1:4) (12×10 mL per gram of initial resin) and washed with DMA (2×10 mL per gram of initial resin). The combined solutions were diluted with MeOH to a volume V of 250 mL per gram of initial resin. A 2 mL aliquot ($V_a$) of this solution was diluted further to 250 mL ($V_t$) with MeOH. The UV absorption was measured at 299.8 nm against a reference of MeOH, giving absorption A. The resin was thoroughly washed sequentially with DMA, DCM, DMA, DCM and dried in high vacuum at 40° C., affording m g of resin.

The loading of the resin is calculated according to the formula:

$$\text{Loading [mol/g]} = (A \times V_t \times V)/(d \times \varepsilon \times V_a \times m)$$

(with d: width of cuvette; $\varepsilon = 7800$ L mol$^{-1}$ cm$^{-1}$)

2) Solid Phase Peptide Synthesis on Prelude™ Synthesizer

2a) Synthesis Cycle A

The resin was washed with DMA. Fmoc was removed by repetitive treatment with 4-methylpiperidine/DMA (1:4). The resin was washed with DMA. Coupling was done by addition of the Fmoc-amino acid (3 eq.; 0.2 M solution in NMP), HCTU (3 eq.; 0.3 M solution in NMP), and DIPEA (3.3 eq.; 0.66 M solution in NMP) followed by mixing of the suspension with nitrogen at rt for typically 15 min to 4 h depending on the specific requirements. After washing with DMA the coupling step was typically repeated 1 to 3 times depending on the specific requirements. After washing with DMA capping was performed by addition of a mixture of Ac$_2$O/pyridine/DMA (1:1:8) and subsequent mixing of the suspension at rt. The resin was washed with DMA.

2b) Synthesis Cycle B

The resin was washed with DMA. Fmoc was removed by repetitive treatment with piperidine/DMA (1:4). The resin was washed with DMA. Coupling was done by addition of the Fmoc-amino acid (3 eq.; 0.3 M solution in NMP), HCTU (3 eq.; 0.3 M solution in NMP), and DIPEA (4.5 eq.; 0.9 M solution in NMP) followed by mixing of the suspension with nitrogen at rt for typically 15 min to 4 h depending on the specific requirements. After washing with DMA the coupling step was typically repeated 1 to 3 times depending on the specific requirements. After washing with DMA capping was performed by addition of a mixture of Ac$_2$O/pyridine/DMA (1:1:8) and subsequent mixing of the suspension at rt. The resin was washed with DMA.

2c) Synthesis Cycle C

The resin was washed with DMA. Fmoc was removed by repetitive treatment with piperidine/DMA (1:4). The resin was washed with DMA. Coupling was done by addition of the Fmoc-amino acid (3 eq.; 0.3 M solution in NMP), HCTU (3 eq.; 0.3 M solution in NMP), and DIPEA (6 eq.; 0.9 M solution in NMP) followed by mixing of the suspension with nitrogen at rt for typically 15 min to 4 h depending on the specific requirements. After washing with DMA the coupling step was typically repeated 1 to 3 times depending on the specific requirements.

After washing with DMA capping was performed by addition of a mixture of Ac$_2$O/pyridine/DMA (1:1:8) and subsequent mixing of the suspension at rt. The resin was washed with DMA.

2d) Synthesis Cycle D

The resin was washed with DMA. Fmoc was removed by repetitive treatment with 4-methylpiperidine/DMA (1:4). The resin was washed with DMA. Coupling was done by addition of a mixture of the Fmoc-amino acid and Oxyma Pure (3 eq. each; 0.2 M of both in NMP) and DIC (3 eq.; 0.3 M solution in NMP) followed by mixing of the suspension with nitrogen at rt for typically 15 min to 4 h depending on the specific requirements. After washing with DMA the coupling step was typically repeated 1 to 3 times depending on the specific requirements. After washing with DMA capping was performed by addition of a mixture of Ac$_2$O/pyridine/DMA (1:1:8) and subsequent mixing of the suspension at rt. The resin was washed with DMA.

3) Cleavage from Resin with or without Concomitant Removal of Protecting Groups 3a) Cleavage Method A The resin (0.1 mmol) was shaken at rt for 2 h with 95% aq. TFA/EDT/TIS (95:2.5:2.5) (3 mL). The cleavage solution was filtered off, and fresh solution was added (3 mL). The suspension was shaken at rt for 1 h then the cleavage solution was filtered off. Fresh solution was added (3 mL) and the suspension was shaken at rt for 1 h. The cleavage solution was filtered off. The combined cleavage solutions were poured slowly onto a mixture of cold heptane/diethyl ether (1:1) (35 mL), giving a precipitate. The suspension was centrifuged and the supernatant poured off. The residue was washed with cold heptane/diethyl ether (1:1) (10 mL), the suspension was centrifuged and the supernatant was poured off. The solid was dried in high vacuum.

3b) Cleavage Method B

The resin (0.1 mmol) was treated with 95% aq. TFA/EDT (4:1) (0.75 mL) and the suspension was shaken at rt for 1 h. A mixture of 95% aq. TFA (2.18 mL) and TIS (75 µL) was added and shaking at rt was resumed for 1 h. The cleavage solution was filtered off then 95% aq. TFA/EDT/TIS (95:2.5:2.5) (3 mL) was added to the resin and the suspension was shaken at rt for 1 h. The cleavage solution was filtered off and collected and fresh solution was added (3 mL). The suspension was shaken at rt for 1 h then the cleavage solution was filtered off. The combined cleavage solutions were poured onto cold heptane/diethyl ether (1:1) (35 mL). The precipitate thus formed was left to settle, centrifuged then the supernatant was carefully poured off. The precipitate was washed once with cold heptane/diethyl ether (1:1) (10 mL), the suspension was centrifuged and the supernatant was poured off. The residue was dried in high vacuum.

3c) Cleavage Method C

HFIP/DCM (30:70) (5 mL) was added to the resin (0.1 mmol) and the suspension was stirred at rt for 1.5 h. The cleavage solution was filtered off and collected and fresh HFIP/DCM (30:70) (5 mL) was added. The suspension was stirred at rt for 30 min. The cleavage solution was filtered off and collected. The resin was washed with DCM (2×5 mL) which was also collected. The combined cleavage and washing solutions were concentrated to dryness in high vacuum. The residue was lyophilized from tBuOH/H$_2$O (1:1).

4) Cyclization Methods

4a) Cyclization Method A (Disulfide Formation)

The fully deprotected linear precursor peptide was dissolved in H$_2$O/DMSO (9:1) or (4:1) to give typically a concentration of 1-15 mg/mL. The reaction mixture was then stirred at rt for typically 40 h depending on the requirements and then concentrated to dryness in high vacuum.

4b) Cyclization Method B (Disulfide Formation)

The fully deprotected linear precursor peptide (1 eq.) was dissolved in H$_2$O to give typically a concentration of 10 mg/mL. A solution of 50 mM I$_2$ in AcOH (1.2 eq.) was added in one portion to the stirred solution and the reaction was stirred for 10 min at rt. 0.5 M Ascorbic acid in H$_2$O (1.5 eq) was added to quench the excess of I$_2$. The solution was concentrated to near dryness in vacuo.

4c) Cyclization Method C (Selective Formation of Two Disulfides)

The partially protected linear precursor peptide (1 eq.) (two cysteines were protected with Acm and two cysteines unprotected) was dissolved in AcOH/H$_2$O (4:1) to give typically a concentration of 1 mg/mL. 50 mM I$_2$ in AcOH (2 eq.) was added and the reaction mixture was stirred at rt for 1 h. Further 50 mM I$_2$ in AcOH (10 eq.) was added portionwise over 4 h. After 21 h, the reaction mixture was concentrated to near dryness in vacuoand 1 M ascorbic acid in H$_2$O was added in excess to quench unreacted I$_2$.

4d) Cyclization Method D (Lactam Formation Between Side Chains)

The fully deprotected linear precursor peptide (1 eq.) and HATU (1.5 eq.) were dissolved in NMP (peptide concentration: typically) mmol/L). DIPEA (3 eq.) was added and the solution stirred at rt for 90 min. The reaction mixture was concentrated to dryness in vacuo.

4e) Cyclization Method E (Lactam Formation Between Side Chain and C-Terminus)

A solution of the peptide (1 eq.), HATU (1.3 eq.) and HOAt (1.3 eq.) in DMF (peptide concentration: 2.6 mmol/L) was treated with 2,6-lutidine (20 eq.) and the reaction was stirred at rt for 2 h. The reaction mixture was concentrated to dryness in vacuo.

In the following the syntheses of representative examples are described.

Example 1 Synthesis of pE-R-P-R-L-K-H-F-G-P-Nle-D-Phenethylamine (SEQ ID NO: 8) (lactam K$^6$-D$^{12}$) Example 1 below discloses SEQ ID NO: 8

H-N(Phenethyl)-POL

↓SPPS pE-R(Pbf)-P-R(Pbf)-L-K(Boc)-H(Trt)-F-G-P-Nle-D(tBu)-N(Phenethyl)-POL (1a)

1. Cleavage/PG Removal
2. Purification pE-R-P-R-L-K-H-F-G-P-Nle-D-NH(Phenethyl) (1b)

1. Cyclization
2. Purification

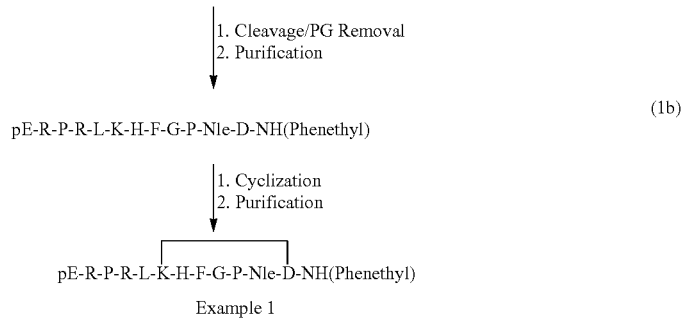

Example 1

Preparation of Intermediate 1a (Assembly of Linear Peptide)

Phenethylamine-BAL-PS resin (167 mg, 0.100 mmol) was subjected to solid phase peptide synthesis on the Prelude™ peptide synthesizer. Coupling was performed as follows:

| Coupling | AA | Number of couplings × Reaction time | Synthesis cycle |
|---|---|---|---|
| 1 | D(tBu) | 2 × 4 h | C |
| 2 | Nle | 1 × 3 h | C |
| 3 | P | 2 × 45 min | C |
| 4 | G | 2 × 90 min | C |
| 5 | F | 1 × 3 h | C |
| 6 | H(Trt) | 2 × 45 min | C |
| 7 | K(Boc) | 2 × 4 h | C |
| 8 | L | 4 × 1 h | C |
| 9 | R(Pbf) | 4 × 1 h | C |
| 10 | P | 2 × 90 min | C |
| 11 | R(Pbf) | 4 × 1 h | C |
| 12 | pE | 2 × 90 min | C |

Preparation of Intermediate 1b (Cleavage from the Resin with Concomitant Protecting Group Removal then Purification)

A mixture of 95% aq. TFA/EDT/TIS (95:2.5:2.5) (2 mL) was added to Intermediate 1a (0.1 mmol) and the suspension was shaken at rt for 2.5 h. The cleavage solution was filtered off, and fresh cleavage solution (2 mL) was added. The suspension was shaken at rt for 45 min then the cleavage solution was filtered off. Fresh solution (2 mL) was added and the suspension was shaken at rt for 45 min. The cleavage solution was filtered off and the resin was washed with 95% aq. TFA (1 mL). The combined cleavage solutions were poured onto a mixture of cold heptane/diethyl ether (1:1) (35 mL), giving a precipitate. The suspension was centrifuged and the supernatant poured off. The residue was washed with cold heptane/diethyl ether (1:1) (20 mL), the suspension was centrifuged and the supernatant was poured off. The solid was dried in high vacuum. The crude was purified by preparative HPLC and lyophilized from ACN/H$_2$O to afford Intermediate 1b as a white solid in two batches of different qualities: Batch A (35.9 mg (98% purity), 0.018 mmol) and batch B (52.9 mg (80% purity), 0.021 mmol).

Preparation of Example 1

(Cyclization and Purification)

Both batches from the previous step were treated separately following the same protocol:

Batch A: A solution of the peptide (35.9 mg (98% purity), 0.018 mmol) and HATU (10.0 mg, 0.026 mmol) in NMP (18 mL) and DIPEA (9.2 µL, 0.053 mmol) was stirred at rt for 2 h.

Batch B: A solution of the peptide (52.9 mg (80% purity), 0.021 mmol) and HATU (14.5 mg, 0.038 mmol) in NMP (26 mL) and DIPEA (13.0 µL, 0.076 mmol) was stirred at rt for 2 h.

Each of the batches was concentrated to dryness in vacuo. The product was isolated by preparative HPLC. Pure fractions of both purifications were combined and lyophilized from ACN/H$_2$O to give Example 1 as a white solid (52.0 mg, 0.025 mmol).

The pure product was analyzed by analytical HPLC (Analytical method A: $t_R$=4.16 min) and UPLC-MS (Analytical method C; measured: $[M+3]^{3+}$=511.2; calculated: $[M+3]^{3+}$=511.3).

Example 5 Synthesis pE-R-P-R-L-K-F-K-G-P-Nle-F (SEQ ID NO: 12) (Lactam K$^6$-C-Terminus)
Example 5 Below Discloses SEQ ID NO: 12

Cl-POL

Loading of resin

H-F-O-POL (5a)

SPPS pE-R(Pbf)-P-R(Pbf)-L-K(ivDde)-F-K(Boc)-G-P-Nle-F-O-POL (5b)

1. Removal of ivDde
2. Cleavage with HFIP

-continued pE-R(Pbf)-P-R(Pbf)-L-K-F-K(Boc)-G-P-Nle-F-OH    (5c)

↓ Cyclization pE-R(Pbf)-P-R(Pbf)-L-K-F-K(Boc)-G-P-Nle-F    (5d)
|_____|

1. PG Removal
2. Purification pE-R-P-R-L-K-F-K-G-P-Nle-F
|_____|

Example 5

Preparation of Intermediate 5a (Loading of 2-chlorotrityl chloride resin with Fmoc-F-OH, Fmoc Removal and Determination of the Loading of the Resin)

2-Chlorotrityl chloride resin (10.0 g, 16.0 mmol) was reacted with a solution of Fmoc-F-OH (6.24 g, 32.0 mmol) in DCM (100 mL) and DIPEA (11.2 mL, 64.0 mmol) in analogy to the general procedure described above to give Intermediate 5a (12.8 g, loading=0.79 mmol/g).

Preparation of Intermediate 5b (Assembly of Linear Peptide)

Intermediate 5a (0.100 mmol) was subjected to solid phase peptide synthesis on the Prelude™ peptide synthesizer. Coupling was performed as follows:

| Coupling | AA | Number of couplings × Reaction time | Synthesis cycle |
|---|---|---|---|
| 2 | Nle | 2 × 90 min | B |
| 3 | P | 2 × 30 min | B |
| 4 | G | 2 × 90 min | B |
| 5 | K(ivDde) | 2 × 30 min | B |
| 6 | F | 2 × 30 min | B |
| 7 | K(Boc) | 4 × 1 h | B |
| 8 | L | 2 × 30 min | B |
| 9 | R(Pbf) | 4 × 1 h | B |
| 10 | P | 2 × 90 min | B |
| 11 | R(Pbf) | 4 × 1 h | B |
| 12 | pE | 2 × 90 min | B |

Preparation of Intermediate 5c (Removal of ivDde and Cleavage from the Resin)

Intermediate 5b (0.100 mmol) was treated six times for 10 min with a solution of hydrazine monohydrate (0.081 mL, 1.67 mmol) in DMA (4 mL). Then the resin was treated three times for 20 min with a solution of hydrazine monohydrate (0.081 mL, 1.67 mmol) in THF (4 mL). The resin was washed with DCM (3×). HFIP/DCM (30:70) (5 mL) was added to the resin (0.100 mmol) and the suspension was stirred at rt for 1.5 h. The cleavage solution was filtered off and fresh HFIP/DCM (30:70) (5 mL) was added. The suspension was stirred at rt for 30 min. The cleavage solution was filtered off. The resin was washed with DCM (2×5 mL). The combined cleavage and washing solutions were concentrated to dryness in vacuo. The residue was lyophilized from tBuOH/H$_2$O (1:1) to give Intermediate 5c (187 mg, 0.090 mmol).

Preparation of Example 5

(Cyclization and Removal of Protecting Groups)

A solution of Intermediate 5c (187 mg, 0.090 mmol), HATU (44.6 mg, 0.117 mmol) and HOAt (16.0 mg, 0.117 mmol) in DMF (35 mL) was treated with 2,6-lutidine (0.210 mL, 1.80 mmol) and the reaction was stirred at rt for 2 h. The reaction mixture was concentrated to dryness in vacuo. The residue was dissolved in 95% aq. TFA/EDT/TIS (95:2.5:2.5) (5 mL) and the solution was stirred at rt for 2.5 h. The cleavage solution was poured onto cold heptane/diethyl ether (1:1) (30 mL), giving a precipitate. The suspension was centrifuged and the supernatant poured off. The residue was washed with cold heptane/diethyl ether (1:1) (10 mL), the suspension was centrifuged and the supernatant was poured off. The washing step was repeated once. The residue was dried in high vacuum. The product was isolated by preparative HPLC and lyophilized from ACN/H$_2$O to afford Example 5 as a white solid (41.4 mg, 0.023 mmol).

The pure product was analyzed by analytical HPLC (Analytical method A: $t_R$=3.70 min) and UPLC-MS (Analytical method C; measured: $[M+3]^{3+}$=484.5; calculated: $[M+3]^{3+}$=484.6).

Example 7 Synthesis Q-R-P-R-L-C-F-K-G-P-Nle-C-F-G-G (SEQ ID NO: 14) (Lactam N-Terminus-C-Terminus) Example 7 Below Discloses SEQ ID NO: 14

Cl-POL    (7a)

↓ Loading of resin

H-G-O-POL

1. SPPS
2. Fmoc removal

↓

H-Q(Trt)-R(Pbf)-P-R(Pbf)-L-C(Trt)-F-K(Boc)-G-P-Nle-C(Trt)-F-G-G-O-POL  (7b)

↓ Cleavage with HFIP

H-Q(Trt)-R(Pbf)-P-R(Pbf)-L-C(Trt)-F-K(Boc)-G-P-Nle-C(Trt)-F-G-G-OH  (7c)

↓ Cyclization

⌐──────────────────────────────────────────────────────────────┐  (7d)
Q(Trt)-R(Pbf)-P-R(Pbf)-L-C(Trt)-F-K(Boc)-G-P-Nle-C(Trt)-F-G-G

↓ 1. PG Removal
  2. Purification

⌐─────────────────────────────┐  (7e)
Q-R-P-R-L-C-F-K-G-P-Nle-C-F-G-G

↓ 1. Cyclization
  2. Purification

⌐──────────┐   ⌐──────────┐
Q-R-P-R-L-C-F-K-G-P-Nle-C-F-G-G

Example 7

Preparation of Intermediate 7a (Loading of 2-chlorotrityl chloride Resin with with Fmoc-Gly-OH, Fmoc Removal and Determination of the Loading of the Resin)

2-Chlorotrityl chloride resin (2.00 g, 3.20 mmol) was reacted with a solution of Fmoc-Gly-OH (0.476 g, 1.60 mmol) in DCM (20 mL) and DIPEA (2.24 mL, 12.8 mmol) in analogy to the general procedure described above to give Intermediate 7a (2.22 g; loading=0.68 mmol/g).

Preparation of Intermediate 7b (Assembly of Linear Peptide and Fmoc Removal)

Intermediate 7a (147 mg, 0.100 mmol) was subjected to solid phase peptide synthesis on the Prelude™ peptide synthesizer. Coupling was performed as follows:

| Coupling | AA | Number of couplings × Reaction time | Synthesis cycle |
|---|---|---|---|
| 1 | G | 2 × 30 min | B |
| 2 | F | 2 × 30 min | B |
| 3 | C(Trt) | 2 × 30 min | B |
| 4 | Nle | 2 × 90 min | B |
| 5 | P | 2 × 30 min | B |
| 6 | G | 2 × 90 min | B |
| 7 | K(Boc) | 2 × 30 min | B |
| 8 | F | 2 × 30 min | B |
| 9 | C(Trt) | 2 × 30 min | B |
| 10 | L | 2 × 30 min | B |
| 11 | R(Pbf) | 4 × 1 h | B |
| 12 | P | 2 × 90 min | B |
| 13 | R(Pbf) | 4 × 1 h | B |
| 14 | Q(Trt) | 2 × 90 min | B |

After assembly of the peptide Fmoc was removed by repetitive treatment with piperidine/DMA (1:4). The resin was washed with DMA to afford Intermediate 7b (0.100 mmol).

Preparation of Intermediate 7c (HFIP Cleavage from the Resin)

HFIP/DCM (30:70) (3 mL) was added to Intermediate 7b (0.100 mmol) and the suspension was shaken at rt for 1.5 h. The cleavage solution was filtered off and fresh HFIP/DCM (30:70) (3 mL) was added. The suspension was shaken at rt for 30 min. The cleavage solution was filtered off. The resin was washed with DCM (2×3 mL). The combined cleavage and washing solutions were concentrated to dryness in vacuo. The residue was lyophilized from tBuOH/H$_2$O (1:1) to give Intermediate 7c (203 mg, 0.067 mmol).

Preparation of Intermediate 7d (Backbone Cyclization)

A solution of Intermediate 7c (203 mg, 0.067 mmol), HATU (33.3 mg, 0.088 mmol) and HOAt (11.9 mg, 0.088 mmol) in DMF (40 mL) was treated with 2,6-lutidine (0.157 ml, 1.35 mmol) and the reaction was stirred at rt for 2 h. The reaction mixture was concentrated to dryness in vacuo to afford Intermediate 7d (0.067 mmol).

Preparation of Intermediate 7e (Removal of Protecting Groups then Purification)

A mixture of 95% aq. TFA/EDT/TIS (95:2.5:2.5) (3 mL) was added to Intermediate 7d (0.067 mmol) and the suspension was shaken at rt for 2.5 h. The solution was poured onto a mixture of cold heptane/diethyl ether (1:1) (30 mL), giving a precipitate. The suspension was centrifuged and the supernatant poured off. The residue was washed with cold heptane/diethyl ether (1:1) (10 mL), the suspension was centrifuged and the supernatant was poured off. The washing step was repeated once. The solid was dried in high vacuum. The crude was purified by preparative HPLC and lyophilized from ACN/H$_2$O to afford Intermediate 7e as a white solid (33.6 mg, 0.017 mmol).

Preparation of Example 7

(Cyclization and Purification)

Intermediate 7e (33.6 mg, 0.017 mmol) was dissolved in H$_2$O/DMSO (9:1) (30 mL). The reaction mixture was stirred at rt for 40 h then concentrated to dryness in vacuo. The crude was purified by preparative HPLC and lyophilized from ACN/H$_2$O to afford Example 7 as a white solid (21.0 mg; 0.010 mmol).

The pure product was analyzed by analytical HPLC (Analytical method A: $t_R$=3.85 min) and UPLC-MS (Analytical method C; measured: $[M+3]^{3+}$=553.6; calculated: $[M+3]^{3+}$=553.6).

Example 8 Synthesis of pE-R-P-R-L-C-H-K-G-P-Nle-C-F-OH (SEQ ID NO: 15) (Disulfide $C^6$-$C^{12}$)
Example 8 below Discloses SEQ ID NO: 15

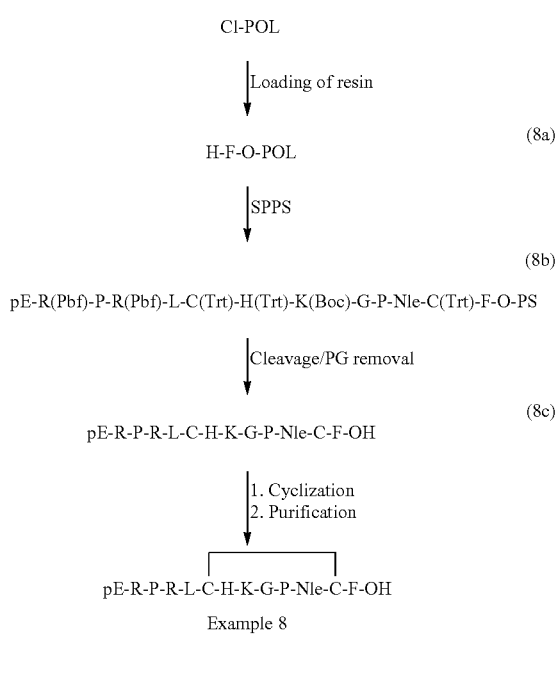

Example 8

Preparation of Intermediate 8a (Loading of 2-chlorotrityl chloride Resin with Fmoc-F-OH, Fmoc Removal and Determination of the Loading of the Resin)

2-Chlorotrityl chloride resin (40.0 g, 64.0 mmol) was washed with DCM (3×). A solution of Fmoc-F-OH (24.8 g, 64.0 mmol) in DCM (400 mL) and DIPEA (44.7 mL, 256 mmol) was added and the suspension was shaken for 22 h at rt. The resin was washed thoroughly with DCM/MeOH/DIPEA (17:2:1) (3×), DCM (3×), DMA (3×), DCM (3×).

The resin was then treated four times for 10 min with a mixture of piperidine/DMA (1:4) (400 mL) followed by washing with DMA (2×180 ml). The piperidine/DMA solutions and DMA washing solutions were collected for determination of the loading of the resin. 1 mL of the combined solutions was diluted to 500 mL with MeOH and the UV absorption at 299.8 nm was measured to be A=0.368. This corresponds to an Fmoc amount of 46.2 mmol.

The resin was washed thoroughly with DCM (3×), DMA (3×), DCM (3×) and dried in vacuo to give Intermediate 8a (50.7 g; loading=0.91 mmol/g).

Preparation of Intermediate 8b (Assembly of Linear Peptide)

Intermediate 8a (2.64 g, 2.40 mmol) was subjected to solid phase peptide synthesis on the Prelude™ peptide synthesizer. Coupling was performed as follows:

| Coupling | AA | Number of couplings × Reaction time | Synthesis cycle |
| --- | --- | --- | --- |
| 1 | C(Trt) | 2 × 30 min | D |
| 2 | Nle | 2 × 15 min | A |
| 3 | P | 2 × 15 min | A |
| 4 | G | 2 × 30 min | A |
| 5 | K(Boc) | 2 × 15 min | A |
| 6 | H(Trt) | 2 × 15 min | A |
| 7 | C(Trt) | 2 × 60 min | D |
| 8 | L | 2 × 15 min | A |
| 9 | R(Pbf) | 4 × 1 h | A |
| 10 | P | 2 × 15 min | A |
| 11 | R(Pbf) | 4 × 1 h | A |
| 12 | pE | 2 × 15 min | A |

Preparation of Intermediate 8c (Cleavage from the Resin with Concomitant Protecting Group Removal)

Intermediate 8b (2.40 mmol) was carefully washed with DCM (4×). A mixture of 95% aq. TFA/EDT/TIS (95:2.5:2.5) (50 mL) was added and the suspension was shaken at rt for 1 h. The cleavage solution was filtered off, and fresh cleavage solution (35 mL) was added. The suspension was shaken at rt for 1 h then the cleavage solution was filtered off. Fresh solution (35 mL) was added and the suspension was shaken at rt for 1 h. The cleavage solution was filtered off. The combined cleavage solutions were poured slowly onto a stirred mixture of cold heptane/diethyl ether (1:1) (500 mL), giving a precipitate. The suspension was stirred at rt for 2 h and then the precipitate was allowed to settle down. The supernatant was sucked off with a frit. The residue was washed with cold heptane/diethyl ether (1:1) (2×100 mL), the supernatant was sucked off with a frit. The solid was dried in high vacuum to afford Intermediate 8c as an off-white solid (3.75 g, 1.88 mmol).

Preparation of Example 8

(Cyclization and Purification)

Intermediate 8c (3.75 g, 1.88 mmol) was dissolved in H$_2$O (375 mL). A solution of 50 mM I$_2$ in AcOH (45.1 mL, 2.26 mmol) was added in one portion to the stirred solution and the solution was stirred for 10 min at rt. 0.5 M Ascorbic acid in H$_2$O (5.64 mL, 2.82 mmol) was added to quench the excess of I$_2$. The solution was concentrated to near dryness. The reaction was performed in two portions: 0.188 mmol scale and 1.69 mmol scale. The crudes were combined for purification. The crude was purified by preparative HPLC and lyophilized from ACN/H₂O to afford Example 8 as a white solid (1.53 g, 0.767 mmol).

The pure product was analyzed by analytical HPLC (Analytical method C: $t_R$=3.43 min) and UPLC-MS (Analytical method B; measured: $[M+3]^{3+}$=512.4; calculated: $[M+3]^{3+}$=512.6).

Alternatively, The crude polypeptide of Example 8 was dissolved in water (500 mL of water/mmol of polypeptide) and was converted into the acetate salt with the aid of an ion exchange resin (i.e. Amberlite IRA-67 (Acetate-Form)(200 g/mmol of polypeptide) and purified by preparative HPLC (C8 modified reversed phase silica gel from Daisogel, gradient: ACN/H₂O: 3% ACN and 97% [mixture 0.3% Acetic acid/water] up to 12% ACN and 88% [mixture 0.3% Acetic acid/water]) and lyophilized to afford an acetate salt of Example 8 as a white solid (60-100% yield).

The salt stoichiometry was evaluated based on the analysis of the acetic acid content (ion chromatography) and water content and was determined to range between 1:3 and 1:4 (polypeptide: acetate).

Example 26 Synthesis of pE-R-P-R-L-C-H-K-G-P-Nle-C-K(Lauroyl)-OH (SEQ ID NO: 33) (disulfide $C^6$-$C^{12}$) Example 26 Below Discloses SEQ ID NO: 33

Preparation of Intermediate 26a (Loading of 2-chlorotrityl chloride Resin with with Fmoc-K(ivDde)-OH, Fmoc Removal and Determination of the Loading of the Resin)

2-Chlorotrityl chloride resin (1.00 g, 1.60 mmol) was reacted with a solution of Fmoc-K(ivDde)-OH (1.84 g, 3.20 mmol) in DCM (10 mL) and DIPEA (1.12 mL, 6.40 mmol) in analogy to the general procedure described above to give Intermediate 26a (1.39 g; loading=0.75 mmol/g).

Preparation of Intermediate 26b (Assembly of Linear Peptide)

Intermediate 26a (134 mg, 0.100 mmol) was subjected to solid phase peptide synthesis on the Prelude™ peptide synthesizer. Coupling was performed as follows:

| Coupling | AA | Number of couplings × Reaction time | Synthesis cycle |
| --- | --- | --- | --- |
| 1 | C(Trt) | 2 × 30 min | B |
| 2 | Nle | 2 × 30 min | B |
| 3 | P | 2 × 30 min | B |
| 4 | G | 2 × 90 min | B |
| 5 | K(Boc) | 2 × 30 min | B |
| 6 | H(Trt) | 2 × 30 min | B |
| 7 | C(Trt) | 2 × 30 min | B |

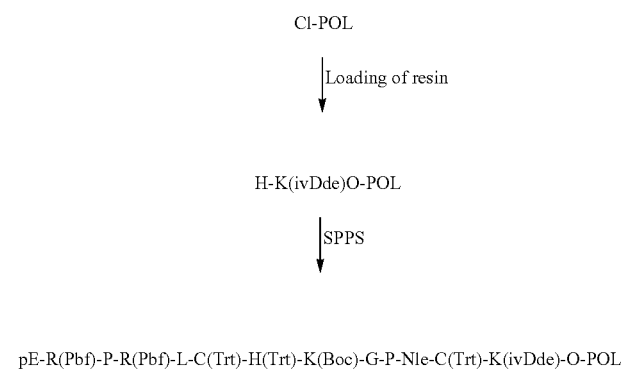

(26a)

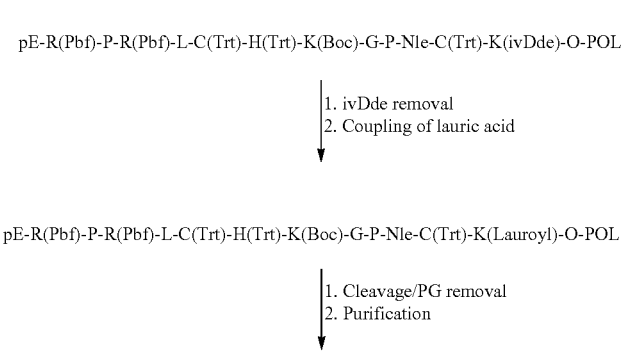

(26b)

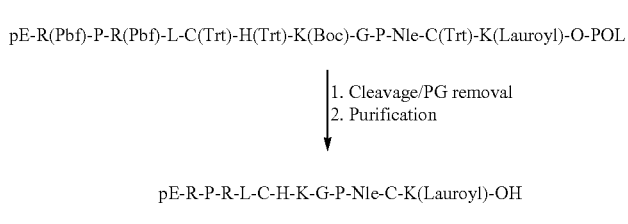

(26c)

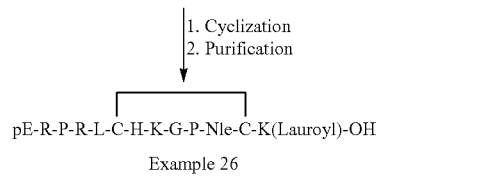

(26d)

Example 26

| Coupling | AA | Number of couplings × Reaction time | Synthesis cycle |
|---|---|---|---|
| 8 | L | 2 × 30 min | B |
| 9 | R(Pbf) | 4 × 1 h | B |
| 10 | P | 2 × 90 min | B |
| 11 | R(Pbf) | 4 × 1 h | B |
| 12 | pE | 2 × 90 min | B |

Preparation of Intermediate 26c (Removal of ivDde and Coupling of Lauric Acid)

Intermediate 26b (0.100 mmol) was washed with THF (3×). A solution of hydrazine monohydrate (0.245 ml, 5.00 mmol) in THF (12 mL) was added and the suspension was shaken at rt for 1 h. The solution was filtered off. This step was done twice more. The resin was washed with DMA (3×), DCM (3×), DMA (2×), DCM (5×) and DMA (3×). Lauric acid (100 mg, 0.500 mmol) and HCTU (207 mg, 0.500 mmol) were dissolved in NMP (3 mL) and DIPEA (0.087 ml, 0.500 mmol). After 5 min activation the solution was added to the resin and the suspension was shaken at rt for 16 h. The reaction mixture was filtered off and the resin washed with DMA (3×), DCM (3×), DMA (3×), DCM (5×) to afford Intermediate 26c.

Preparation of Intermediate 26d (Cleavage from the Resin with Concomitant Protecting Group Removal then Purification)

A mixture of 95% aq. TFA/EDT/TIS (95:2.5:2.5) (3 mL) was added to Intermediate 26c (0.100 mmol) and the suspension was shaken at rt for 2 h. The cleavage solution was filtered off, and fresh cleavage solution (3 mL) was added. The suspension was shaken at rt for 1 h then the cleavage solution was filtered off. Fresh solution (3 mL) was added and the suspension was shaken at rt for 1 h. The cleavage solution was filtered off. The combined cleavage solutions were poured onto a mixture of cold heptane/diethyl ether (1:1) (35 mL), giving a precipitate. The suspension was centrifuged and the supernatant poured off. The residue was washed with cold heptane/diethyl ether (1:1) (10 mL), the suspension was centrifuged and the supernatant was poured off. The solid was dried in high vacuum.

The crude was purified by preparative HPLC and lyophilized from ACN/H$_2$O to afford Intermediate 26d as a white solid (74.1 mg, 0.034 mmol).

Preparation of Example 26

(Cyclization and Purification)

Intermediate 2d (74.1 mg, 0.034 mmol) was dissolved in H$_2$O/DMSO (9:1) (74 mL). The reaction mixture was stirred at rt for 40 h then concentrated to dryness in vacuo. The crude was purified by preparative HPLC and lyophilized from ACN/H$_2$O to afford Example 26 as a white solid (60.0 mg; 0.028 mmol).

The pure product was analyzed by analytical HPLC (Analytical method A: $t_R$=5.11 min) and UPLC-MS (Analytical method B; measured: $[M+3]^{3+}$=567.0; calculated: $[M+3]^{3+}$=567.0).

Example 28 Synthesis pE-R-P-C-L-C-C-K-G-P-Nle-C-F-OH (SEQ ID NO: 35) (Disulfides $C^4$-$C^7$ and $C^6$-$C^{12}$) Example 28 Below Discloses SEQ ID NO: 35

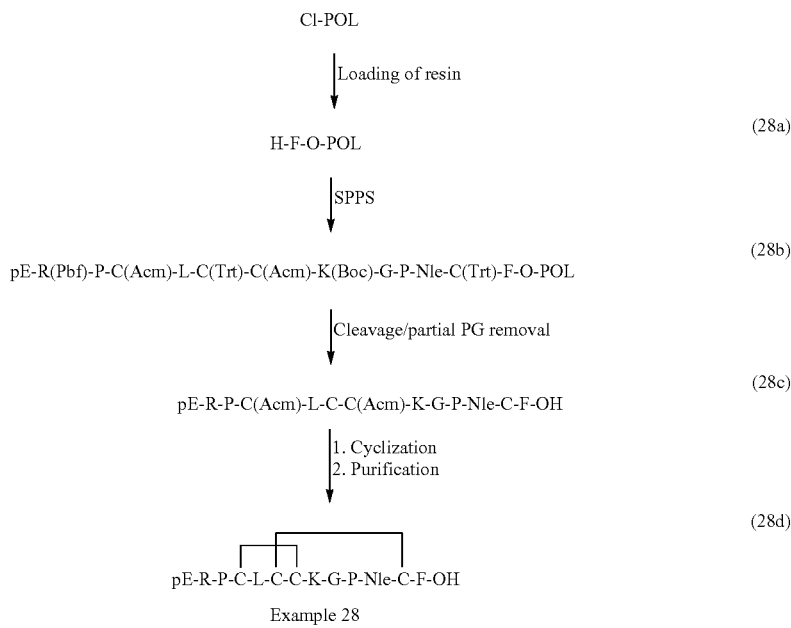

Preparation of Intermediate 28a (Loading of 2-chlorotrityl chloride Resin with Fmoc-F-OH, Fmoc Removal and Determination of the Loading of the Resin)

2-Chlorotrityl chloride resin (10.0 g, 16.0 mmol) was reacted with a solution of Fmoc-F-OH (6.20 g, 16.0 mmol) in DCM (100 mL) and DIPEA (11.2 mL, 64.0 mmol) in analogy to the general procedure described above to give Intermediate 28a (11.6 g, loading=0.87 mmol/g).

Preparation of Intermediate 28b (Assembly of Linear Peptide)

Intermediate 28a (115 mg, 0.100 mmol) was subjected to solid phase peptide synthesis on the Prelude™ peptide synthesizer. Coupling was performed as follows:

| Coupling | AA | Number of couplings × Reaction time | Synthesis cycle |
| --- | --- | --- | --- |
| 1 | C(Trt) | 2 × 15 min | B |
| 2 | Nle | 2 × 15 min | B |
| 3 | P | 2 × 15 min | B |
| 4 | G | 2 × 90 min | B |
| 5 | K(Boc) | 2 × 15 min | B |
| 6 | C(Acm) | 2 × 15 min | B |
| 7 | C(Trt) | 2 × 15 min | B |
| 8 | L | 2 × 15 min | B |
| 9 | C(Acm) | 2 × 15 min | B |
| 10 | P | 2 × 15 min | B |
| 11 | R(Pbf) | 4 × 1 h | B |
| 12 | pE | 2 × 15 min | B |

Preparation of Intermediate 28c (Cleavage from the Resin with Concomitant Partial Protecting Group Removal)

Intermediate 28b (0.100 mmol)) was carefully washed with DCM (4×). A mixture of 95% aq. TFA/EDT (4:1) (0.750 mL) was added and the suspension was shaken at rt for 1 h. A mixture of TFA/$H_2O$ (95:5) (2.18 mL) and TIS (75 μL) was added to the suspension and shaking at rt was continued for 1 h. The cleavage solution was filtered off and a mixture of 95% aq. TFA/EDT/TIS (95:2.5:2.5) (3 mL) was added to the resin. The suspension was shaken at rt for 1 h the cleavage solution was filtered off. Fresh solution was added (3 mL) and the suspension was shaken at rt for 1 h. The cleavage solution was filtered off. The combined cleavage solutions were poured onto cold heptane/diethyl ether (1:1) (35 mL), giving a precipitate. The suspension was centrifuged and the supernatant poured off. The residue was washed with cold heptane/diethyl ether (1:1) (10 mL), the suspension was centrifuged and the supernatant was poured off. The washing step was repeated once. The residue was dried in high vacuum. The crude product was purified by preparative HPLC and lyophilized from ACN/$H_2O$ to afford Intermediate 28c as a white solid (51.1 mg, 0.028 mmol).

Preparation of Example 28

(One-Pot Formation of Two Disulfides)

Intermediate 28c (51.1 mg, 0.028 mmol) was dissolved in AcOH (48 mL) and $H_2O$ (12 mL).

A 50 mM solution of $I_2$ in AcOH (1.12 mL, 56 μmol) was added and the yellow solution was stirred at rt. Further 50 mM $I_2$ in AcOH (5.61 mL, 0.281 mmol) was added portion wise over 4 h. After 21 h, the reaction mixture was concentrated to 2 mL in vacuo and 1 M ascorbic acid in $H_2O$ (6 mL) was added to quench the excess of $I_2$. The product was isolated by preparative HPLC and lyophilized from ACN/$H_2O$ to afford Example 28 as a white solid (19.3 mg, 0.012 mmol).

The pure product was analyzed by analytical HPLC (Analytical method A: $t_R$=4.16 min) and UPLC-MS (Analytical method C; measured: $[M+2]^{2+}$=723.7; calculated: $[M+2]^{2+}$=723.8).

Example 62 Synthesis of pE-R-P-R-L-C-H-K-G-P-Nle-C—F—NH2 (SEQ ID NO: 69) (Disulfide $C^6$-$C^{12}$) Example 62 Below Discloses SEQ ID NO: 69

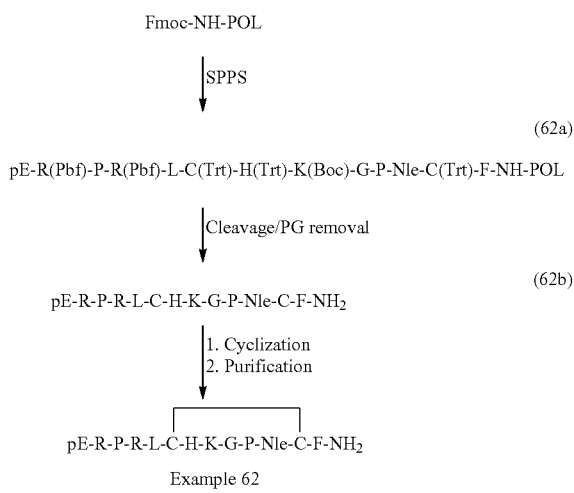

Preparation of Intermediate 62a (Assembly of Linear Peptide)

Fmoc protected Rink-Amide-AM-PS-resin (217 mg, 0.100 mmol) was subjected to solid phase peptide synthesis on the Prelude™ peptide synthesizer. Coupling was performed as follows:

| Coupling | AA | Number of couplings × Reaction time | Synthesis cycle |
| --- | --- | --- | --- |
| 1 | F | 2 × 15 min | A |
| 2 | C(Trt) | 2 × 30 min | D |
| 3 | Nle | 2 × 15 min | A |
| 4 | P | 2 × 15 min | A |
| 5 | G | 2 × 30 min | A |
| 6 | K(Boc) | 2 × 15 min | A |
| 7 | H(Trt) | 2 × 15 min | A |
| 8 | C(Trt) | 2 × 1 h | D |
| 9 | L | 2 × 15 min | A |
| 10 | R(Pbf) | 4 × 1 h | A |
| 11 | P | 2 × 15 min | A |
| 12 | R(Pbf) | 4 × 1 h | A |
| 13 | pE | 2 × 15 min | A |

Preparation of Intermediate 62b (Cleavage from the Resin with Concomitant Protecting Group Removal)

A mixture of 95% aq. TFA/EDT/TIS (95:2.5:2.5) (3 mL) was added to Intermediate 62a (0.1 mmol) and the suspension was shaken at rt for 1.5 h. The cleavage solution was filtered off, and fresh cleavage solution (2 mL) was added. The suspension was shaken at rt for 45 min then the cleavage solution was filtered off. Fresh solution (2 mL) was added and the suspension was shaken at rt for 45 min. The combined cleavage solutions were poured onto a mixture of cold heptane/diethyl ether (1:1) (35 mL), giving a precipitate. The suspension was centrifuged and the supernatant poured off. The residue was washed with cold heptane/diethyl ether (1:1) (10 mL), the suspension was centrifuged and the supernatant was poured off. The solid was dried in high vacuum. The crude product Intermediate 62b was used in the next step without purification.

Preparation of Example 62

(Cyclization and Purification)

Intermediate 62b (0.100 mmol) was dissolved in $H_2O$ (20 mL). A solution of 50 mM $I_2$ in AcOH (2.4 mL, 0.120 mmol) was added in one portion to the stirred solution and the solution was stirred for 30 min at rt. 0.5 M Ascorbic acid in $H_2O$ (0.30 mL, 0.300 mmol) was added to quench the excess of $I_2$. The solution was concentrated to near dryness. The crude was purified by preparative HPLC and lyophilized from ACN/$H_2O$ to afford Example 62 as a white solid (50.5 mg, 0.025 mmol).

The pure product was analyzed by analytical HPLC (Analytical method C: $t_R$=3.22 min) and UPLC-MS (Analytical method C; measured: $[M+3]^{3+}$=512.3; calculated: $[M+3]^{3+}$=512.3).

The other examples were synthesized in analogy:
Examples 2 to 4 were synthesized in analogy to Example 1.
Example 6 was synthesized in analogy to Example 5.
Example 9 to 25, and 27 were synthesized in analogy to Example 26.
Example 29 was synthesized in analogy to Example 28.
Examples 30 to 61 were synthesized in analogy to Example 8.
Example 63 was synthesized in analogy to Example 62.

Example 64: pE-R-P-R-L-C-H-K-G-P-Nle-C-F-OH (SEQ ID NO: 71) with a —S—$CH_2$—C(O)$CH_2$—S— Linkage Between the Cysteines at Position 6 and 12 [$C^6$-$C^{12}$]

Analytical Method
Method D (HRMS);
Eluent A: water+0.05% Formic acid+3.75 mM ammonium acetate, Eluent B: Acetonitrile+0.04% Formic acid.
Gradient: from 2 to 98% B in 4.4 min–Flow 1.0 ml/min.
Column: Acquity CSH 1.7 μm 2.1*50 mm 50° C.

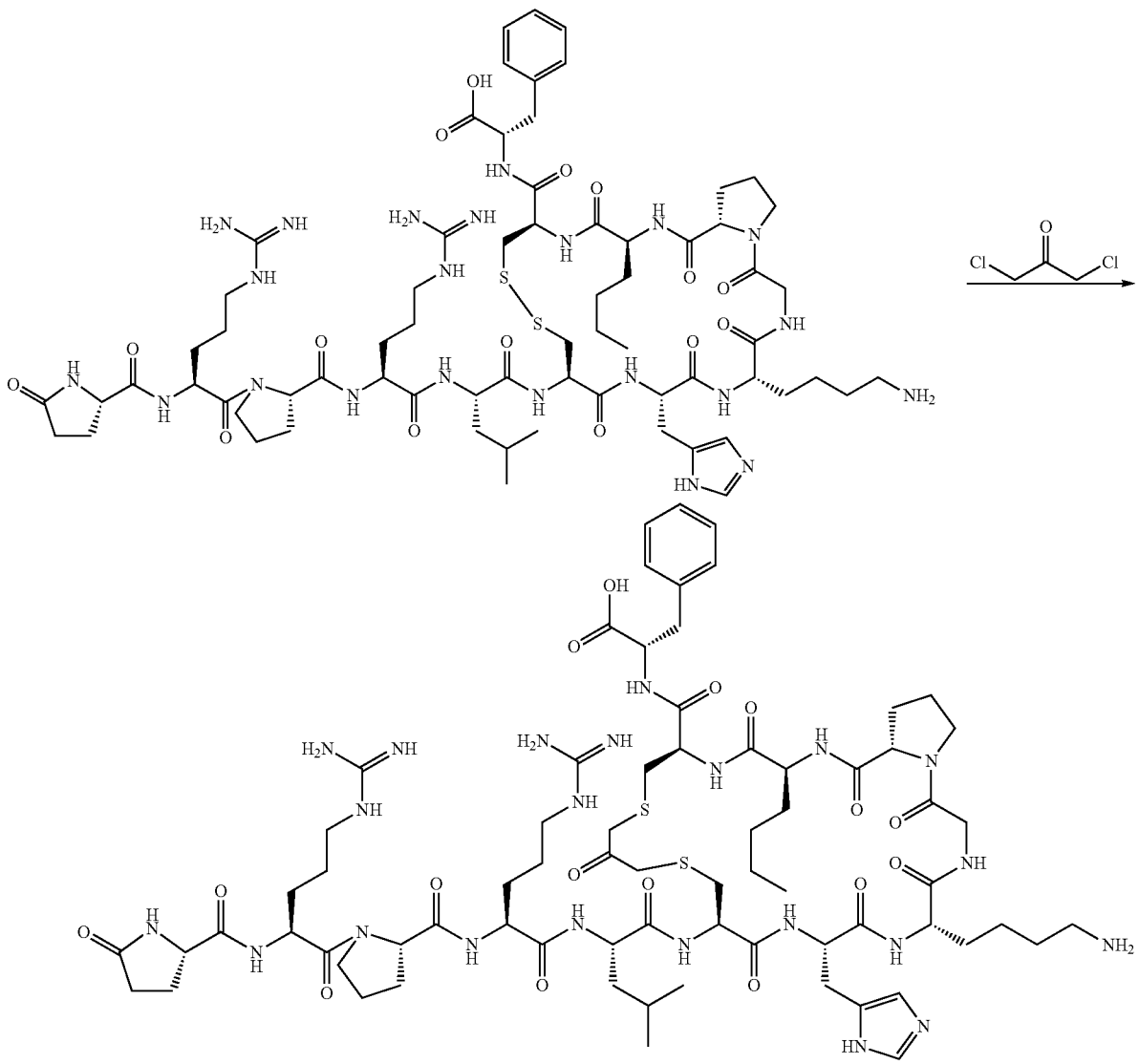

Example 8 ((S)-2-((3S,6R,11R,14S,17S,25aS)-14-((1H-imidazol-5-yl)methyl)-17-(4-aminobutyl)-3-butyl-11-((S)-2-((S)-5-guanidino-2-((S)-1-((S)-5-guanidino-2-((S)-5-oxopyrrolidine-2-carboxamido)pentanoyl)pyrrolidine-2-carboxamido)pentanamido)-4-methylpentanamido)-1,4,12,15,18,21-hexaoxodocosahydro-1H-pyrrolo[2,1-j][1,2,5,8,11,14,17,20]dithiahexaazacyclotricosine-6-carboxamido)-3-phenylpropanoic acid) (12 mg, 6.76 µmol) was dissolved in 50 mM sodium phosphate buffer pH6.5 (1.5 ml), into which was added TCEP HCl ((tris(2-carboxyethyl)phosphine) (2.91 mg, 10.13 µmol) at RT. This reaction mixture was stirred for 1 h at RT. Into above solution was added 1,3-dichloropropan-2-one (4.29 mg, 0.034 mmol) at RT, which was stirred for 30 min at RT. RP-HPLC eluting 15-60% MeCN/water with 0.1% TFA gave Example 64 ((S)-2-((3S,6R,14R,17S,20S,28aS)-17-((1H-imidazol-5-yl)methyl)-20-(4-aminobutyl)-3-butyl-14-((S)-2-((S)-5-guanidino-2-((S)-1-((S)-5-guanidino-2-((S)-5-oxopyrrolidine-2-carboxamido)pentanoyl)pyrrolidine-2-carboxamido)pentanamido)-4-methylpentanamido)-1,4,10,15,18,21,24-heptaoxohexacosahydropyrrolo[2,1 i][1,23,4,7,10,13,16,19]dithiahexaazacyclohexacosine-6-carboxamido)-3-phenylpropanoic acid) (6 mg, 2.93 µmol, 43.4% yield). HRMS (method D) [M+1]; 1590.7911 (observed), 1590.7912 (expected). Retention time; 3.08 min.

Example 65 pE-R-P-R-L-C-H-K-G-P-Nle-C-F-OH (SEQ ID NO: 72) with a Monosulfide Linkage Between the 2 Cysteines at Position 6 and 12 [$C^6$-$C^{12}$]

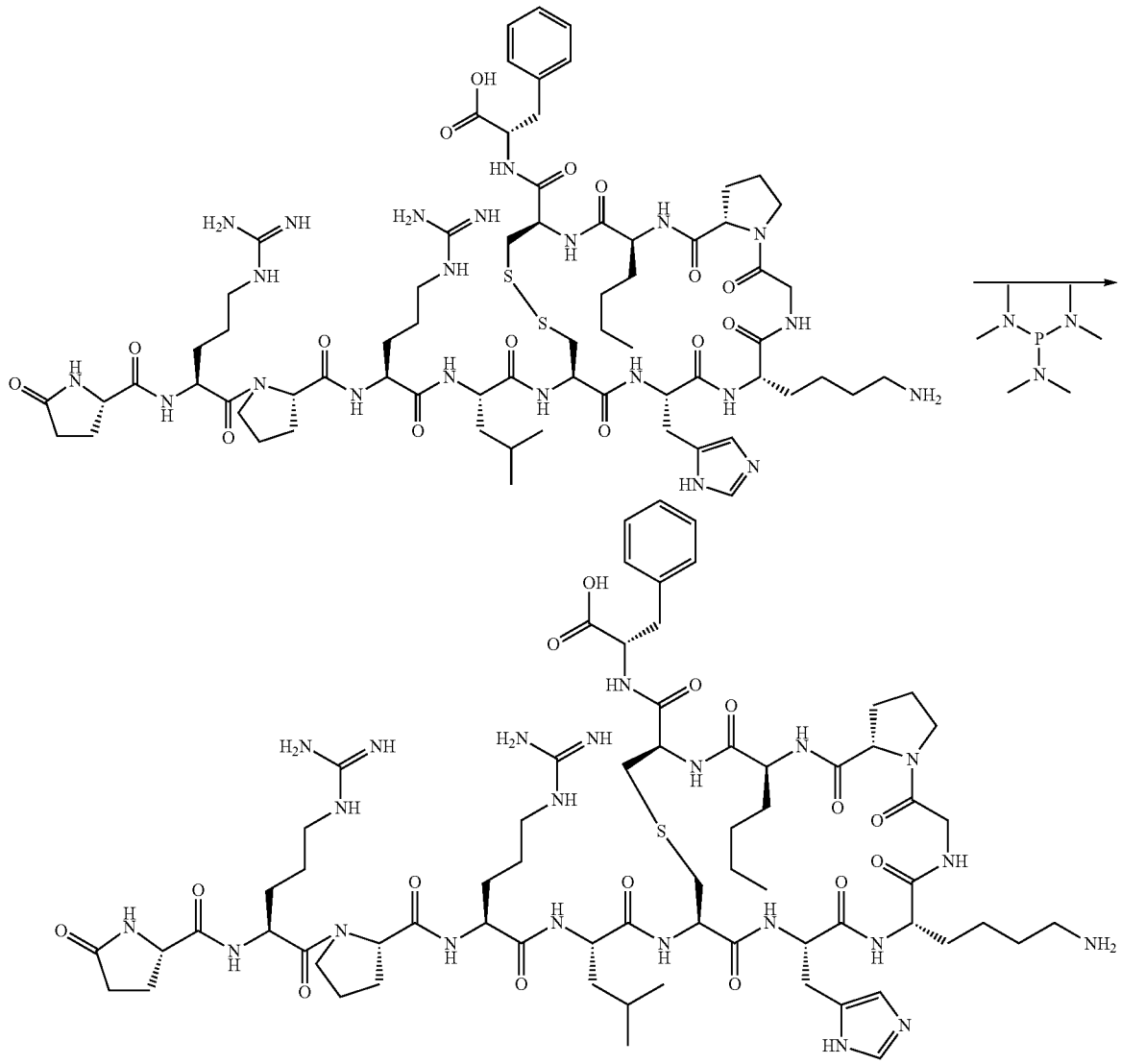

The mixture of Example 8 (S)-2-((3S,6R,11R,14S,17S,25aS)-14-((1H-imidazol-5-yl)methyl)-17-(4-aminobutyl)-3-butyl-11-((S)-2-((S)-5-guanidino-2-((S)-1-((S)-5-guanidino-2-((S)-5-oxopyrrolidine-2-carboxamido) pentanoyl) pyrrolidine-2-carboxamido)pentanamido)-4-methylpentanamido)-1,4,12,15,18,21-hexaoxodocosahydro-1H-pyrrolo[2,1-j][1,2,5,8,11,14,17,20]dithiahexaazacyclotricosine-6-carboxamido)-3-phenylpropanoic acid TFA salts (30 mg, 0.15 mmol) and N,N,N',N',N'',N''-hexamethylphosphinetriamine (12.3 mg, 0.75 mmol) in PBS pH 9.2 puffer (1 mL) was stirred at RT for 3 days. The reaction mixture was purified by preparative HPLC (Sunfire C18, 0.1% TFA in water/MeCN) twice, and the product fraction was lyophilized to a white powder (Example 65: 4 mg, 13.4%). [M+2H]2+ (calc.)=752.88, [M+2H]2+ (measured)=752.40, [M+3H]3+ (calc.)=502.26, [M+3H]3+ (measured)=501.94. HPLC (analytical method C), Tr min=6.93.

Example 66 pE-R-P-R-L-C-H-K-G-P-Nle-C-F-OH (SEQ ID NO: 73) with a —S—CH$_2$—C(=Z)—CH$_2$—S— Linkage Between the 2 Cysteines at Position 6 and 12 [C$^6$-C$^{12}$] and Z is

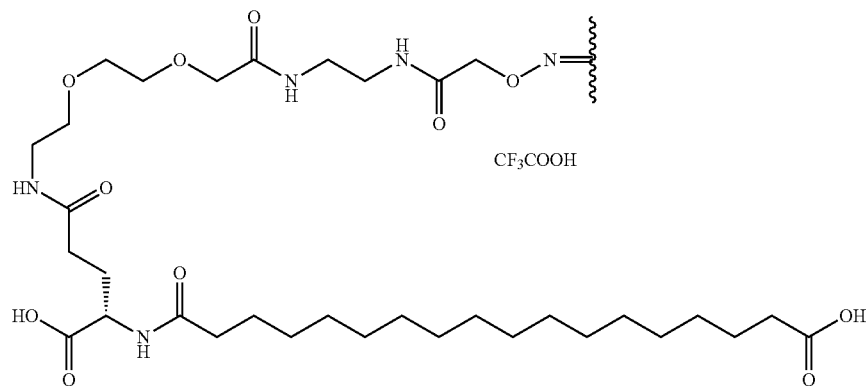 [SMILES: *=NOCC(=O)NCCNC(=O)COCCOCCNC(=O)CC[C@H](NC(=O)CCCCCCCCCCCCCCCCC(=O)O)C(=O)O ; "CF3COOH"]

Analytical Method
Method D (HRMS);
Eluent A: water+0.05% Formic acid+3.75 mM ammonium acetate, Eluent B: Acetonitrile+0.04% Formic acid.
Gradient: from 2 to 98% B in 4.4 min–Flow 1.0 ml/min.
Column: Acquity CSH 1.7 μm 2.1*50 mm 50° C.

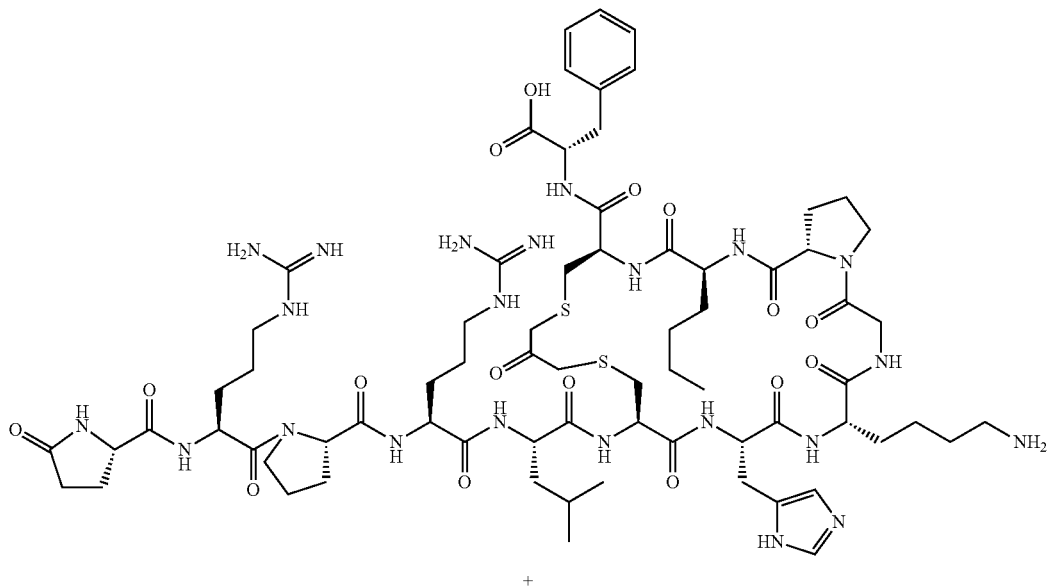

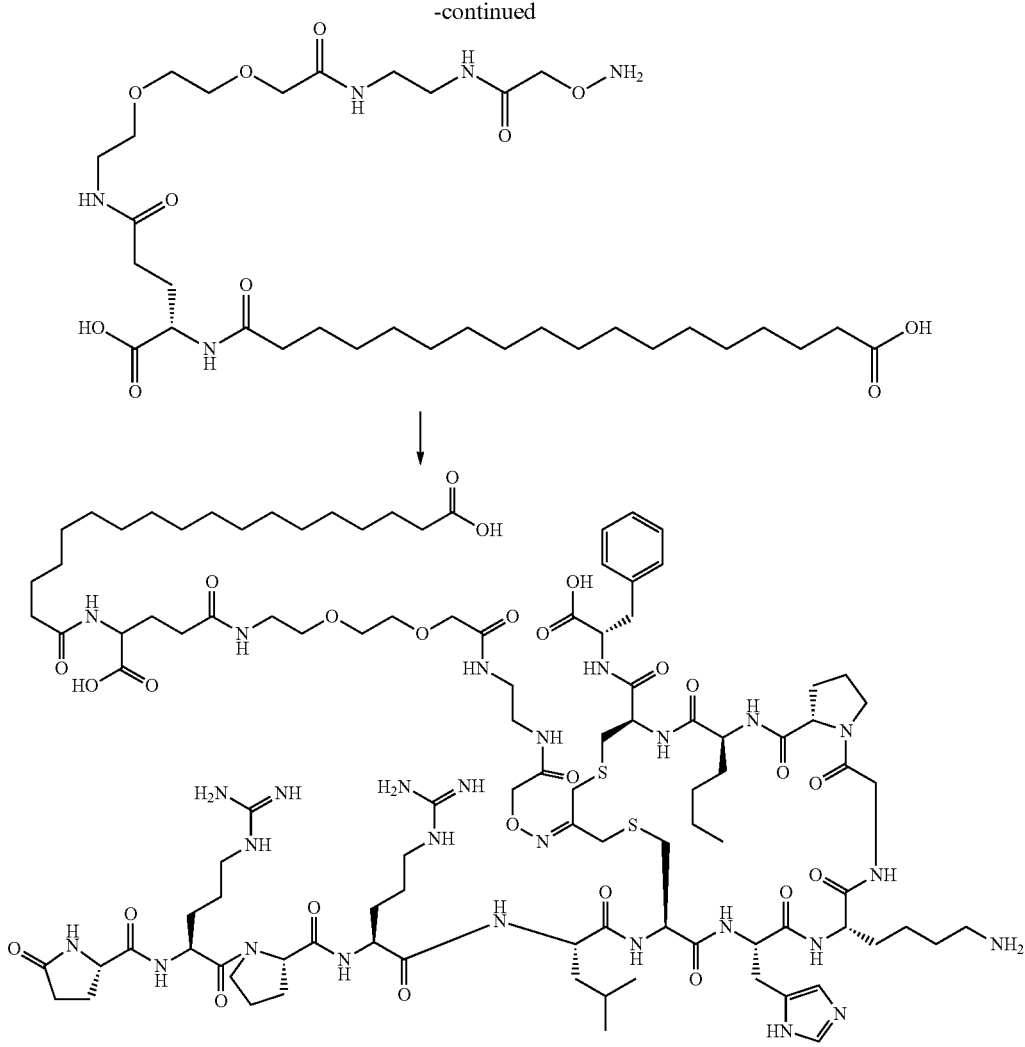

Into a solution of Example 64 ((S)-2-((3S,6R,14R,17S, 20S,28aS)-17-((1H-imidazol-5-yl)methyl)-20-(4-aminobutyl)-3-butyl-14-((S)-2-((S)-5-guanidino-2-((S)-1-((S)-5-guanidino-2-((S)-5-oxopyrrolidine-2-carboxamido)pentanoyl)pyrrolidine-2-carboxamido)pentanamido)-4-methylpentanamido)-1,4,10,15,18,21,24-heptaoxohexacosahydropyrrolo[2,1-i][1,23,4,7,10,13,16,19]dithiahexaazacyclohexacosine-6-carboxamido)-3-phenylpropanoic acid) (11.5 mg, 5.62 μmol) and (S)-1-(aminooxy)-19-carboxy-2,7,16,21-tetraoxo-9,12-dioxa-3,6,15,20-tetraazaoctatriacontan-38-oic acid compound with 2,2,2-trifluoroacetic acid (1:1) (9.19 mg, 0.011 mmol) in 100 nM Na phosphate buffer pH6.0 (1 ml) was added aniline (2.051 μl, 0.022 mmol) at RT. Addition of DMSO (50 μl) gave homogeneous solution. This reaction mixture was stirred at RT for 2 h. RP-HPLC eluting 15-60% MeCN/water with 0.1% TFA gave Example 66 (1-((Z)-((3S,6R,14R,17S, 20S,28aS)-17-((1H-imidazol-5-yl)methyl)-20-(4-aminobutyl)-3-butyl-6-((S)-1-carboxy-2-phenylethylcarbamoyl)-14-((S)-2-((S)-5-guanidino-2-((S)-1-((S)-5-guanidino-2-((S)-5-oxopyrrolidine-2-carboxamido)pentanoyl)pyrrolidine-2-carboxamido)pentanamido)-4-methylpentanamido)-1,4,15,18,21,24-hexaoxodocosahydropyrrolo[2,1-i][1,23,4,7,10,13,16,19]dithiahexaazacyclohexacosin-10(1H,9H,11H)-ylidene)aminooxy)-19-carboxy-2,7,16,21-tetraoxo-9,12-dioxa-3,6,15,20-tetraazaoctatriacontan-38-oic acid) (4.5 mg, 1.646 μmol, 29.3% yield). HRMS (method D) [(M+3)/3]; 759.7487 (observed), 759.7462 (expected). Retension time; 4.12 min.

Synthesis of the (S)-1-(aminooxy)-19-carboxv-2,7,16,21-tetraoxo-9,12-dioxa-3,6,15,20-tetraazaoctatriacontan-38-oic acid compound with 2,2,2-trifluoroacetic acid (1:1)

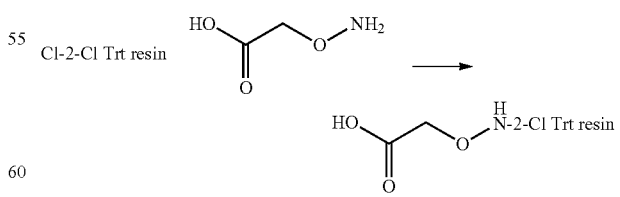

1-Chlorotrytyl chloride resin (1.55 mmol/g) (0.500 g, 0.775 mmol) in 100 mL glassware was swollen in DCM (20 ml) for 30 min and it was drained. a suspension of 2-(aminooxy)acetic acid hemihydrochloride (0.338 g, 3.10 mmol) and DIPEA (1.354 ml, 7.75 mmol) in NMP (7 ml)/DCM (4 ml) was added to the resin, which was shaken for 5 h. Solvent was drained. resin was rinsed with DCM/MeOH/DIPEA (17/2/1, 40 mL), DCM(50 mL), NMP(50 mL) DCM (50 mL) respectively. resulting resin was dried with KOH/NaOH overnight.

Resin (0.775 mmol) was charged into reaction vassel. 10 mL of 20% PIPERIDINE/NMP was added into resin, which suspension was agitated at RT for 5 min. After solvent was drained, additional 10 mL of 20% PIPERIDINE/NMP was added and agitated for 20 min at RT. Solution of HOAt

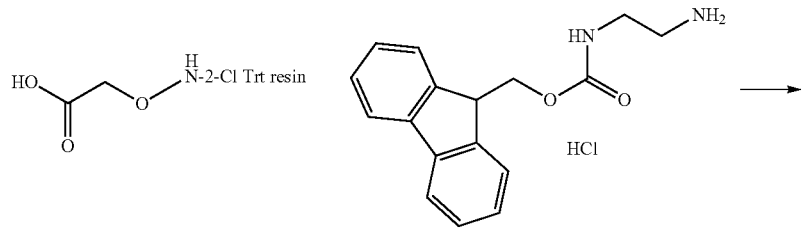

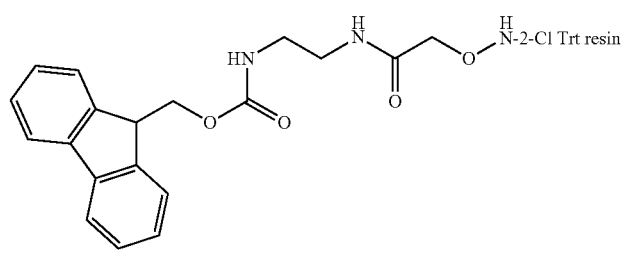

Resin (0.775 mmol) in 100 mL glassware was swollen in DCM (20 ml) for 30 min and it was drained. Into a suspension of (9H-fluoren-9-yl)methyl 2-aminoethylcarbamate hydrochloride (0.081 g, 0.775 mmol), HOAt (0.422 g, 3.10 mmol) and DIPEA (1.354 ml, 7.75 mmol) in NMP (8 ml) was added HBTU (1.176 g, 3.10 mmol) in NMP (2.5 ml), which was shaken for 2 h at RT. solvent was drained. resin was rinsed with NMP(10 mL), DCM(10 mL) respectively. The resulting resin was dried overnight.

(0.316 g, 2.325 mmol) and 1-(9H-fluoren-9-yl)-3-oxo-2,7,10-trioxa-4-azadodecan-12-oic acid (0.896 g, 2.325 mmol) in NMP (8 ml) was added into resin and DIC (0.362 ml, 2.325 mmol) in NMP (1 ml) was added. reaction mixture was agitated for 2 h at RT. Resin was filtered off and rinsed with NMP (10 ml) four times. The resulting resin was dried overnight.

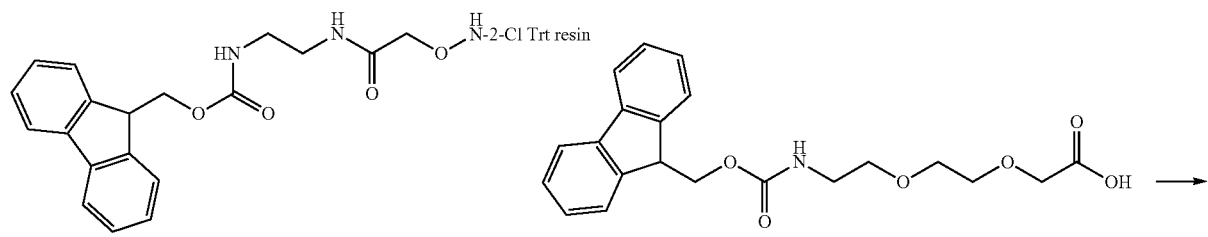

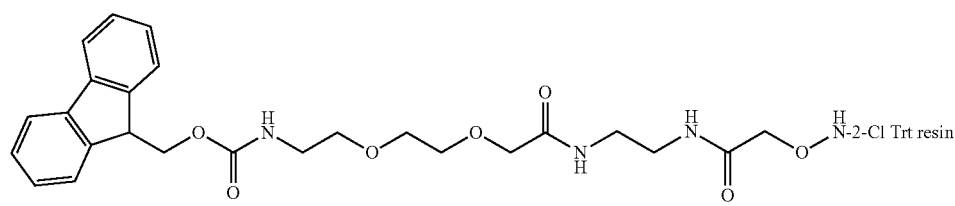

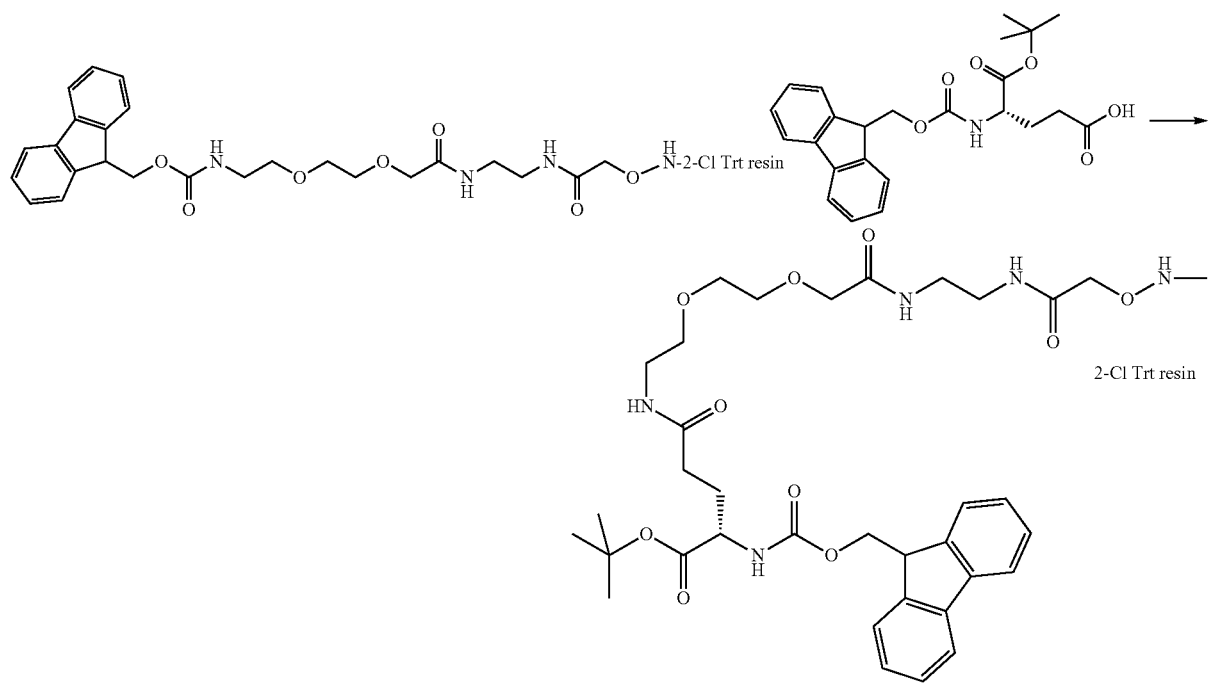

Resin (0.775 mmol) was charged into reaction vassel. 10 mL of 20% PIPERIDINE/NMP was added into resin, which suspension was agitated at RT for 5 min. After solvent was drained, additional 10 mL of 20% PIPERIDINE/NMP was added and agitated for 20 min at RT. Solution of HOAt (0.316 g, 2.325 mmol) and Fmoc-Glu-OtBu (0.989 g, 2.325 mmol) in NMP (8 ml) was added into resin and DIC (0.362 ml, 2.325 mmol) in NMP (2.00 ml) was added. The reaction mixture was agitated for 2 h at RT. Resin was filtered off and rinsed with NMP (10 ml) four times. The resulting resin was dried overnight.

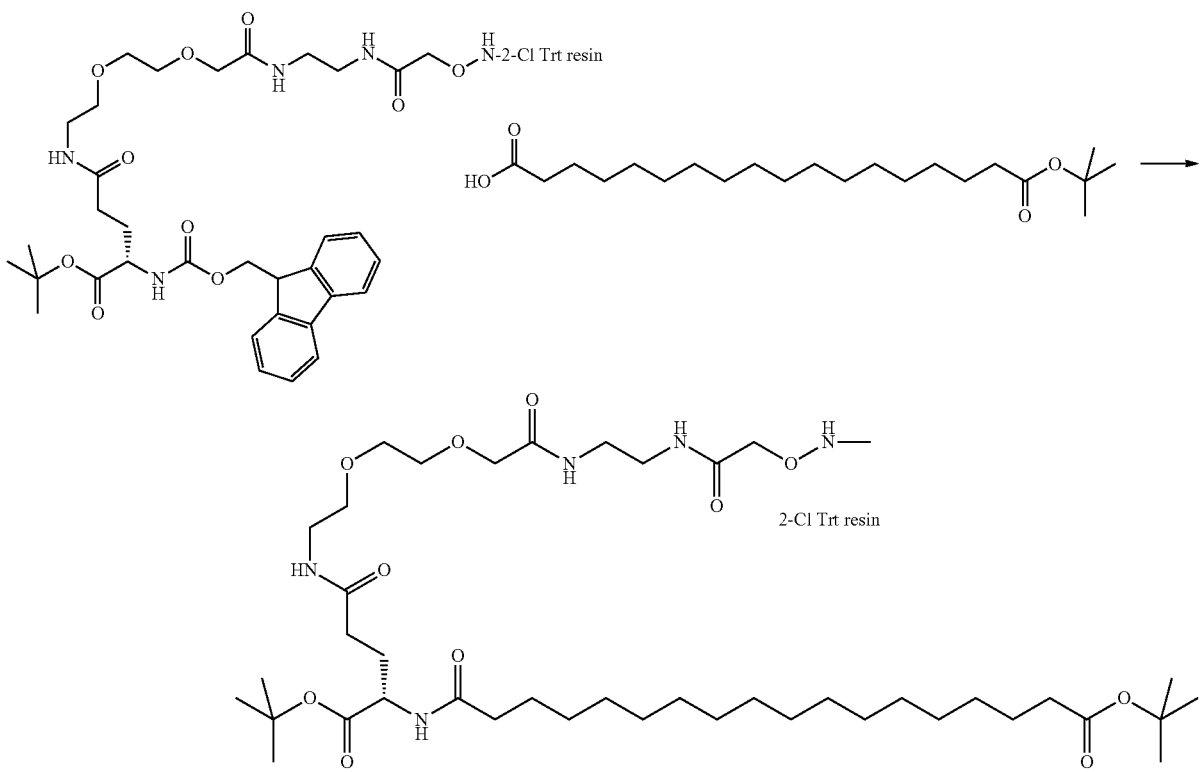

Resin (0.775 mmol) was charged into reaction vassel. 10 mL of 20% PIPERIDINE/NMP (0.775 mmol) was added into resin, which suspension was agitated at RT for 5 min. after solvent was drained, additional 10 mL of 20% PIPERIDINE/NMP (0.775 mmol) (0.775 mmol) was added and agitated for 20 min at RT. Solution of 18-tert-butoxy-18-oxooctadecanoic acid (0.862 g, 2.325 mmol) and HOAt (0.316 g, 2.325 mmol) in NMP (8 ml) was added into resin and DIC (0.362 ml, 2.325 mmol) in NMP (2.00 ml) was added. The reaction mixture was agitated for 4 h at RT. Resin was filtered off and rinsed with NMP (10 ml) four times. The resulting resin was dried overnight.

Examples 1-66 can be converted into their corresponding salt (e.g. hydrochloride, hydrobromide, sulfate, phosphate, citrate, acetate, lactate or another pharmaceutical salt for suitable for injection) with a polypeptide:salt ratio ranging from 1:1 to 1:4. For example, polypeptides of Examples 1-66 can be dissolved in water and converted into a salt using ion-exchange resins. Conversely where the isolated peptide is a salt, it can be converted to the free peptide by known method or directly to a different salt with the aid of ion-exchange resins.

The polypeptide in the examples below have been found to have $EC_{50}$ values in the range of about 0.01 nM to about 1100 nM for APJ receptor potency. The polypeptides in the examples below have been found to have a plasma stability higher than 2 minutes, higher than 5 minutes, higher than 10 minutes, higher than 20 minutes, higher than 50 minutes and higher than 60 minutes.

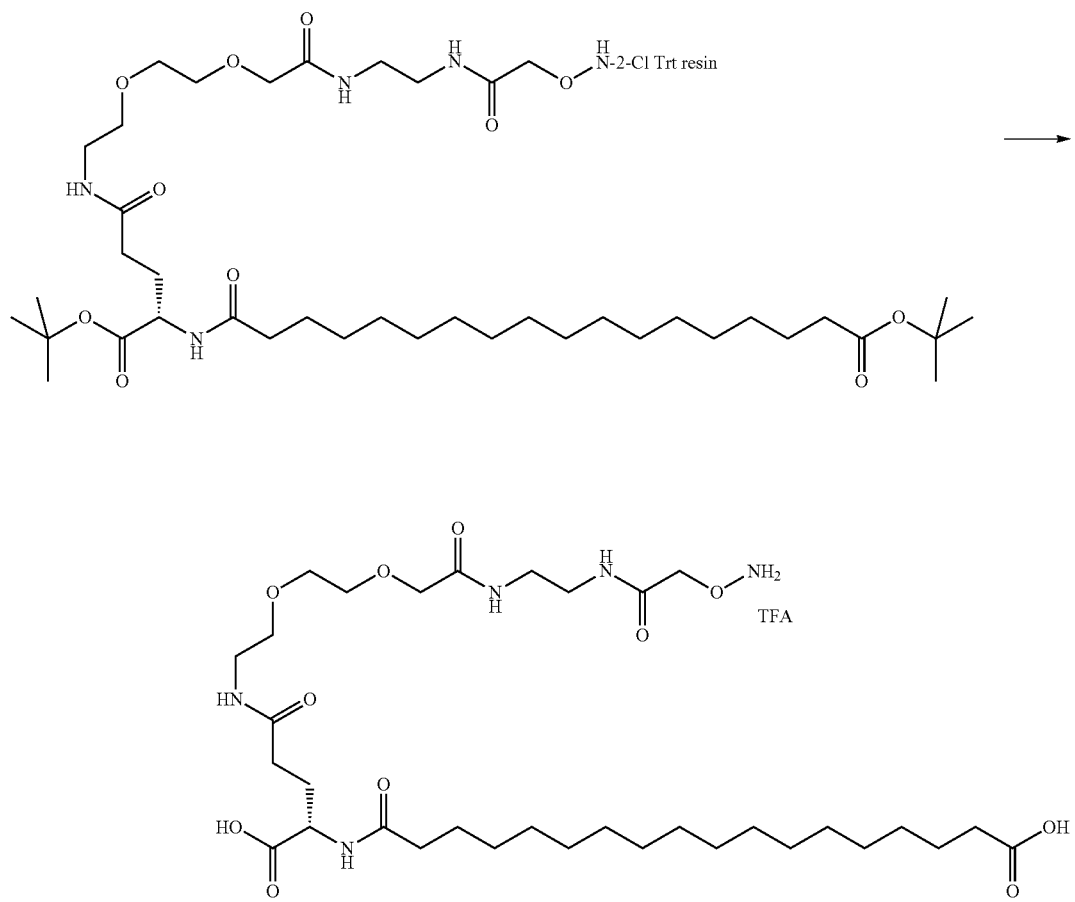

Resin (0.775 mmol) was treated with 20 mL of cleavage cocktail (TFA/TIPS/water=95/2.5/2.5) for 1.5 h at RT. Resin was removed by filtration and rinsed with TFA. The filtrate was concentrated in vacuo. RP-HPLC with C18 column eluting 15-50% MeCN/water with 0.1% TFA gave (S)-1-(aminooxy)-19-carboxy-2,7,16,21-tetraoxo-9,12-dioxa-3,6,15,20-tetraazaoctatriacontan-38-oic acid with 2,2,2-trifluoroacetic acid (1:1) (207 mg, 0.294 mmol, 37.9% yield). HRMS (method D) [M+1]; 704.4459 (observed), 704.4486 (expected). Retension time; 2.63 min.

The polypeptides of Examples 1-66 can be purified and isolated as described supra and/or by a combination of conventional purification techniques such as solvent extraction, column chromatography, liquid chromatography and recrystallization. Where the polypeptide isolated in the above Examples is a free compound, it can be converted to a suitable salt by the known method. Therefore, Peptides of It can be seen that the polypeptides of the invention are useful as agonist of the APJ receptor and therefore useful in the treatment of diseases and conditions responsive the activation of the APJ receptor, such as the diseases disclosed herein.

Having thus described exemplary embodiments of the present invention, it should be noted by those of ordinary skill in the art that the within disclosures are exemplary only and that various other alternatives, adaptations, and modifications may be made within the scope of the present invention. Accordingly, the present invention is not limited to the specific embodiments as illlustrated therein.

What is claimed is:

1. A polypeptide having Formula VII (SEQ ID NO: 82):

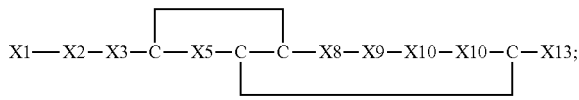

or an amide, an ester or a salt of the polypeptide, wherein
X1 is the N-terminus of the polypeptide and is either absent or is selected from pE, R, Isn, Q, A, K, and 5-amino-valeric acid;
X2 is R, A, r, N-Me-R, K, H, hF, hK, F, E or Orn;
X3 is P, A, a, p, 4-PhP, K, D or pipecolic acid;
X5 is L, Cha, A, D-L, N-Me-L, K, D, 4-PhF or F;
X8 is K, k, F, f, A, hF, N-Me-R, E or 4-amino-Isn;
X9 is G, N-Me-G, A, D, L, R or Aib;
X10 is P, A, p, 4-PhP or pipecolic acid,
X11 is M, D-Nle, Nle, N-Me-Nle, M(O), A, F, Y, L, K, 3-PyA or Cha; and
X13 is the C-terminus and is absent or is selected from F, f, N-Me-F, Nal, D-Nal, 3-Br—F, (S)-β-3-F, I, A, a, K, Dap, H and E;
wherein:
Nle is L-norleucine;
hF is L-homophenylalanine;
hK is L-lysine;
Nal is L-naphathaline;
Orn is ornithine;
Aib is α-aminoisobutyric acid;
Dap is (S)-2,3-diaminopropionic acid;
M(O) is methionine sulfone;
Cha is (S)-β-cyclohexylalanine;
4-amino-Isn is 4-aminopiperidine-4-carboxylic acid;
Isn is isonipecotinoyl;
pE is L-pyroglutamic acid;
3-PyA is 3-(3-pyridyl)-L-alanine;
4-PhF is 4-Phenyl-L-phenylalanine;
wherein the amino group in the side chain of K, Orn, Dap, hK or 4-amino-Isn is optionally linked to a lipophilic group via an amide bond.

2. The polypeptide according to claim 1 wherein X1 is pE.

3. The polypeptide according to claim 1 wherein X1 is absent.

4. The polypeptide according to claim 3 wherein the N-terminus is an amide.

5. The polypeptide according to claim 4, wherein the N-terminus is an amide of Formula —NHR and R is acetyl, benzoyl, phenacyl, succinyl, octanoyl, 4-phenylbutanoyl, 4-Cl-Ph-(CH2)3C(O)-, or Ph-CH2CH2NHC(0).

6. The polypeptide of claim 1 wherein the N-terminus is an amide of Formula NHR1 wherein R1 is CH$_3$C(O)—, CH$_3$—(O—CH$_2$CH$_2$)$_m$, —C(O)—, Palmitoyl(O2Oc)$_p$, Myristoyl(O2Oc)$_p$, Lauroyl(O2Oc)$_p$ or Ph-CH$_2$CH$_2$NHC(O)—; and wherein
p is an integer of 1 to 4;
m is an integer of 1 to 12;
Lauroyl(O2Oc) is C$_{11}$H$_{23}$C(O)NH—(CH$_2$)$_2$—O—(CH$_2$)$_2$—O—CH$_2$—C(O)—;
Myristoyl(O2Oc) is C$_{13}$H$_{27}$C(O)NH—(CH$_2$)$_2$—O—(CH$_2$)$_2$—O—CH$_2$—C(O)—;
Palmitoyl(O2Oc) is C$_{15}$H$_{31}$C(O)NH—(CH$_2$)$_2$—O—(CH$_2$)$_2$—O—CH$_2$—C(O).

7. The polypeptide according to claim 1 wherein X13 is F.

8. The polypeptide according to claim 1 wherein X13 is absent.

9. The polypeptide according to claim 8 wherein the C-terminus is an amide.

10. The polypeptide according to claim 9 wherein the C-terminus is an amide of Formula —C(O)—R2 and R2 is —NH$_2$, —NH-Me, —NH-NHBn, or —NH—(CH$_2$)$_2$-Ph.

11. The polypeptide according to claim 1 wherein X5 is L.

12. The polypeptide according to claim 1 wherein X8 is K.

13. The polypeptide according to claim 1 wherein X9 is G.

14. The polypeptide according to claim 1 wherein X11 is Nle.

15. The polypeptide according to claim 1 which is:
pE-R-P-C**-L-C*-C**-K-G-P-Nle-C*-F-OH (SEQ ID NO: 35),
wherein the two amino acids labeled with "*" represent the amino acids forming a disulfide and wherein the two amino acids labeled with "**" represent the amino acids forming a disulfide via their side chain.

16. A method of treating a disease or disorder responsive to the agonism of the APJ receptor, in a subject in need thereof, comprising administering to the subject a therapeutically effective amount of a polypeptide according to claim 9, wherein treating refers to ameliorating the disease or disorder, and wherein the disease or disorder is selected from acute decompensated heart failure (ADHR, chronic heart failure, pulmonary hypertension, atrial fibrillation, Bruqada syndrome, ventricular tachycardia, atherosclerosis, hypertension, restenosis, ischemic cardiovascular diseases, cardiomyopathy, cardiac fibrosis, arrhythmia, water retention, diabetes, obesity, peripheral arterial disease, cerebrovascular accidents, transient ischemic attacks, traumatic brain injuries, amyotrophic lateral sclerosis, burn injuries and preeclampsia.

17. A pharmaceutical composition comprising a therapeutically effective amount of a polypeptide according to claim 1 and one or more pharmaceutically acceptable carriers.

* * * * *

UNITED STATES PATENT AND TRADEMARK OFFICE
CERTIFICATE OF CORRECTION

Page 1 of 1

PATENT NO. : 9,982,017 B2
APPLICATION NO. : 14/714914
DATED : May 29, 2018
INVENTOR(S) : Zecri et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 259 days.

Signed and Sealed this
Eighteenth Day of December, 2018

Andrei Iancu
*Director of the United States Patent and Trademark Office*

SEQUENCE LISTING

<160> NUMBER OF SEQ ID NOS: 94

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu, Arg, Gln, Isn or absent
<220> FEATURE:
<221> NAME/KEY: MOD_RES
<222> LOCATION: (5)..(5)
<223> OTHER INFORMATION: Leu or Cha
<220> FEATURE:
<221> NAME/KEY: MOD_RES
<222> LOCATION: (6)..(6)
<223> OTHER INFORMATION: Cys, D-Cys, homoCys, D-homoCys, Lys, Asp, Orn,
      Dab or Glu
<220> FEATURE:
<221> NAME/KEY: MOD_RES
<222> LOCATION: (7)..(7)
<223> OTHER INFORMATION: His, Aib, Phe, Lys(Lauroyl) or Lys(palmitoyl)
<220> FEATURE:
<221> NAME/KEY: MOD_RES
<222> LOCATION: (8)..(8)
<223> OTHER INFORMATION: Lys, Phe or 4-amino-Isn
<220> FEATURE:
<221> NAME/KEY: MOD_RES
<222> LOCATION: (9)..(9)
<223> OTHER INFORMATION: Gly or Aib
<220> FEATURE:
<221> NAME/KEY: MOD_RES
<222> LOCATION: (11)..(11)
<223> OTHER INFORMATION: Nle or Cha
<220> FEATURE:
<221> NAME/KEY: MOD_RES
<222> LOCATION: (12)..(12)
<223> OTHER INFORMATION: Cys, D-Cys, homoCys, D-homoCys, Lys, Asp, Orn,
      Dab, Glu, Phe or D-Phe
<220> FEATURE:
<221> NAME/KEY: MOD_RES
<222> LOCATION: (13)..(13)
<223> OTHER INFORMATION: Phe, D-Phe, Lys(Lauroyl), Lys(palmitoyl) or
      absent

<400> SEQUENCE: 1

Xaa Arg Pro Arg Xaa Xaa Xaa Xaa Xaa Pro Xaa Xaa Xaa
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu, Arg, Isn, Gln, Ala, Lys(palmitoyl),
      Lys(Myristoyl), Lys(Lauroyl), 5-amino-valeric acid, Lys or absent
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp, 4-PhF
      or Phe
<220> FEATURE:
<221> NAME/KEY: MOD_RES
<222> LOCATION: (7)..(7)
<223> OTHER INFORMATION: His, D-His, Ala, N-Me-Ala, D-Ala, Aib,
      Lys(Lauroyl), Lys(palmitoyl), Nal, Phe, Pro, Dap, Asn, Glu, Cys or
      Lys

```
<220> FEATURE:
<221> NAME/KEY: MOD_RES
<222> LOCATION: (8)..(8)
<223> OTHER INFORMATION: Lys, D-Lys, Phe, D-Phe, Ala, homoPhe, N-Me-Arg,
      Glu or 4-amino-Isn
<220> FEATURE:
<221> NAME/KEY: MOD_RES
<222> LOCATION: (9)..(9)
<223> OTHER INFORMATION: Gly, N-Me-Gly, Ala, Asp, Leu, Arg or Aib
<220> FEATURE:
<221> NAME/KEY: MOD_RES
<222> LOCATION: (11)..(11)
<223> OTHER INFORMATION: Met, D-Nle, Nle, N-Me-Nle, M(O), Ala, Phe, Tyr,
      Leu, Lys(palmitoyl), 3-PyA, Cha or Lys
<220> FEATURE:
<221> NAME/KEY: MOD_RES
<222> LOCATION: (13)..(13)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap, His, Glu, Lys(Lauroyl),
      Lys(Myristoyl), Lys(palmitoyl), Lys(O2Oc-Palmitoyl),
      Dap(Palmitoyl) or absent

<400> SEQUENCE: 2

Xaa Arg Pro Arg Xaa Cys Xaa Xaa Xaa Pro Xaa Cys Xaa
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, PyroGlu, Isn, Gln, Ala, Lys(palmitoyl),
      Lys(Myristoyl), Lys(Lauroyl), 5-amino-valeric acid, Lys or absent
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp, 4-PhF
      or Phe
<220> FEATURE:
<221> NAME/KEY: MOD_RES
<222> LOCATION: (6)..(6)
<223> OTHER INFORMATION: Cys, D-Cys, homoCys, D-homoCys, Lys, Asp, Orn,
      Dab or Glu
<220> FEATURE:
<221> NAME/KEY: MOD_RES
<222> LOCATION: (7)..(7)
<223> OTHER INFORMATION: His, D-His, Ala, N-Me-Ala, D-Ala, Aib,
      Lys(Lauroyl), Lys(palmitoyl), Nal, Phe, Pro, Dap, Asn, Glu, Cys or
      Lys
<220> FEATURE:
<221> NAME/KEY: MOD_RES
<222> LOCATION: (11)..(11)
<223> OTHER INFORMATION: Met, D-Nle, Nle, N-Me-Nle, M(O), Ala, Phe, Tyr,
      Leu, Lys(palmitoyl), 3-PyA, Cha or Lys
<220> FEATURE:
<221> NAME/KEY: MOD_RES
<222> LOCATION: (12)..(12)
<223> OTHER INFORMATION: Cys, D-Cys, homoCys, D-homoCys, Lys, Asp, Orn,
      Dab, Glu, Phe or D-Phe
<220> FEATURE:
<221> NAME/KEY: MOD_RES
<222> LOCATION: (13)..(13)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap, His, Glu, Lys(Lauroyl),
      Lys(Myristoyl), Lys(palmitoyl), Lys(O2Oc-Palmitoyl),
      Dap(Palmitoyl) or absent

<400> SEQUENCE: 3

Xaa Arg Pro Arg Xaa Xaa Xaa Lys Gly Pro Xaa Xaa Xaa
1               5                   10
```

```
<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, PyroGlu, Isn, Gln, Ala, Lys(palmitoyl),
      Lys(Myristoyl), Lys(Lauroyl), 5-amino-valeric acid, Lys or absent
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp, 4-PhF
      or Phe
<220> FEATURE:
<221> NAME/KEY: MOD_RES
<222> LOCATION: (7)..(7)
<223> OTHER INFORMATION: His, D-His, Ala, N-Me-Ala, D-Ala, Aib,
      Lys(Lauroyl), Lys(palmitoyl), Nal, Phe, Pro, Dap, Asn, Glu, Cys or
      Lys
<220> FEATURE:
<221> NAME/KEY: MOD_RES
<222> LOCATION: (11)..(11)
<223> OTHER INFORMATION: Met, D-Nle, Nle, N-Me-Nle, M(O), Ala, Phe, Tyr,
      Leu, Lys(palmitoyl), 3-PyA, Cha or Lys
<220> FEATURE:
<221> NAME/KEY: MOD_RES
<222> LOCATION: (13)..(13)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap, His, Glu, Lys(Lauroyl),
      Lys(Myristoyl), Lys(palmitoyl), Lys(O2Oc-Palmitoyl),
      Dap(Palmitoyl) or absent

<400> SEQUENCE: 4

Xaa Arg Pro Arg Xaa Cys Xaa Lys Gly Pro Xaa Cys Xaa
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, PyroGlu, Isn, Gln, Ala, Lys(palmitoyl),
      Lys(Myristoyl), Lys(Lauroyl), 5-amino-valeric acid, Lys or absent
<220> FEATURE:
<221> NAME/KEY: MOD_RES
<222> LOCATION: (2)..(2)
<223> OTHER INFORMATION: Arg, Ala, D-Arg, N-Me-Arg, Lys, His, homoPhe,
      HomoLys, Phe, Glu or Orn
<220> FEATURE:
<221> NAME/KEY: MOD_RES
<222> LOCATION: (4)..(4)
<223> OTHER INFORMATION: Arg, Ala, D-Arg, N-Me-Arg, Phe, Glu or Cys
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp, 4-PhF
      or Phe
<220> FEATURE:
<221> NAME/KEY: MOD_RES
<222> LOCATION: (8)..(8)
<223> OTHER INFORMATION: Lys, D-Lys, Phe, D-Phe, Ala, homoPhe, N-Me-Arg,
      Glu or 4-amino-Isn
<220> FEATURE:
<221> NAME/KEY: MOD_RES
<222> LOCATION: (9)..(9)
<223> OTHER INFORMATION: Gly, N-Me-Gly, Ala, Asp, Leu, Arg or Aib
<220> FEATURE:
```

```
<221> NAME/KEY: MOD_RES
<222> LOCATION: (10)..(10)
<223> OTHER INFORMATION: Pro, Ala, D-Pro, 4-PhP or pipecolic acid
<220> FEATURE:
<221> NAME/KEY: MOD_RES
<222> LOCATION: (11)..(11)
<223> OTHER INFORMATION: Met, D-Nle, Nle, N-Me-Nle, M(O), Ala, Phe, Tyr,
      Leu, Lys(palmitoyl), 3-PyA, Cha or Lys
<220> FEATURE:
<221> NAME/KEY: MOD_RES
<222> LOCATION: (13)..(13)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap, His, Glu, Lys(Lauroyl),
      Lys(Myristoyl), Lys(palmitoyl), Lys(O2Oc-Palmitoyl),
      Dap(Palmitoyl) or absent

<400> SEQUENCE: 5

Xaa Xaa Cys Xaa Xaa Cys Cys Xaa Xaa Xaa Xaa Cys Xaa
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, PyroGlu, Isn, Gln, Ala, Lys(palmitoyl),
      Lys(Myristoyl), Lys(Lauroyl), 5-amino-valeric acid, Lys or absent
<220> FEATURE:
<221> NAME/KEY: MOD_RES
<222> LOCATION: (2)..(2)
<223> OTHER INFORMATION: Arg, Ala, D-Arg, N-Me-Arg, Lys, His, homoPhe,
      HomoLys, Phe, Glu or Orn
<220> FEATURE:
<221> NAME/KEY: MOD_RES
<222> LOCATION: (3)..(3)
<223> OTHER INFORMATION: Pro, Ala, D-Ala, D-Pro, 4-PhP, Lys, Asp,
      pipecolic acid or Cys
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp, 4-PhF
      or Phe
<220> FEATURE:
<221> NAME/KEY: MOD_RES
<222> LOCATION: (8)..(8)
<223> OTHER INFORMATION: Lys, D-Lys, Phe, D-Phe, Ala, homoPhe, N-Me-Arg,
      Glu or 4-amino-Isn
<220> FEATURE:
<221> NAME/KEY: MOD_RES
<222> LOCATION: (9)..(9)
<223> OTHER INFORMATION: Gly, N-Me-Gly, Ala, Asp, Leu, Arg or Aib
<220> FEATURE:
<221> NAME/KEY: MOD_RES
<222> LOCATION: (10)..(10)
<223> OTHER INFORMATION: Pro, Ala, D-Pro, 4-PhP or pipecolic acid
<220> FEATURE:
<221> NAME/KEY: MOD_RES
<222> LOCATION: (11)..(11)
<223> OTHER INFORMATION: Met, D-Nle, Nle, N-Me-Nle, M(O), Ala, Phe, Tyr,
      Leu, Lys(palmitoyl), 3-PyA, Cha or Lys
<220> FEATURE:
<221> NAME/KEY: MOD_RES
<222> LOCATION: (13)..(13)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap, His, Glu, Lys(Lauroyl),
      Lys(Myristoyl), Lys(palmitoyl), Lys(O2Oc-Palmitoyl),
      Dap(Palmitoyl) or absent

<400> SEQUENCE: 6

Xaa Xaa Xaa Cys Xaa Cys Cys Xaa Xaa Xaa Xaa Cys Xaa
1               5                   10
```

```
<210> SEQ ID NO 7
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Trp Phe Lys Ala Phe Tyr Asp Lys Val Ala Glu Lys Phe Lys Glu
1               5                   10                  15

Ala Phe

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 8

Glu Arg Pro Arg Leu Lys His Phe Gly Pro Leu Asp
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 9

Glu Arg Pro Arg Leu Lys His Phe Gly Pro Leu Glu
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (6)..(6)
<223> OTHER INFORMATION: Orn
<220> FEATURE:
<221> NAME/KEY: MOD_RES
```

<222> LOCATION: (11)..(11)
<223> OTHER INFORMATION: Nle

<400> SEQUENCE: 10

Glu Arg Pro Arg Leu Xaa His Phe Gly Pro Leu Asp
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (6)..(6)
<223> OTHER INFORMATION: Dab
<220> FEATURE:
<221> NAME/KEY: MOD_RES
<222> LOCATION: (11)..(11)
<223> OTHER INFORMATION: Nle

<400> SEQUENCE: 11

Glu Arg Pro Arg Leu Xaa His Phe Gly Pro Leu Asp
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 12

Glu Arg Pro Arg Leu Lys Phe Lys Gly Pro Leu Phe
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (12)..(12)
<223> OTHER INFORMATION: D-Phe

<400> SEQUENCE: 13

Glu Arg Pro Arg Leu Lys Phe Lys Gly Pro Leu Phe
1               5                   10

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Nle

<400> SEQUENCE: 14

Gln Arg Pro Arg Leu Cys Phe Lys Gly Pro Leu Cys Phe Gly Gly
1               5                   10                  15

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 15

Glu Arg Pro Arg Leu Cys His Lys Gly Pro Leu Cys Phe
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (7)..(7)
<223> OTHER INFORMATION: Aib
<220> FEATURE:
<221> NAME/KEY: MOD_RES
<222> LOCATION: (11)..(11)
<223> OTHER INFORMATION: Nle

<400> SEQUENCE: 16

Glu Arg Pro Arg Leu Cys Xaa Lys Gly Pro Leu Cys Phe
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (1)..(1)
<223> OTHER INFORMATION: PyroGlu
<220> FEATURE:
<221> NAME/KEY: MOD_RES
<222> LOCATION: (7)..(7)
<223> OTHER INFORMATION: Aib
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (13)..(13)
<223> OTHER INFORMATION: D-Phe

<400> SEQUENCE: 17

Glu Arg Pro Arg Leu Cys Xaa Lys Gly Pro Leu Cys Phe
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Isn
<220> FEATURE:
<221> NAME/KEY: MOD_RES
<222> LOCATION: (7)..(7)
<223> OTHER INFORMATION: Aib
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (13)..(13)
<223> OTHER INFORMATION: D-Phe

<400> SEQUENCE: 18

Xaa Arg Pro Arg Leu Cys Xaa Lys Gly Pro Leu Cys Phe
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 19

Glu Arg Pro Arg Leu Cys His Lys Gly Pro Leu Cys
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (13)..(13)
<223> OTHER INFORMATION: D-Phe

<400> SEQUENCE: 20

Glu Arg Pro Arg Leu Cys His Lys Gly Pro Leu Cys Phe
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (5)..(5)
<223> OTHER INFORMATION: Cha
<220> FEATURE:
<221> NAME/KEY: MOD_RES
<222> LOCATION: (11)..(11)
<223> OTHER INFORMATION: Cha

<400> SEQUENCE: 21

Glu Arg Pro Arg Xaa Cys His Lys Gly Pro Xaa Cys Phe
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 22

Glu Arg Pro Arg Leu Cys Phe Lys Gly Pro Leu Cys Phe
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Nle
```

```
<400> SEQUENCE: 23

Arg Pro Arg Leu Cys His Lys Gly Pro Leu Cys Phe
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Nle

<400> SEQUENCE: 24

Arg Arg Pro Arg Leu Cys His Lys Gly Pro Leu Cys Phe
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Isn
<220> FEATURE:
<221> NAME/KEY: MOD_RES
<222> LOCATION: (11)..(11)
<223> OTHER INFORMATION: Nle

<400> SEQUENCE: 25

Xaa Arg Pro Arg Leu Cys His Lys Gly Pro Leu Cys Phe
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 26

Glu Arg Pro Arg Leu Cys His Phe Gly Pro Leu Cys
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: PyroGlu
<220> FEATURE:
<221> NAME/KEY: MOD_RES
<222> LOCATION: (9)..(9)
<223> OTHER INFORMATION: Aib
<220> FEATURE:
<221> NAME/KEY: MOD_RES
<222> LOCATION: (11)..(11)
<223> OTHER INFORMATION: Nle

<400> SEQUENCE: 27

Glu Arg Pro Arg Leu Cys His Lys Xaa Pro Leu Cys Phe
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (8)..(8)
<223> OTHER INFORMATION: 4-NH-Isn
<220> FEATURE:
<221> NAME/KEY: MOD_RES
<222> LOCATION: (11)..(11)
<223> OTHER INFORMATION: Nle

<400> SEQUENCE: 28

Glu Arg Pro Arg Leu Cys His Xaa Gly Pro Leu Cys Phe
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 29

Glu Arg Pro Arg Leu Cys His Lys Gly Pro Leu Cys Lys
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle
```

<400> SEQUENCE: 30

Glu Arg Pro Arg Leu Cys Lys Lys Gly Pro Leu Cys Phe
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: O2Oc
<220> FEATURE:
<221> NAME/KEY: MOD_RES
<222> LOCATION: (12)..(12)
<223> OTHER INFORMATION: Nle

<400> SEQUENCE: 31

Xaa Gln Arg Pro Arg Leu Cys His Lys Gly Pro Leu Cys Phe
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: O2Oc
<220> FEATURE:
<221> NAME/KEY: MOD_RES
<222> LOCATION: (12)..(12)
<223> OTHER INFORMATION: Nle

<400> SEQUENCE: 32

Xaa Gln Arg Pro Arg Leu Cys His Lys Gly Pro Leu Cys Phe
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 33

Glu Arg Pro Arg Leu Cys His Lys Gly Pro Leu Cys Lys
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic

```
                              peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 34

Glu Arg Pro Arg Leu Cys Lys Lys Gly Pro Leu Cys Phe
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 35

Glu Arg Pro Cys Leu Cys Cys Lys Gly Pro Leu Cys Phe
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 36

Glu Arg Cys Arg Leu Cys Cys Lys Gly Pro Leu Cys Phe
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (2)..(2)
<223> OTHER INFORMATION: D-Arg
<220> FEATURE:
<221> NAME/KEY: MOD_RES
<222> LOCATION: (11)..(11)
<223> OTHER INFORMATION: Nle
```

```
<400> SEQUENCE: 37

Glu Arg Pro Arg Leu Cys His Lys Gly Pro Leu Cys Phe
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 38

Glu Phe Pro Arg Leu Cys His Lys Gly Pro Leu Cys Phe
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 39

Glu Glu Pro Arg Leu Cys His Lys Gly Pro Leu Cys Phe
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (3)..(3)
<223> OTHER INFORMATION: D-Pro
<220> FEATURE:
<221> NAME/KEY: MOD_RES
<222> LOCATION: (11)..(11)
<223> OTHER INFORMATION: Nle

<400> SEQUENCE: 40

Glu Arg Pro Arg Leu Cys His Lys Gly Pro Leu Cys Phe
1               5                   10

<210> SEQ ID NO 41
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 41

Glu Arg Lys Arg Leu Cys His Lys Gly Pro Leu Cys Phe
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 42

Glu Arg Asp Arg Leu Cys His Lys Gly Pro Leu Cys Phe
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 43

Glu Arg Pro Phe Leu Cys His Lys Gly Pro Leu Cys Phe
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle
```

<400> SEQUENCE: 44

Glu Arg Pro Arg Lys Cys His Lys Gly Pro Leu Cys Phe
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 45

Glu Arg Pro Arg Leu Cys His Glu Gly Pro Leu Cys Phe
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 46

Glu Arg Pro Arg Leu Cys His Lys Asp Pro Leu Cys Phe
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 47

Glu Arg Pro Glu Leu Cys His Lys Gly Pro Leu Cys Phe
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Description of Artificial Sequence: Synthetic

```
    peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (5)..(5)
<223> OTHER INFORMATION: 4-PhF
<220> FEATURE:
<221> NAME/KEY: MOD_RES
<222> LOCATION: (11)..(11)
<223> OTHER INFORMATION: Nle

<400> SEQUENCE: 48

Glu Arg Pro Arg Phe Cys His Lys Gly Pro Leu Cys Phe
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 49

Glu Arg Pro Arg Asp Cys His Lys Gly Pro Leu Cys Phe
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 50

Glu Arg Pro Arg Leu Cys Glu Lys Gly Pro Leu Cys Phe
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle
```

```
<400> SEQUENCE: 51

Glu Arg Pro Arg Leu Cys His Lys Leu Pro Leu Cys Phe
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 52

Glu Arg Pro Arg Leu Cys His Lys Arg Pro Leu Cys Phe
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (10)..(10)
<223> OTHER INFORMATION: Pipecolic acid
<220> FEATURE:
<221> NAME/KEY: MOD_RES
<222> LOCATION: (11)..(11)
<223> OTHER INFORMATION: Nle

<400> SEQUENCE: 53

Glu Arg Pro Arg Leu Cys His Lys Gly Xaa Leu Cys Phe
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: 3-PyA

<400> SEQUENCE: 54

Glu Arg Pro Arg Leu Cys His Lys Gly Pro Ala Cys Phe
1               5                   10

<210> SEQ ID NO 55
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 55

Glu Arg Pro Arg Leu Cys His Lys Gly Pro Leu Cys His
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 56

Glu Arg Pro Arg Leu Cys His Lys Gly Pro Leu Cys Glu
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 57

Glu Arg Pro Arg Leu Cys His Lys Gly Pro Leu Cys
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle
```

```
<220> FEATURE:
<221> NAME/KEY: MOD_RES
<222> LOCATION: (12)..(12)
<223> OTHER INFORMATION: homoCys

<400> SEQUENCE: 58

Glu Arg Pro Arg Leu Cys His Lys Gly Pro Leu Cys Phe
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (6)..(6)
<223> OTHER INFORMATION: homoCys
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (12)..(12)
<223> OTHER INFORMATION: homoCys

<400> SEQUENCE: 59

Glu Arg Pro Arg Leu Cys His Lys Gly Pro Leu Cys Phe
1               5                   10

<210> SEQ ID NO 60
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (6)..(6)
<223> OTHER INFORMATION: D-Cys
<220> FEATURE:
<221> NAME/KEY: MOD_RES
<222> LOCATION: (11)..(11)
<223> OTHER INFORMATION: Nle

<400> SEQUENCE: 60

Glu Arg Pro Arg Leu Cys His Lys Gly Pro Leu Cys Phe
1               5                   10

<210> SEQ ID NO 61
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
```

```
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (12)..(12)
<223> OTHER INFORMATION: D-homoCys

<400> SEQUENCE: 61

Glu Arg Pro Arg Leu Cys His Lys Gly Pro Leu Cys Phe
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (6)..(6)
<223> OTHER INFORMATION: D-homoCys
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (12)..(12)
<223> OTHER INFORMATION: D-homoCys

<400> SEQUENCE: 62

Glu Arg Pro Arg Leu Cys His Lys Gly Pro Leu Cys Phe
1               5                   10

<210> SEQ ID NO 63
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (12)..(12)
<223> OTHER INFORMATION: D-Cys

<400> SEQUENCE: 63

Glu Arg Pro Arg Leu Cys His Lys Gly Pro Leu Cys Phe
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: PyroGlu
<220> FEATURE:
<221> NAME/KEY: MOD_RES
<222> LOCATION: (6)..(6)
<223> OTHER INFORMATION: D-Cys
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (12)..(12)
<223> OTHER INFORMATION: D-Cys

<400> SEQUENCE: 64

Glu Arg Pro Arg Leu Cys His Lys Gly Pro Leu Cys Phe
1               5                   10

<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: O2Oc
<220> FEATURE:
<221> NAME/KEY: MOD_RES
<222> LOCATION: (2)..(2)
<223> OTHER INFORMATION: O2Oc
<220> FEATURE:
<221> NAME/KEY: MOD_RES
<222> LOCATION: (13)..(13)
<223> OTHER INFORMATION: Nle
<220> FEATURE:
<221> NAME/KEY: MOD_RES
<222> LOCATION: (15)..(15)
<223> OTHER INFORMATION: D-Phe

<400> SEQUENCE: 65

Xaa Xaa Gln Arg Pro Arg Leu Cys His Lys Gly Pro Leu Cys Phe
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: O2Oc
<220> FEATURE:
<221> NAME/KEY: MOD_RES
<222> LOCATION: (2)..(2)
<223> OTHER INFORMATION: O2Oc
<220> FEATURE:
<221> NAME/KEY: MOD_RES
<222> LOCATION: (3)..(3)
<223> OTHER INFORMATION: O2Oc
<220> FEATURE:
<221> NAME/KEY: MOD_RES
<222> LOCATION: (14)..(14)
<223> OTHER INFORMATION: Nle
<220> FEATURE:
<221> NAME/KEY: MOD_RES
<222> LOCATION: (16)..(16)
<223> OTHER INFORMATION: D-Phe
```

```
<400> SEQUENCE: 66

Xaa Xaa Xaa Gln Arg Pro Arg Leu Cys His Lys Gly Pro Leu Cys Phe
1               5                   10                  15

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: O2Oc
<220> FEATURE:
<221> NAME/KEY: MOD_RES
<222> LOCATION: (2)..(2)
<223> OTHER INFORMATION: O2Oc
<220> FEATURE:
<221> NAME/KEY: MOD_RES
<222> LOCATION: (3)..(3)
<223> OTHER INFORMATION: O2Oc
<220> FEATURE:
<221> NAME/KEY: MOD_RES
<222> LOCATION: (4)..(4)
<223> OTHER INFORMATION: O2Oc
<220> FEATURE:
<221> NAME/KEY: MOD_RES
<222> LOCATION: (15)..(15)
<223> OTHER INFORMATION: Nle
<220> FEATURE:
<221> NAME/KEY: MOD_RES
<222> LOCATION: (17)..(17)
<223> OTHER INFORMATION: D-Phe

<400> SEQUENCE: 67

Xaa Xaa Xaa Xaa Gln Arg Pro Arg Leu Cys His Lys Gly Pro Leu Cys
1               5                   10                  15

Phe

<210> SEQ ID NO 68
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 68

Glu Arg Pro Arg Leu Cys His Lys Gly Pro Leu Cys Phe
1               5                   10

<210> SEQ ID NO 69
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
```

```
<220> FEATURE:
<221> NAME/KEY: MOD_RES
<222> LOCATION: (11)..(11)
<223> OTHER INFORMATION: Nle

<400> SEQUENCE: 69

Glu Arg Pro Arg Leu Cys His Lys Gly Pro Leu Cys Phe
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 70

Glu Arg Pro Arg Leu Cys His Lys Gly Pro Leu Cys
1               5                   10

<210> SEQ ID NO 71
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 71

Glu Arg Pro Arg Leu Cys His Lys Gly Pro Leu Cys Phe
1               5                   10

<210> SEQ ID NO 72
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 72

Glu Arg Pro Arg Leu Cys His Lys Gly Pro Leu Cys Phe
1               5                   10

<210> SEQ ID NO 73
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 73

Glu Arg Pro Arg Leu Cys His Lys Gly Pro Leu Cys Phe
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, PyroGlu, Isn, Gln, Ala, Lys,
      5-amino-valeric acid or absent
<220> FEATURE:
<221> NAME/KEY: MOD_RES
<222> LOCATION: (2)..(2)
<223> OTHER INFORMATION: Arg, Ala, D-Arg, N-Me-Arg, Lys, His, homoPhe,
      HomoLys, Phe, Glu or Orn
<220> FEATURE:
<221> NAME/KEY: MOD_RES
<222> LOCATION: (3)..(3)
<223> OTHER INFORMATION: Pro, Ala, D-Ala, D-Pro, 4-PhP, Lys, Asp,
      pipecolic acid or Cys
<220> FEATURE:
<221> NAME/KEY: MOD_RES
<222> LOCATION: (4)..(4)
<223> OTHER INFORMATION: Arg, Ala, D-Arg, N-Me-Arg, Phe, Glu or Cys
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp, 4-PhF
      or Phe
<220> FEATURE:
<221> NAME/KEY: MOD_RES
<222> LOCATION: (6)..(6)
<223> OTHER INFORMATION: Cys, D-Cys, homoCys, D-homoCys, Lys, Asp, Orn,
      Dab or Glu
<220> FEATURE:
<221> NAME/KEY: MOD_RES
<222> LOCATION: (7)..(7)
<223> OTHER INFORMATION: His, D-His, Ala, N-Me-Ala, D-Ala, Aib, Lys,
      Nal, Phe, Pro, Dap, Asn, Glu or Cys
<220> FEATURE:
<221> NAME/KEY: MOD_RES
<222> LOCATION: (8)..(8)
<223> OTHER INFORMATION: Lys, D-Lys, Phe, D-Phe, Ala, homoPhe, N-Me-Arg,
      Glu or 4-amino-Isn
<220> FEATURE:
<221> NAME/KEY: MOD_RES
<222> LOCATION: (9)..(9)
<223> OTHER INFORMATION: Gly, N-Me-Gly, Ala, Asp, Leu, Arg or Aib
<220> FEATURE:
<221> NAME/KEY: MOD_RES
<222> LOCATION: (10)..(10)
<223> OTHER INFORMATION: Pro, Ala, D-Pro, 4-PhP or pipecolic acid
<220> FEATURE:
<221> NAME/KEY: MOD_RES
<222> LOCATION: (11)..(11)
<223> OTHER INFORMATION: Met, D-Nle, Nle, N-Me-Nle, M(O), Ala, Phe, Tyr,
      Leu, Lys, 3-PyA or Cha
```

```
<220> FEATURE:
<221> NAME/KEY: MOD_RES
<222> LOCATION: (12)..(12)
<223> OTHER INFORMATION: Cys, D-Cys, homoCys, D-homoCys, Lys, Asp, Orn,
      Dab, Glu, Phe or D-Phe
<220> FEATURE:
<221> NAME/KEY: MOD_RES
<222> LOCATION: (13)..(13)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap, His, Glu or absent

<400> SEQUENCE: 74

Xaa Xaa Xaa Xaa Xaa Xaa Xaa Xaa Xaa Xaa Xaa Xaa Xaa
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, PyroGlu, Gln, Isn or absent
<220> FEATURE:
<221> NAME/KEY: MOD_RES
<222> LOCATION: (5)..(5)
<223> OTHER INFORMATION: Leu or Cha
<220> FEATURE:
<221> NAME/KEY: MOD_RES
<222> LOCATION: (6)..(6)
<223> OTHER INFORMATION: Cys, D-Cys, homoCys, D-homoCys, Lys, Asp, Orn,
      Dab or Glu
<220> FEATURE:
<221> NAME/KEY: MOD_RES
<222> LOCATION: (7)..(7)
<223> OTHER INFORMATION: His, Aib, Phe, Lys(Lauroyl) or Lys(palmitoyl)
<220> FEATURE:
<221> NAME/KEY: MOD_RES
<222> LOCATION: (8)..(8)
<223> OTHER INFORMATION: Lys, Phe or 4-amino-Isn
<220> FEATURE:
<221> NAME/KEY: MOD_RES
<222> LOCATION: (9)..(9)
<223> OTHER INFORMATION: Gly or Aib
<220> FEATURE:
<221> NAME/KEY: MOD_RES
<222> LOCATION: (11)..(11)
<223> OTHER INFORMATION: Nle or Cha
<220> FEATURE:
<221> NAME/KEY: MOD_RES
<222> LOCATION: (12)..(12)
<223> OTHER INFORMATION: Cys, D-Cys, homoCys, D-homoCys, Lys, Asp, Orn,
      Dab or Glu
<220> FEATURE:
<221> NAME/KEY: MOD_RES
<222> LOCATION: (13)..(13)
<223> OTHER INFORMATION: Phe, D-Phe, Lys(Lauroyl), Lys(palmitoyl) or
      absent

<400> SEQUENCE: 75

Xaa Arg Pro Arg Xaa Xaa Xaa Xaa Xaa Pro Xaa Xaa Xaa
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Arg, PyroGlu, Isn, Gln, Ala, Lys,
      5-amino-valeric acid or absent
<220> FEATURE:
<221> NAME/KEY: MOD_RES
<222> LOCATION: (2)..(2)
<223> OTHER INFORMATION: Arg, Ala, D-Arg, N-Me-Arg, Lys, His, homoPhe,
      HomoLys, Phe, Glu or Orn
<220> FEATURE:
<221> NAME/KEY: MOD_RES
<222> LOCATION: (3)..(3)
<223> OTHER INFORMATION: Pro, Ala, D-Ala, D-Pro, 4-PhP, Lys, Asp,
      pipecolic acid or Cys
<220> FEATURE:
<221> NAME/KEY: MOD_RES
<222> LOCATION: (4)..(4)
<223> OTHER INFORMATION: Arg, Ala, D-Arg, N-Me-Arg, Phe, Glu or Cys
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp, 4-PhF
      or Phe
<220> FEATURE:
<221> NAME/KEY: MOD_RES
<222> LOCATION: (6)..(6)
<223> OTHER INFORMATION: Lys, Orn, Dab, Glu or Asp
<220> FEATURE:
<221> NAME/KEY: MOD_RES
<222> LOCATION: (7)..(7)
<223> OTHER INFORMATION: His, D-His, Ala, N-Me-Ala, D-Ala, Aib, Lys,
      Nal, Phe, Pro, Dap, Asn, Glu, Cys, Lys(Lauroyl) or Lys(palmitoyl)
<220> FEATURE:
<221> NAME/KEY: MOD_RES
<222> LOCATION: (8)..(8)
<223> OTHER INFORMATION: Lys, D-Lys, Phe, D-Phe, Ala, homoPhe, N-Me-Arg,
      Glu or 4-amino-Isn
<220> FEATURE:
<221> NAME/KEY: MOD_RES
<222> LOCATION: (9)..(9)
<223> OTHER INFORMATION: Gly, N-Me-Gly, Ala, Asp, Leu, Arg or Aib
<220> FEATURE:
<221> NAME/KEY: MOD_RES
<222> LOCATION: (10)..(10)
<223> OTHER INFORMATION: Pro, Ala, D-Pro, 4-PhP or pipecolic acid
<220> FEATURE:
<221> NAME/KEY: MOD_RES
<222> LOCATION: (11)..(11)
<223> OTHER INFORMATION: Met, D-Nle, Nle, N-Me-Nle, M(O), Ala, Phe, Tyr,
      Leu, Lys, 3-PyA or Cha
<220> FEATURE:
<221> NAME/KEY: MOD_RES
<222> LOCATION: (12)..(12)
<223> OTHER INFORMATION: Lys, Orn, Dab, Glu or Asp
<220> FEATURE:
<221> NAME/KEY: MOD_RES
<222> LOCATION: (13)..(13)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap, His, Glu, Lys(Lauroyl),
      Lys(palmitoyl) or absent

<400> SEQUENCE: 76

Xaa Xaa Xaa Xaa Xaa Xaa Xaa Xaa Xaa Xaa Xaa Xaa Xaa
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, PyroGlu, Isn, Gln, Ala, Lys,
      5-amino-valeric acid or absent
<220> FEATURE:
```

```
<221> NAME/KEY: MOD_RES
<222> LOCATION: (2)..(2)
<223> OTHER INFORMATION: Arg, Ala, D-Arg, N-Me-Arg, Lys, His, homoPhe,
      HomoLys, Phe, Glu or Orn
<220> FEATURE:
<221> NAME/KEY: MOD_RES
<222> LOCATION: (3)..(3)
<223> OTHER INFORMATION: Pro, Ala, D-Ala, D-Pro, 4-PhP, Lys, Asp,
      pipecolic acid or Cys
<220> FEATURE:
<221> NAME/KEY: MOD_RES
<222> LOCATION: (4)..(4)
<223> OTHER INFORMATION: Arg, Ala, D-Arg, N-Me-Arg, Phe, Glu or Cys
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp, 4-PhF
      or Phe
<220> FEATURE:
<221> NAME/KEY: MOD_RES
<222> LOCATION: (7)..(7)
<223> OTHER INFORMATION: His, D-His, Ala, N-Me-Ala, D-Ala, Aib, Lys,
      Nal, Phe, Pro, Dap, Asn, Glu, Cys, Lys(Lauroyl) or Lys(palmitoyl)
<220> FEATURE:
<221> NAME/KEY: MOD_RES
<222> LOCATION: (8)..(8)
<223> OTHER INFORMATION: Lys, D-Lys, Phe, D-Phe, Ala, homoPhe, N-Me-Arg,
      Glu or 4-amino-Isn
<220> FEATURE:
<221> NAME/KEY: MOD_RES
<222> LOCATION: (9)..(9)
<223> OTHER INFORMATION: Gly, N-Me-Gly, Ala, Asp, Leu, Arg or Aib
<220> FEATURE:
<221> NAME/KEY: MOD_RES
<222> LOCATION: (10)..(10)
<223> OTHER INFORMATION: Pro, Ala, D-Pro, 4-PhP or pipecolic acid
<220> FEATURE:
<221> NAME/KEY: MOD_RES
<222> LOCATION: (11)..(11)
<223> OTHER INFORMATION: Met, D-Nle, Nle, N-Me-Nle, M(O), Ala, Phe, Tyr,
      Leu, Lys, 3-PyA or Cha
<220> FEATURE:
<221> NAME/KEY: MOD_RES
<222> LOCATION: (13)..(13)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap, His, Glu, Lys(Lauroyl),
      Lys(palmitoyl) or absent

<400> SEQUENCE: 77

Xaa Xaa Xaa Xaa Xaa Cys Xaa Xaa Xaa Xaa Xaa Cys Xaa
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, PyroGlu, Isn, Gln, Ala, Lys,
      5-amino-valeric acid or absent
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp, 4-PhF
      or Phe
<220> FEATURE:
<221> NAME/KEY: MOD_RES
<222> LOCATION: (7)..(7)
<223> OTHER INFORMATION: His, D-His, Ala, N-Me-Ala, D-Ala, Aib, Lys,
      Nal, Phe, Pro, Dap, Asn, Glu, Cys, Lys(Lauroyl) or Lys(palmitoyl)
<220> FEATURE:
<221> NAME/KEY: MOD_RES
<222> LOCATION: (8)..(8)
```

```
<223> OTHER INFORMATION: Lys, D-Lys, Phe, D-Phe, Ala, homoPhe, N-Me-Arg,
      Glu or 4-amino-Isn
<220> FEATURE:
<221> NAME/KEY: MOD_RES
<222> LOCATION: (9)..(9)
<223> OTHER INFORMATION: Gly, N-Me-Gly, Ala, Asp, Leu, Arg or Aib
<220> FEATURE:
<221> NAME/KEY: MOD_RES
<222> LOCATION: (11)..(11)
<223> OTHER INFORMATION: Met, D-Nle, Nle, N-Me-Nle, M(O), Ala, Phe, Tyr,
      Leu, Lys, 3-PyA or Cha
<220> FEATURE:
<221> NAME/KEY: MOD_RES
<222> LOCATION: (13)..(13)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap, His, Glu, Lys(Lauroyl),
      Lys(palmitoyl) or absent

<400> SEQUENCE: 78

Xaa Arg Pro Arg Xaa Cys Xaa Xaa Xaa Pro Xaa Cys Xaa
1               5                   10

<210> SEQ ID NO 79
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, PyroGlu, Isn, Gln, Ala, Lys,
      5-amino-valeric acid or absent
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp, 4-PhF
      or Phe
<220> FEATURE:
<221> NAME/KEY: MOD_RES
<222> LOCATION: (6)..(6)
<223> OTHER INFORMATION: Cys, D-Cys, homoCys, D-homoCys, Lys, Asp, Orn,
      Dab or Glu
<220> FEATURE:
<221> NAME/KEY: MOD_RES
<222> LOCATION: (7)..(7)
<223> OTHER INFORMATION: His, D-His, Ala, N-Me-Ala, D-Ala, Aib, Lys,
      Nal, Phe, Pro, Dap, Asn, Glu, Cys, Lys(Lauroyl) or Lys(palmitoyl)
<220> FEATURE:
<221> NAME/KEY: MOD_RES
<222> LOCATION: (11)..(11)
<223> OTHER INFORMATION: Met, D-Nle, Nle, N-Me-Nle, M(O), Ala, Phe, Tyr,
      Leu, Lys, 3-PyA or Cha
<220> FEATURE:
<221> NAME/KEY: MOD_RES
<222> LOCATION: (12)..(12)
<223> OTHER INFORMATION: Cys, D-Cys, homoCys, D-homoCys, Lys, Asp, Orn,
      Dab, Glu, Phe or D-Phe
<220> FEATURE:
<221> NAME/KEY: MOD_RES
<222> LOCATION: (13)..(13)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap, His, Glu, Lys(Lauroyl),
      Lys(palmitoyl) or absent

<400> SEQUENCE: 79

Xaa Arg Pro Arg Xaa Xaa Xaa Lys Gly Pro Xaa Xaa Xaa
1               5                   10

<210> SEQ ID NO 80
<211> LENGTH: 13
<212> TYPE: PRT
<213> ORGANISM: Artificial Sequence
<220> FEATURE:
```

-continued

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, PyroGlu, Isn, Gln, Ala, Lys,
      5-amino-valeric acid or absent
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp, 4-PhF
      or Phe
<220> FEATURE:
<221> NAME/KEY: MOD_RES
<222> LOCATION: (7)..(7)
<223> OTHER INFORMATION: His, D-His, Ala, N-Me-Ala, D-Ala, Aib, Lys,
      Nal, Phe, Pro, Dap, Asn, Glu, Cys, Lys(Lauroyl) or Lys(palmitoyl)
<220> FEATURE:
<221> NAME/KEY: MOD_RES
<222> LOCATION: (11)..(11)
<223> OTHER INFORMATION: Met, D-Nle, Nle, N-Me-Nle, M(O), Ala, Phe, Tyr,
      Leu, Lys, 3-PyA or Cha
<220> FEATURE:
<221> NAME/KEY: MOD_RES
<222> LOCATION: (13)..(13)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap, His, Glu, Lys(Lauroyl),
      Lys(palmitoyl) or absent

<400> SEQUENCE: 80

Xaa Arg Pro Arg Xaa Cys Xaa Lys Gly Pro Xaa Cys Xaa
1               5                   10

<210> SEQ ID NO 81
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, PyroGlu, Isn, Gln, Ala, Lys,
      5-amino-valeric acid or absent
<220> FEATURE:
<221> NAME/KEY: MOD_RES
<222> LOCATION: (2)..(2)
<223> OTHER INFORMATION: Arg, Ala, D-Arg, N-Me-Arg, Lys, His, homoPhe,
      HomoLys, Phe, Glu or Orn
<220> FEATURE:
<221> NAME/KEY: MOD_RES
<222> LOCATION: (4)..(4)
<223> OTHER INFORMATION: Arg, Ala, D-Arg, N-Me-Arg, Phe, Glu or Cys
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp, 4-PhF
      or Phe
<220> FEATURE:
<221> NAME/KEY: MOD_RES
<222> LOCATION: (8)..(8)
<223> OTHER INFORMATION: Lys, D-Lys, Phe, D-Phe, Ala, homoPhe, N-Me-Arg,
      Glu or 4-amino-Isn
<220> FEATURE:
<221> NAME/KEY: MOD_RES
<222> LOCATION: (9)..(9)
<223> OTHER INFORMATION: Gly, N-Me-Gly, Ala, Asp, Leu, Arg or Aib
<220> FEATURE:
<221> NAME/KEY: MOD_RES
<222> LOCATION: (10)..(10)
<223> OTHER INFORMATION: Pro, Ala, D-Pro, 4-PhP or pipecolic acid
<220> FEATURE:
<221> NAME/KEY: MOD_RES
<222> LOCATION: (11)..(11)
<223> OTHER INFORMATION: Met, D-Nle, Nle, N-Me-Nle, M(O), Ala, Phe, Tyr,
      Leu, Lys, 3-PyA or Cha
```

```
<220> FEATURE:
<221> NAME/KEY: MOD_RES
<222> LOCATION: (13)..(13)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap, His, Glu, or absent

<400> SEQUENCE: 81

Xaa Xaa Cys Xaa Xaa Cys Cys Xaa Xaa Xaa Xaa Cys Xaa
1               5                   10

<210> SEQ ID NO 82
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, PyroGlu, Isn, Gln, Ala, Lys,
      5-amino-valeric acid or absent
<220> FEATURE:
<221> NAME/KEY: MOD_RES
<222> LOCATION: (2)..(2)
<223> OTHER INFORMATION: Arg, Ala, D-Arg, N-Me-Arg, Lys, His, homoPhe,
      HomoLys, Phe, Glu or Orn
<220> FEATURE:
<221> NAME/KEY: MOD_RES
<222> LOCATION: (3)..(3)
<223> OTHER INFORMATION: Pro, Ala, D-Ala, D-Pro, 4-PhP, Lys, Asp,
      pipecolic acid or Cys
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp, 4-PhF
      or Phe
<220> FEATURE:
<221> NAME/KEY: MOD_RES
<222> LOCATION: (8)..(8)
<223> OTHER INFORMATION: Lys, D-Lys, Phe, D-Phe, Ala, homoPhe, N-Me-Arg,
      Glu or 4-amino-Isn
<220> FEATURE:
<221> NAME/KEY: MOD_RES
<222> LOCATION: (9)..(9)
<223> OTHER INFORMATION: Gly, N-Me-Gly, Ala, Asp, Leu, Arg or Aib
<220> FEATURE:
<221> NAME/KEY: MOD_RES
<222> LOCATION: (10)..(10)
<223> OTHER INFORMATION: Pro, Ala, D-Pro, 4-PhP or pipecolic acid
<220> FEATURE:
<221> NAME/KEY: MOD_RES
<222> LOCATION: (11)..(11)
<223> OTHER INFORMATION: Met, D-Nle, Nle, N-Me-Nle, M(O), Ala, Phe, Tyr,
      Leu, Lys, 3-PyA or Cha
<220> FEATURE:
<221> NAME/KEY: MOD_RES
<222> LOCATION: (13)..(13)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap, His, Glu or absent

<400> SEQUENCE: 82

Xaa Xaa Xaa Cys Xaa Cys Cys Xaa Xaa Xaa Xaa Cys Xaa
1               5                   10

<210> SEQ ID NO 83
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Arg, PyroGlu, Isn, Gln, Ala, Lys,
      5-amino-valeric acid or absent
<220> FEATURE:
<221> NAME/KEY: MOD_RES
<222> LOCATION: (2)..(2)
<223> OTHER INFORMATION: Arg, Ala, D-Arg, N-Me-Arg, Lys, His, homoPhe,
      HomoLys, Phe, Glu or Orn
<220> FEATURE:
<221> NAME/KEY: MOD_RES
<222> LOCATION: (3)..(3)
<223> OTHER INFORMATION: Pro, Ala, D-Ala, D-Pro, 4-PhP, Lys, Asp,
      pipecolic acid or Cys
<220> FEATURE:
<221> NAME/KEY: MOD_RES
<222> LOCATION: (4)..(4)
<223> OTHER INFORMATION: Arg, Ala, D-Arg, N-Me-Arg, Phe, Glu or Cys
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp, 4-PhF
      or Phe
<220> FEATURE:
<221> NAME/KEY: MOD_RES
<222> LOCATION: (6)..(6)
<223> OTHER INFORMATION: Cys, D-Cys, homoCys, D-homoCys, Lys, Asp, Orn,
      Dab or Glu
<220> FEATURE:
<221> NAME/KEY: MOD_RES
<222> LOCATION: (7)..(7)
<223> OTHER INFORMATION: His, D-His, Ala, N-Me-Ala, D-Ala, Aib, Lys,
      Nal, Phe, Pro, Dap, Asn, Glu, Cys, Lys(Lauroyl) or Lys(palmitoyl)
<220> FEATURE:
<221> NAME/KEY: MOD_RES
<222> LOCATION: (8)..(8)
<223> OTHER INFORMATION: Lys, D-Lys, Phe, D-Phe, Ala, homoPhe, N-Me-Arg,
      Glu or 4-amino-Isn
<220> FEATURE:
<221> NAME/KEY: MOD_RES
<222> LOCATION: (9)..(9)
<223> OTHER INFORMATION: Gly, N-Me-Gly, Ala, Asp, Leu, Arg or Aib
<220> FEATURE:
<221> NAME/KEY: MOD_RES
<222> LOCATION: (10)..(10)
<223> OTHER INFORMATION: Pro, Ala, D-Pro, 4-PhP or pipecolic acid
<220> FEATURE:
<221> NAME/KEY: MOD_RES
<222> LOCATION: (11)..(11)
<223> OTHER INFORMATION: Met, D-Nle, Nle, N-Me-Nle, M(O), Ala, Phe, Tyr,
      Leu, Lys, 3-PyA or Cha
<220> FEATURE:
<221> NAME/KEY: MOD_RES
<222> LOCATION: (12)..(12)
<223> OTHER INFORMATION: Cys, D-Cys, homoCys, D-homoCys, Lys, Asp, Orn,
      Dab, Glu, Phe or D-Phe
<220> FEATURE:
<221> NAME/KEY: MOD_RES
<222> LOCATION: (13)..(13)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap, His, Glu, Lys(Lauroyl),
      Lys(palmitoyl) or absent
<220> FEATURE:
<221> NAME/KEY: misc_feature
<222> LOCATION: (14)..(17)
<223> OTHER INFORMATION: This region may encompass 1, 2, 3 or 4 residues
<220> FEATURE:
<221> NAME/KEY: misc_feature
<222> LOCATION: (1)..(17)
<223> OTHER INFORMATION: Cyclic peptide

<400> SEQUENCE: 83

Xaa Xaa Xaa Xaa Xaa Xaa Xaa Xaa Xaa Xaa Xaa Xaa Xaa Gly Gly Gly
1               5                   10                  15

Gly

<210> SEQ ID NO 84
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Arg, Ala, D-Arg, N-Me-Arg, Lys, His, homoPhe,
      HomoLys, Phe, Glu or Orn
<220> FEATURE:
<221> NAME/KEY: MOD_RES
<222> LOCATION: (3)..(3)
<223> OTHER INFORMATION: Pro, Ala, D-Ala, D-Pro, 4-PhF, Lys, Asp,
      pipecolic acid or Cys
<220> FEATURE:
<221> NAME/KEY: MOD_RES
<222> LOCATION: (4)..(4)
<223> OTHER INFORMATION: Arg, Ala, D-Arg, N-Me-Arg, Phe, Glu or Cys
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp, 4-PhF
      or Phe
<220> FEATURE:
<221> NAME/KEY: MOD_RES
<222> LOCATION: (6)..(6)
<223> OTHER INFORMATION: Cys, D-Cys, homoCys, D-homoCys, Lys, Asp, Orn,
      Dab or Glu
<220> FEATURE:
<221> NAME/KEY: MOD_RES
<222> LOCATION: (7)..(7)
<223> OTHER INFORMATION: His, D-His, Ala, N-Me-Ala, D-Ala, Aib, Lys,
      Nal, Phe, Pro, Dap, Asn, Glu, Cys, Lys(Lauroyl) or Lys(palmitoyl)
<220> FEATURE:
<221> NAME/KEY: MOD_RES
<222> LOCATION: (8)..(8)
<223> OTHER INFORMATION: Lys, D-Lys, Phe, D-Phe, Ala, homoPhe, N-Me-Arg,
      Glu or 4-amino-Isn
<220> FEATURE:
<221> NAME/KEY: MOD_RES
<222> LOCATION: (9)..(9)
<223> OTHER INFORMATION: Gly, N-Me-Gly, Ala, Asp, Leu, Arg or Aib
<220> FEATURE:
<221> NAME/KEY: MOD_RES
<222> LOCATION: (10)..(10)
<223> OTHER INFORMATION: Pro, Ala, D-Pro, 4-PhF or pipecolic acid
<220> FEATURE:
<221> NAME/KEY: MOD_RES
<222> LOCATION: (11)..(11)
<223> OTHER INFORMATION: Met, D-Nle, Nle, N-Me-Nle, M(O), Ala, Phe, Tyr,
      Leu, Lys, 3-PyA or Cha
<220> FEATURE:
<221> NAME/KEY: MOD_RES
<222> LOCATION: (12)..(12)
<223> OTHER INFORMATION: Cys, D-Cys, homoCys, D-homoCys, Lys, Asp, Orn,
      Dab, Glu, Phe or D-Phe
<220> FEATURE:
<221> NAME/KEY: misc_feature
<222> LOCATION: (1)..(15)
<223> OTHER INFORMATION: Cyclic peptide

<400> SEQUENCE: 84

Gln Xaa Xaa Xaa Xaa Xaa Xaa Xaa Xaa Xaa Xaa Phe Gly Gly
1               5                   10                  15

<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, PyroGlu, Isn, Gln, Ala, Lys,
```

```
      5-amino-valeric acid or absent
<220> FEATURE:
<221> NAME/KEY: MOD_RES
<222> LOCATION: (2)..(2)
<223> OTHER INFORMATION: Arg, Ala, D-Arg, N-Me-Arg, Lys, His, homoPhe,
      HomoLys, Phe, Glu or Orn
<220> FEATURE:
<221> NAME/KEY: MOD_RES
<222> LOCATION: (3)..(3)
<223> OTHER INFORMATION: Pro, Ala, D-Ala, D-Pro, 4-PhP, Lys, Asp,
      pipecolic acid or Cys
<220> FEATURE:
<221> NAME/KEY: MOD_RES
<222> LOCATION: (4)..(4)
<223> OTHER INFORMATION: Arg, Ala, D-Arg, N-Me-Arg, Phe, Glu or Cys
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp, 4-PhF
      or Phe
<220> FEATURE:
<221> NAME/KEY: MOD_RES
<222> LOCATION: (7)..(7)
<223> OTHER INFORMATION: His, D-His, Ala, N-Me-Ala, D-Ala, Aib, Lys,
      Nal, Phe, Pro, Dap, Asn, Glu or Cys
<220> FEATURE:
<221> NAME/KEY: MOD_RES
<222> LOCATION: (8)..(8)
<223> OTHER INFORMATION: Lys, D-Lys, Phe, D-Phe, Ala, homoPhe, N-Me-Arg,
      Glu or 4-amino-Isn
<220> FEATURE:
<221> NAME/KEY: MOD_RES
<222> LOCATION: (9)..(9)
<223> OTHER INFORMATION: Gly, N-Me-Gly, Ala, Asp, Leu, Arg or Aib
<220> FEATURE:
<221> NAME/KEY: MOD_RES
<222> LOCATION: (10)..(10)
<223> OTHER INFORMATION: Pro, Ala, D-Pro, 4-PhP or pipecolic acid
<220> FEATURE:
<221> NAME/KEY: MOD_RES
<222> LOCATION: (11)..(11)
<223> OTHER INFORMATION: Met, D-Nle, Nle, N-Me-Nle, M(O), Ala, Phe, Tyr,
      Leu, Lys, 3-PyA or Cha
<220> FEATURE:
<221> NAME/KEY: MOD_RES
<222> LOCATION: (12)..(12)
<223> OTHER INFORMATION: Phe or D-Phe

<400> SEQUENCE: 85

Xaa Xaa Xaa Xaa Xaa Lys Xaa Xaa Xaa Xaa Xaa Phe
1               5                   10

<210> SEQ ID NO 86
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (2)..(2)
<223> OTHER INFORMATION: Arg, Ala, D-Arg, N-Me-Arg, Lys, His, homoPhe,
      HomoLys, Phe, Glu or Orn
<220> FEATURE:
<221> NAME/KEY: MOD_RES
<222> LOCATION: (3)..(3)
<223> OTHER INFORMATION: Pro, Ala, D-Ala, D-Pro, 4-PhP, Lys, Asp,
      pipecolic acid or Cys
<220> FEATURE:
<221> NAME/KEY: MOD_RES
<222> LOCATION: (4)..(4)
<223> OTHER INFORMATION: Arg, Ala, D-Arg, N-Me-Arg, Phe, Glu or Cys
```

```
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp, 4-PhF
      or Phe
<220> FEATURE:
<221> NAME/KEY: MOD_RES
<222> LOCATION: (6)..(6)
<223> OTHER INFORMATION: Cys, D-Cys, homoCys, D-homoCys, Lys, Asp, Orn,
      Dab or Glu
<220> FEATURE:
<221> NAME/KEY: MOD_RES
<222> LOCATION: (7)..(7)
<223> OTHER INFORMATION: His, D-His, Ala, N-Me-Ala, D-Ala, Aib, Lys,
      Nal, Phe, Pro, Dap, Asn, Glu, Cys, Lys(Lauroyl) or Lys(palmitoyl)
<220> FEATURE:
<221> NAME/KEY: MOD_RES
<222> LOCATION: (8)..(8)
<223> OTHER INFORMATION: Lys, D-Lys, Phe, D-Phe, Ala, homoPhe, N-Me-Arg,
      Glu or 4-amino-Isn
<220> FEATURE:
<221> NAME/KEY: MOD_RES
<222> LOCATION: (9)..(9)
<223> OTHER INFORMATION: Gly, N-Me-Gly, Ala, Asp, Leu, Arg or Aib
<220> FEATURE:
<221> NAME/KEY: MOD_RES
<222> LOCATION: (10)..(10)
<223> OTHER INFORMATION: Pro, Ala, D-Pro, 4-PhP or pipecolic acid
<220> FEATURE:
<221> NAME/KEY: MOD_RES
<222> LOCATION: (11)..(11)
<223> OTHER INFORMATION: Met, D-Nle, Nle, N-Me-Nle, M(O), Ala, Phe, Tyr,
      Leu, Lys, 3-PyA or Cha
<220> FEATURE:
<221> NAME/KEY: MOD_RES
<222> LOCATION: (12)..(12)
<223> OTHER INFORMATION: Cys, D-Cys, homoCys, D-homoCys, Lys, Asp, Orn,
      Dab, Glu, Phe or D-Phe
<220> FEATURE:
<221> NAME/KEY: MOD_RES
<222> LOCATION: (13)..(13)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap, His, Glu, Lys(Lauroyl),
      Lys(palmitoyl) or absent

<400> SEQUENCE: 86

Glu Xaa Xaa Xaa Xaa Xaa Xaa Xaa Xaa Xaa Xaa Xaa
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, Ala, D-Arg, N-Me-Arg, Lys, His, homoPhe,
      HomoLys, Phe, Glu or Orn
<220> FEATURE:
<221> NAME/KEY: MOD_RES
<222> LOCATION: (2)..(2)
<223> OTHER INFORMATION: Pro, Ala, D-Ala, D-Pro, 4-PhP, Lys, Asp,
      pipecolic acid or Cys
<220> FEATURE:
<221> NAME/KEY: MOD_RES
<222> LOCATION: (3)..(3)
<223> OTHER INFORMATION: Arg, Ala, D-Arg, N-Me-Arg, Phe, Glu or Cys
<220> FEATURE:
<221> NAME/KEY: MOD_RES
<222> LOCATION: (4)..(4)
<223> OTHER INFORMATION: Leu, Cha, Ala, D-Leu, N-Me-Leu, Lys, Asp, 4-PhF
      or Phe
<220> FEATURE:
<221> NAME/KEY: MOD_RES
```

-continued

```
<222> LOCATION: (5)..(5)
<223> OTHER INFORMATION: Cys, D-Cys, homoCys, D-homoCys, Lys, Asp, Orn,
      Dab or Glu
<220> FEATURE:
<221> NAME/KEY: MOD_RES
<222> LOCATION: (6)..(6)
<223> OTHER INFORMATION: His, D-His, Ala, N-Me-Ala, D-Ala, Aib, Lys,
      Nal, Phe, Pro, Dap, Asn, Glu, Cys, Lys(Lauroyl) or Lys(palmitoyl)
<220> FEATURE:
<221> NAME/KEY: MOD_RES
<222> LOCATION: (7)..(7)
<223> OTHER INFORMATION: Lys, D-Lys, Phe, D-Phe, Ala, homoPhe, N-Me-Arg,
      Glu or 4-amino-Isn
<220> FEATURE:
<221> NAME/KEY: MOD_RES
<222> LOCATION: (8)..(8)
<223> OTHER INFORMATION: Gly, N-Me-Gly, Ala, Asp, Leu, Arg or Aib
<220> FEATURE:
<221> NAME/KEY: MOD_RES
<222> LOCATION: (9)..(9)
<223> OTHER INFORMATION: Pro, Ala, D-Pro, 4-PhP or pipecolic acid
<220> FEATURE:
<221> NAME/KEY: MOD_RES
<222> LOCATION: (10)..(10)
<223> OTHER INFORMATION: Met, D-Nle, Nle, N-Me-Nle, M(O), Ala, Phe, Tyr,
      Leu, Lys, 3-PyA or Cha
<220> FEATURE:
<221> NAME/KEY: MOD_RES
<222> LOCATION: (11)..(11)
<223> OTHER INFORMATION: Cys, D-Cys, homoCys, D-homoCys, Lys, Asp, Orn,
      Dab, Glu, Phe or D-Phe
<220> FEATURE:
<221> NAME/KEY: MOD_RES
<222> LOCATION: (12)..(12)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap, His, Glu, Lys(Lauroyl),
      Lys(palmitoyl) or absent

<400> SEQUENCE: 87

Xaa Xaa Xaa Xaa Xaa Xaa Xaa Xaa Xaa Xaa Xaa Xaa
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, PyroGlu, Isn, Gln, Ala, Lys,
      5-amino-valeric acid or absent
<220> FEATURE:
<221> NAME/KEY: MOD_RES
<222> LOCATION: (2)..(2)
<223> OTHER INFORMATION: Arg, Ala, D-Arg, N-Me-Arg, Lys, His, homoPhe,
      HomoLys, Phe, Glu or Orn
<220> FEATURE:
<221> NAME/KEY: MOD_RES
<222> LOCATION: (3)..(3)
<223> OTHER INFORMATION: Pro, Ala, D-Ala, D-Pro, 4-PhP, Lys, Asp,
      pipecolic acid or Cys
<220> FEATURE:
<221> NAME/KEY: MOD_RES
<222> LOCATION: (4)..(4)
<223> OTHER INFORMATION: Arg, Ala, D-Arg, N-Me-Arg, Phe, Glu or Cys
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp, 4-PhF
      or Phe
<220> FEATURE:
<221> NAME/KEY: MOD_RES
<222> LOCATION: (6)..(6)
<223> OTHER INFORMATION: Cys, D-Cys, homoCys, D-homoCys, Lys, Asp, Orn,
```

```
             Dab or Glu
<220> FEATURE:
<221> NAME/KEY: MOD_RES
<222> LOCATION: (7)..(7)
<223> OTHER INFORMATION: His, D-His, Ala, N-Me-Ala, D-Ala, Aib, Lys,
      Nal, Phe, Pro, Dap, Asn, Glu, Cys, Lys(Lauroyl) or Lys(palmitoyl)
<220> FEATURE:
<221> NAME/KEY: MOD_RES
<222> LOCATION: (8)..(8)
<223> OTHER INFORMATION: Lys, D-Lys, Phe, D-Phe, Ala, homoPhe, N-Me-Arg,
      Glu or 4-amino-Isn
<220> FEATURE:
<221> NAME/KEY: MOD_RES
<222> LOCATION: (9)..(9)
<223> OTHER INFORMATION: Gly, N-Me-Gly, Ala, Asp, Leu, Arg or Aib
<220> FEATURE:
<221> NAME/KEY: MOD_RES
<222> LOCATION: (10)..(10)
<223> OTHER INFORMATION: Pro, Ala, D-Pro, 4-PhP or pipecolic acid
<220> FEATURE:
<221> NAME/KEY: MOD_RES
<222> LOCATION: (11)..(11)
<223> OTHER INFORMATION: Met, D-Nle, Nle, N-Me-Nle, M(O), Ala, Phe, Tyr,
      Leu, Lys, 3-PyA or Cha
<220> FEATURE:
<221> NAME/KEY: MOD_RES
<222> LOCATION: (12)..(12)
<223> OTHER INFORMATION: Cys, D-Cys, homoCys, D-homoCys, Lys, Asp, Orn,
      Dab, Glu, Phe or D-Phe

<400> SEQUENCE: 88

Xaa Xaa Xaa Xaa Xaa Xaa Xaa Xaa Xaa Xaa Xaa Xaa Phe
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, PyroGlu, Isn, Gln, Ala, Lys,
      5-amino-valeric acid or absent
<220> FEATURE:
<221> NAME/KEY: MOD_RES
<222> LOCATION: (2)..(2)
<223> OTHER INFORMATION: Arg, Ala, D-Arg, N-Me-Arg, Lys, His, homoPhe,
      HomoLys, Phe, Glu or Orn
<220> FEATURE:
<221> NAME/KEY: MOD_RES
<222> LOCATION: (3)..(3)
<223> OTHER INFORMATION: Pro, Ala, D-Ala, D-Pro, 4-PhP, Lys, Asp,
      pipecolic acid or Cys
<220> FEATURE:
<221> NAME/KEY: MOD_RES
<222> LOCATION: (4)..(4)
<223> OTHER INFORMATION: Arg, Ala, D-Arg, N-Me-Arg, Phe, Glu or Cys
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp, 4-PhF
      or Phe
<220> FEATURE:
<221> NAME/KEY: MOD_RES
<222> LOCATION: (6)..(6)
<223> OTHER INFORMATION: Cys, D-Cys, homoCys, D-homoCys, Lys, Asp, Orn,
      Dab or Glu
<220> FEATURE:
<221> NAME/KEY: MOD_RES
<222> LOCATION: (7)..(7)
<223> OTHER INFORMATION: His, D-His, Ala, N-Me-Ala, D-Ala, Aib, Lys,
      Nal, Phe, Pro, Dap, Asn, Glu, Cys, Lys(Lauroyl) or Lys(palmitoyl)
<220> FEATURE:
<221> NAME/KEY: MOD_RES
```

```
<222> LOCATION: (8)..(8)
<223> OTHER INFORMATION: Lys, D-Lys, Phe, D-Phe, Ala, homoPhe, N-Me-Arg,
      Glu or 4-amino-Isn
<220> FEATURE:
<221> NAME/KEY: MOD_RES
<222> LOCATION: (9)..(9)
<223> OTHER INFORMATION: Gly, N-Me-Gly, Ala, Asp, Leu, Arg or Aib
<220> FEATURE:
<221> NAME/KEY: MOD_RES
<222> LOCATION: (10)..(10)
<223> OTHER INFORMATION: Pro, Ala, D-Pro, 4-PhP or pipecolic acid
<220> FEATURE:
<221> NAME/KEY: MOD_RES
<222> LOCATION: (11)..(11)
<223> OTHER INFORMATION: Met, D-Nle, Nle, N-Me-Nle, M(O), Ala, Phe, Tyr,
      Leu, Lys, 3-PyA or Cha
<220> FEATURE:
<221> NAME/KEY: MOD_RES
<222> LOCATION: (12)..(12)
<223> OTHER INFORMATION: Cys, D-Cys, homoCys, D-homoCys, Lys, Asp, Orn,
      Dab, Glu, Phe or D-Phe

<400> SEQUENCE: 89

Xaa Xaa Xaa Xaa Xaa Xaa Xaa Xaa Xaa Xaa Xaa Xaa
1               5                   10

<210> SEQ ID NO 90
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, PyroGlu, Isn, Gln, Ala, Lys,
      5-amino-valeric acid or absent
<220> FEATURE:
<221> NAME/KEY: MOD_RES
<222> LOCATION: (2)..(2)
<223> OTHER INFORMATION: Arg, Ala, D-Arg, N-Me-Arg, Lys, His, homoPhe,
      HomoLys, Phe, Glu or Orn
<220> FEATURE:
<221> NAME/KEY: MOD_RES
<222> LOCATION: (3)..(3)
<223> OTHER INFORMATION: Pro, Ala, D-Ala, D-Pro, 4-PhP, Lys, Asp,
      pipecolic acid or Cys
<220> FEATURE:
<221> NAME/KEY: MOD_RES
<222> LOCATION: (4)..(4)
<223> OTHER INFORMATION: Arg, Ala, D-Arg, N-Me-Arg, Phe, Glu or Cys
<220> FEATURE:
<221> NAME/KEY: MOD_RES
<222> LOCATION: (6)..(6)
<223> OTHER INFORMATION: Cys, D-Cys, homoCys, D-homoCys, Lys, Asp, Orn,
      Dab or Glu
<220> FEATURE:
<221> NAME/KEY: MOD_RES
<222> LOCATION: (7)..(7)
<223> OTHER INFORMATION: His, D-His, Ala, N-Me-Ala, D-Ala, Aib, Lys,
      Nal, Phe, Pro, Dap, Asn, Glu, Cys, Lys(Lauroyl) or Lys(palmitoyl)
<220> FEATURE:
<221> NAME/KEY: MOD_RES
<222> LOCATION: (8)..(8)
<223> OTHER INFORMATION: Lys, D-Lys, Phe, D-Phe, Ala, homoPhe, N-Me-Arg,
      Glu or 4-amino-Isn
<220> FEATURE:
<221> NAME/KEY: MOD_RES
<222> LOCATION: (9)..(9)
<223> OTHER INFORMATION: Gly, N-Me-Gly, Ala, Asp, Leu, Arg or Aib
<220> FEATURE:
<221> NAME/KEY: MOD_RES
<222> LOCATION: (10)..(10)
<223> OTHER INFORMATION: Pro, Ala, D-Pro, 4-PhP or pipecolic acid
<220> FEATURE:
<221> NAME/KEY: MOD_RES
```

```
<222> LOCATION: (11)..(11)
<223> OTHER INFORMATION: Met, D-Nle, Nle, N-Me-Nle, M(O), Ala, Phe, Tyr,
      Leu, Lys, 3-PyA or Cha
<220> FEATURE:
<221> NAME/KEY: MOD_RES
<222> LOCATION: (12)..(12)
<223> OTHER INFORMATION: Cys, D-Cys, homoCys, D-homoCys, Lys, Asp, Orn,
      Dab, Glu, Phe or D-Phe
<220> FEATURE:
<221> NAME/KEY: MOD_RES
<222> LOCATION: (13)..(13)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap, His, Glu, Lys(Lauroyl),
      Lys(palmitoyl) or absent

<400> SEQUENCE: 90

Xaa Xaa Xaa Xaa Leu Xaa Xaa Xaa Xaa Xaa Xaa Xaa Xaa
1               5                   10

<210> SEQ ID NO 91
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, PyroGlu, Isn, Gln, Ala, Lys,
      5-amino-valeric acid
      or absent
<220> FEATURE:
<221> NAME/KEY: MOD_RES
<222> LOCATION: (2)..(2)
<223> OTHER INFORMATION: Arg, Ala, D-Arg, N-Me-Arg, Lys, His, homoPhe,
      HomoLys, Phe, Glu or Orn
<220> FEATURE:
<221> NAME/KEY: MOD_RES
<222> LOCATION: (3)..(3)
<223> OTHER INFORMATION: Pro, Ala, D-Ala, D-Pro, 4-PhP, Lys, Asp,
      pipecolic acid or Cys
<220> FEATURE:
<221> NAME/KEY: MOD_RES
<222> LOCATION: (4)..(4)
<223> OTHER INFORMATION: Arg, Ala, D-Arg, N-Me-Arg, Phe, Glu or Cys
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp, 4-PhF
      or Phe
<220> FEATURE:
<221> NAME/KEY: MOD_RES
<222> LOCATION: (6)..(6)
<223> OTHER INFORMATION: Cys, D-Cys, homoCys, D-homoCys, Lys, Asp, Orn,
      Dab or Glu
<220> FEATURE:
<221> NAME/KEY: MOD_RES
<222> LOCATION: (8)..(8)
<223> OTHER INFORMATION: Lys, D-Lys, Phe, D-Phe, Ala, homoPhe, N-Me-Arg,
      Glu or 4-amino-Isn
<220> FEATURE:
<221> NAME/KEY: MOD_RES
<222> LOCATION: (9)..(9)
<223> OTHER INFORMATION: Gly, N-Me-Gly, Ala, Asp, Leu, Arg or Aib
<220> FEATURE:
<221> NAME/KEY: MOD_RES
<222> LOCATION: (10)..(10)
<223> OTHER INFORMATION: Pro, Ala, D-Pro, 4-PhP or pipecolic acid
<220> FEATURE:
<221> NAME/KEY: MOD_RES
<222> LOCATION: (11)..(11)
<223> OTHER INFORMATION: Met, D-Nle, Nle, N-Me-Nle, M(O), Ala, Phe, Tyr,
      Leu, Lys, 3-PyA or Cha
<220> FEATURE:
<221> NAME/KEY: MOD_RES
<222> LOCATION: (12)..(12)
```

```
<223> OTHER INFORMATION: Cys, D-Cys, homoCys, D-homoCys, Lys, Asp, Orn,
      Dab, Glu, Phe or D-Phe
<220> FEATURE:
<221> NAME/KEY: MOD_RES
<222> LOCATION: (13)..(13)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap, His, Glu, Lys(Lauroyl),
      Lys(palmitoyl) or absent

<400> SEQUENCE: 91

Xaa Xaa Xaa Xaa Xaa Xaa His Xaa Xaa Xaa Xaa Xaa Xaa
1               5                   10

<210> SEQ ID NO 92
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, PyroGlu, Isn, Gln, Ala, Lys,
      5-amino-valeric acid or absent
<220> FEATURE:
<221> NAME/KEY: MOD_RES
<222> LOCATION: (2)..(2)
<223> OTHER INFORMATION: Arg, Ala, D-Arg, N-Me-Arg, Lys, His, homoPhe,
      HomoLys, Phe, Glu or Orn
<220> FEATURE:
<221> NAME/KEY: MOD_RES
<222> LOCATION: (3)..(3)
<223> OTHER INFORMATION: Pro, Ala, D-Ala, D-Pro, 4-PhP, Lys, Asp,
      pipecolic acid or Cys
<220> FEATURE:
<221> NAME/KEY: MOD_RES
<222> LOCATION: (4)..(4)
<223> OTHER INFORMATION: Arg, Ala, D-Arg, N-Me-Arg, Phe, Glu or Cys
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp, 4-PhF
      or Phe
<220> FEATURE:
<221> NAME/KEY: MOD_RES
<222> LOCATION: (6)..(6)
<223> OTHER INFORMATION: Cys, D-Cys, homoCys, D-homoCys, Lys, Asp, Orn,
      Dab or Glu
<220> FEATURE:
<221> NAME/KEY: MOD_RES
<222> LOCATION: (7)..(7)
<223> OTHER INFORMATION: His, D-His, Ala, N-Me-Ala, D-Ala, Aib, Lys,
      Nal, Phe, Pro, Dap, Asn, Glu, Cys, Lys(Lauroyl) or Lys(palmitoyl)
<220> FEATURE:
<221> NAME/KEY: MOD_RES
<222> LOCATION: (9)..(9)
<223> OTHER INFORMATION: Gly, N-Me-Gly, Ala, Asp, Leu, Arg or Aib
<220> FEATURE:
<221> NAME/KEY: MOD_RES
<222> LOCATION: (10)..(10)
<223> OTHER INFORMATION: Pro, Ala, D-Pro, 4-PhP or pipecolic acid
<220> FEATURE:
<221> NAME/KEY: MOD_RES
<222> LOCATION: (11)..(11)
<223> OTHER INFORMATION: Met, D-Nle, Nle, N-Me-Nle, M(O), Ala, Phe, Tyr,
      Leu, Lys, 3-PyA or Cha
<220> FEATURE:
<221> NAME/KEY: MOD_RES
<222> LOCATION: (12)..(12)
<223> OTHER INFORMATION: Cys, D-Cys, homoCys, D-homoCys, Lys, Asp, Orn,
      Dab, Glu, Phe or D-Phe
<220> FEATURE:
<221> NAME/KEY: MOD_RES
<222> LOCATION: (13)..(13)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap, His, Glu, Lys(Lauroyl),
```

Lys(palmitoyl) or absent

<400> SEQUENCE: 92

Xaa Xaa Xaa Xaa Xaa Xaa Xaa Lys Xaa Xaa Xaa Xaa Xaa
1               5                   10

<210> SEQ ID NO 93
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, PyroGlu, Isn, Gln, Ala, Lys,
      5-amino-valeric acid or absent
<220> FEATURE:
<221> NAME/KEY: MOD_RES
<222> LOCATION: (2)..(2)
<223> OTHER INFORMATION: Arg, Ala, D-Arg, N-Me-Arg, Lys, His, homoPhe,
      HomoLys, Phe, Glu or Orn
<220> FEATURE:
<221> NAME/KEY: MOD_RES
<222> LOCATION: (3)..(3)
<223> OTHER INFORMATION: Pro, Ala, D-Ala, D-Pro, 4-PhP, Lys, Asp,
      pipecolic acid or Cys
<220> FEATURE:
<221> NAME/KEY: MOD_RES
<222> LOCATION: (4)..(4)
<223> OTHER INFORMATION: Arg, Ala, D-Arg, N-Me-Arg, Phe, Glu or Cys
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp, 4-PhF
      or Phe
<220> FEATURE:
<221> NAME/KEY: MOD_RES
<222> LOCATION: (6)..(6)
<223> OTHER INFORMATION: Cys, D-Cys, homoCys, D-homoCys, Lys, Asp, Orn,
      Dab or Glu
<220> FEATURE:
<221> NAME/KEY: MOD_RES
<222> LOCATION: (7)..(7)
<223> OTHER INFORMATION: His, D-His, Ala, N-Me-Ala, D-Ala, Aib, Lys,
      Nal, Phe, Pro, Dap, Asn, Glu, Cys, Lys(Lauroyl) or Lys(palmitoyl)
<220> FEATURE:
<221> NAME/KEY: MOD_RES
<222> LOCATION: (8)..(8)
<223> OTHER INFORMATION: Lys, D-Lys, Phe, D-Phe, Ala, homoPhe, N-Me-Arg,
      Glu or 4-amino-Isn
<220> FEATURE:
<221> NAME/KEY: MOD_RES
<222> LOCATION: (10)..(10)
<223> OTHER INFORMATION: Pro, Ala, D-Pro, 4-PhP or pipecolic acid
<220> FEATURE:
<221> NAME/KEY: MOD_RES
<222> LOCATION: (11)..(11)
<223> OTHER INFORMATION: Met, D-Nle, Nle, N-Me-Nle, M(O), Ala, Phe, Tyr,
      Leu, Lys, 3-PyA or Cha
<220> FEATURE:
<221> NAME/KEY: MOD_RES
<222> LOCATION: (12)..(12)
<223> OTHER INFORMATION: Cys, D-Cys, homoCys, D-homoCys, Lys, Asp, Orn,
      Dab, Glu, Phe or D-Phe
<220> FEATURE:
<221> NAME/KEY: MOD_RES
<222> LOCATION: (13)..(13)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap, His, Glu, Lys(Lauroyl),
      Lys(palmitoyl) or absent

<400> SEQUENCE: 93

Xaa Xaa Xaa Xaa Xaa Xaa Xaa Xaa Gly Xaa Xaa Xaa Xaa
1               5                   10

```
<210> SEQ ID NO 94
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, PyroGlu, Isn, Gln, Ala, Lys,
      5-amino-valeric acid or absent
<220> FEATURE:
<221> NAME/KEY: MOD_RES
<222> LOCATION: (2)..(2)
<223> OTHER INFORMATION: Arg, Ala, D-Arg, N-Me-Arg, Lys, His, homoPhe,
      HomoLys, Phe, Glu or Orn
<220> FEATURE:
<221> NAME/KEY: MOD_RES
<222> LOCATION: (3)..(3)
<223> OTHER INFORMATION: Pro, Ala, D-Ala, D-Pro, 4-PhP, Lys, Asp,
      pipecolic acid or Cys
<220> FEATURE:
<221> NAME/KEY: MOD_RES
<222> LOCATION: (4)..(4)
<223> OTHER INFORMATION: Arg, Ala, D-Arg, N-Me-Arg, Phe, Glu or Cys
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp, 4-PhF
      or Phe
<220> FEATURE:
<221> NAME/KEY: MOD_RES
<222> LOCATION: (6)..(6)
<223> OTHER INFORMATION: Cys, D-Cys, homoCys, D-homoCys, Lys, Asp, Orn,
      Dab or Glu
<220> FEATURE:
<221> NAME/KEY: MOD_RES
<222> LOCATION: (7)..(7)
<223> OTHER INFORMATION: His, D-His, Ala, N-Me-Ala, D-Ala, Aib, Lys,
      Nal, Phe, Pro, Dap, Asn, Glu, Cys, Lys(Lauroyl) or Lys(palmitoyl)
<220> FEATURE:
<221> NAME/KEY: MOD_RES
<222> LOCATION: (8)..(8)
<223> OTHER INFORMATION: Lys, D-Lys, Phe, D-Phe, Ala, homoPhe, N-Me-Arg,
      Glu or 4-amino-Isn
<220> FEATURE:
<221> NAME/KEY: MOD_RES
<222> LOCATION: (9)..(9)
<223> OTHER INFORMATION: Gly, N-Me-Gly, Ala, Asp, Leu, Arg or Aib
<220> FEATURE:
<221> NAME/KEY: MOD_RES
<222> LOCATION: (10)..(10)
<223> OTHER INFORMATION: Pro, Ala, D-Pro, 4-PhP or pipecolic acid
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (12)..(12)
<223> OTHER INFORMATION: Cys, D-Cys, homoCys, D-homoCys, Lys, Asp, Orn,
      Dab, Glu, Phe or D-Phe
<220> FEATURE:
<221> NAME/KEY: MOD_RES
<222> LOCATION: (13)..(13)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap, His, Glu, Lys(Lauroyl),
      Lys(palmitoyl) or absent

<400> SEQUENCE: 94

Xaa Xaa Xaa Xaa Xaa Xaa Xaa Xaa Xaa Xaa Leu Xaa Xaa
1               5                   10
```